(12) United States Patent
Wootten

(10) Patent No.: US 10,933,096 B2
(45) Date of Patent: Mar. 2, 2021

(54) BIOLOGIC PRESERVING COMPOSITION AND METHODS OF USE

(71) Applicant: Aesthetics Biomedical, Inc., Phoenix, AZ (US)

(72) Inventor: Shaun Wootten, Tempe, AZ (US)

(73) Assignee: AESTHETICS BIOMEDICAL, INC., Phoenix, AZ (US)

( * ) Notice: Subject to any disclaimer, the term of this patent is extended or adjusted under 35 U.S.C. 154(b) by 0 days.

(21) Appl. No.: 16/818,719

(22) Filed: Mar. 13, 2020

(65) Prior Publication Data

US 2020/0215116 A1 Jul. 9, 2020

Related U.S. Application Data

(63) Continuation-in-part of application No. 16/440,774, filed on Jun. 13, 2019, now Pat. No. 10,588,924, which is a continuation-in-part of application No. PCT/US2018/066895, filed on Dec. 20, 2018.

(60) Provisional application No. 62/610,020, filed on Dec. 22, 2017.

(51) Int. Cl.
*A61K 35/19* (2015.01)
*A01N 1/02* (2006.01)
*A61K 9/19* (2006.01)
*A61P 17/00* (2006.01)
*C12N 5/078* (2010.01)
*A61K 9/00* (2006.01)

(52) U.S. Cl.
CPC ............ *A61K 35/19* (2013.01); *A01N 1/0205* (2013.01); *A61K 9/19* (2013.01); *A61P 17/00* (2018.01); *C12N 5/0644* (2013.01); *A61K 9/0014* (2013.01)

(58) Field of Classification Search
CPC .... A61K 35/19; A61K 8/9794; A61K 8/9789; A61K 8/20; A61K 8/24; A61K 8/345
See application file for complete search history.

(56) References Cited

U.S. PATENT DOCUMENTS

| 2009/0042916 A1 | 2/2009 | Sharp et al. |
| 2012/0121534 A1 | 5/2012 | Thorel et al. |
| 2015/0210981 A1 | 7/2015 | Hagiya et al. |

FOREIGN PATENT DOCUMENTS

| CN | 106074343 A | * | 11/2016 |
| CN | 106562921 A | * | 4/2017 |

OTHER PUBLICATIONS

Li, Haoran "Liquid composition for oral cavity containing Chinese medicinal active substance and tea tree essential oil, and its preparation method" CN 106562921 A, ChemAbstract (CA) abstract only, Apr. 19, 2017, 2 pages. (Year: 2017).*
Xuepeng, Zhang et al "Thymol nanoparticle washing-free hand sanitizer and preparation method thereof" CN 106074343 A, ChemAbstract (CA) abstract only, Apr. 19, 2017, 2 pages. (Year: 2016).*
Borzini, P. and Mazzucco, I., 2007. *ISBT Science Series*, 2(1), pp. 272-281.
Ehrenfest et al. 2009 (Trends in Biotechnology vol. 27 No. 3, pp. 158-167).
Everts et al. (JECT. 2006;38:174-187).
Fekete et al. (Cytotherapy. May 2012; 14(5): 540-554).
Gyulkhendanyan et al., BJH, 2013 , (Pub online Feb. 8, 2013) ,161,pp. 245-254; doi: 10.1111/bjh.
Marx et al (Oral Medicine, vol. 85, No. 6, Jun. 1998, pp. 638-647).
Schallmoser et al. (J Vis Exp. Oct. 30, 2009, 32).
Zhu et al. (Osteoarthritis and Cartilage 21 (2013) 1627-1637).
International Search Report issued in application No. PCT/US2018/066895, dated Feb. 20, 2019 , 15 pages.

* cited by examiner

*Primary Examiner* — Aaron J Kosar
(74) *Attorney, Agent, or Firm* — Knobbe, Martens, Olson & Bear LLP

(57) ABSTRACT

Disclosed herein are compositions, methods, and systems for treating skin damage or signs of aging in a subject including obtaining whole blood from the subject, collecting platelet rich plasma (PRP) from the whole blood, forming a first topical formulation having the PRP, providing the first topical formulation to the subject for application to an area of skin damage on the subject, providing a second topical formulation to the subject having an activator such that when the second topical formulation is applied to the area of skin damage on top of the first formulation, the PRP is activated and growth factors are released into the area of skin damage. Systems and kits useful in performing the methods are also disclosed.

36 Claims, 23 Drawing Sheets
(23 of 23 Drawing Sheet(s) Filed in Color)

BIOLOGIC PRESERVING COMPOSITION AND METHODS OF USE

RELATED APPLICATIONS

This application is a continuation-in-part of U.S. patent application Ser. No. 16/440,774, filed on Jun. 13, 2019, which is a continuation-in-part of PCT Patent Application No. PCT/US2018/066895, filed Dec. 20, 2018, which claims the benefit of priority to U.S. Provisional Patent Application No. 62/610,020, filed Dec. 22, 2017, the disclosure of each of which is incorporated by reference herein in its entirety.

BACKGROUND

Field of the Disclosure

The present disclosure relates to the topical formulations and methods useful for treating, preventing, or delaying skin disorders, nail disorders, hair loss, pain, and inflammation. In particular, a base composition is provided that maintains, prolongs, or preserves a biologic in the topical formulations. Methods of making and using the base compositions and topical formulations are also disclosed.

Description

The maintenance and improvement of skin tone, elasticity, and youthful appearance of skin is desirable by many. With age, skin loses elasticity, appears rougher, thins out, and acquires some level of skin damage. This may lead to sagging, discoloration, brown spots, UV damage, and wrinkles. Aside from surgical procedures, such as plastic surgery, to improve the look of skin or injectable treatments such as Botox® or Juvaderm®, many people resort to skin care compositions, including prescription skin treatments, in order to maintain or improve the integrity of their skin and prevent damage. Popular treatments include Retin-A (tretinoin), hydroquinone, glycolic acid, and beta hydroxyl acid to remove a top layer of skin to encourage new skin growth. Many treatments, however, that lead to improved skin tone and elasticity can take weeks to improve the look of skin and can be very irritating. For example, Retin-A and hydroquinone can lead to sun sensitivity, peeling, dryness and even worsening of acne. Glycolic acid and beta hydroxy acid are not advisable for those with sensitive skin. As such, new developments in skin care are desirable. Described herein are compositions for prolonging biologics, such as PRP, for the treatment, prevention, or delay of skin disorders, nail disorders, hair loss, inflammation, and/or pain. Also described herein are methods and kits useful in the preparation of a formulation for such a treatment as well as methods for treating, preventing, or delaying skin disorders, nail disorders, hair loss, or signs of aging.

SUMMARY

Treatments for skin disorders have been limited to drugs that have to be taken orally or for topical use creams and ointments. Embodiments provided herein relate to compositions that preserve, extend the life of, enhance, maintain, sustain, or otherwise prolong biologics, such as cells, proteins, antibodies, blood, serum, plasma, or components thereof, or other biological extracts. In some embodiments, the biologic is platelet rich plasma (PRP). In some embodiments, the compositions that preserve, extend the life of, enhance, maintain, sustain, or otherwise prolong biologics are referred to herein as a base composition.

Accordingly, some embodiments provided herein relate to base compositions for prolonging, preserving, or maintaining a biologic. In some embodiments, the compositions include a cell nutrient, a biological buffer, a viscosity modifying agent, and a botanical extract. In some embodiments, the cell nutrient includes fetal bovine serum (FBS), glucose, human platelet lysate, bovine serum albumin, fibroblast growth supplement, vitamins, trace elements, antioxidants, minerals, amniotic cell culture supplements, or lipopolysaccharides. In some embodiments, the biological buffer includes sodium, potassium, magnesium, calcium, alpha hydroxy acid, beta hydroxy acid, polyhydroxy acid, hyaluronic acid, carboxylic acid, or a cell culture buffering agent, or a derivative or any combination thereof, and wherein the biological buffer preserves the biologic at about or above physiological pH. In some embodiments, the viscosity modifying agent includes polyacrylate crosspolymer-6. In some embodiments, the botanical extract includes an aqueous ferment extract, an alcohol extract, a salicylate, a phenolic compound, or a phytonutrient. In some embodiments, the aqueous ferment extract includes a probiotic fermented botanical extract. In some embodiments, the probiotic includes *Lactobacillus, Lactobacillus casei, Lactobacillus fermentum, Lactobacillus paracasei, Lactobacillus* derivatives, Leuconostoc, Leuconostoc derivatives, Bifidobacterium, Bifidobacterium longum, Bifidobacterium derivatives, Streptococcus, Streptococcus thermophilus, Streptococcus derivatives, Saccharomyces ferment filtrate, or Bacillus ferment. In some embodiments, the probiotic fermented botanical extract includes *Cocos nucifera* fruit fermented with *Lactobacillus*, Leuconostoc kimchi, or Leuconostoc with radish root ferment filtrate. In some embodiments, the salicylate includes an Aspen Bark isolate. In some embodiments, the phenolic compound includes a thymol. In some embodiments, the thymol includes a thymol isomer, a cresol, or O-cymen-5-ol. In some embodiments, the phytonutrient is a Sambucus nigra fruit extract derivative, Populus tremuloides bark extract derivative, or ribes nigrum fruit extract derivative.

Some embodiments provided herein relate to base compositions for prolonging, preserving, or maintaining a biologic. In some embodiments, the composition includes a cell nutrient, a biological buffer, a polymer, a thymol, and an antimicrobial. In some embodiments, the polymer includes a natural or synthetic polymer. In some embodiments, the polymer includes a starch, a xanthan gum, a guar gum, a carrageenan, an alginate, a polysaccharide, a pectin, a gelatin, an agar, a cellulose, a polyacrylate, a polyacrylamide, honey, hydrogel, chitosan, silicone, or a crosspolymer, copolymer, or derivative thereof. In some embodiments, the compositions further include a biologic, wherein the biologic includes platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof. In some embodiments, the biologic is a lyophilized powder. In some embodiments, the base composition prolongs or enhances stability of the biologic and prolongs or enhances stability of components of the biologic. In some embodiments, the base composition inhibits or prevents activation of the biologic, or wherein the base composition maintains, prolongs, preserves, or sustains activity of the biologic or of already active components of the biologic. In some embodiments, the base composition is formulated for cosmetic usage, wherein the cosmetic usage includes topical application to skin.

Some embodiments provided herein relate to topical formulations. In some embodiments, the formulations include any one of the base compositions described herein, including a cell nutrient, a biological buffer, a viscosity modifying agent, and a botanical extract, and a biologic. In some embodiments, the formulations are formulated as a cream, lotion, salve, paste, serum, gel, ointment, liquid, solution, spray, aerosol, or foam. In some embodiments, the biologic includes platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof. In some embodiments, the topical formulation is formulated for cosmetic usage, wherein the cosmetic usage includes topical application to skin.

Some embodiments provided herein relate to methods of diminishing pore size, diminishing bacteria damage, diminishing red areas, reducing skin damage caused by sun, restoring or preventing hair loss, reducing nail disorder, or maintaining or improving skin tone in a subject in need thereof. In some embodiments, the methods include obtaining whole blood from a subject having an area of skin damage, a skin disorder, a nail disorder, or hair loss, centrifuging the blood to separate platelet rich plasma from platelet poor plasma and red blood cells, collecting the platelet rich plasma (PRP), adding the base composition including a cell nutrient, a biological buffer, a viscosity modifying agent, and a botanical extract to the PRP to form PRP admixed solution thereby forming a first topical formulation, wherein the base composition maintains activity of the PRP for a period of time ranging from 30 to 120 days, providing the first topical formulation for application to the subject for treatment of the area of skin damage, nail damage, or hair loss, and activating the PRP. In some embodiments, activating PRP includes increasing the temperature or applying mechanical force, wherein increasing the temperature is achieved by applying mechanical force to the first topical formulation or by removing the first topical formulation from a temperature of less than about 10° C. to a temperature of at least room temperature. In some embodiments, the mechanical force includes rubbing, massaging, spreading, or using a mechanical device. In some embodiments, the mechanical device includes a microdermabrasion, an oscillating fiber, a suction, a microneedling, a roller, or a mechanical cleansing device. In some embodiments, the methods further include providing a second topical formulation for application to the subject over the first topical formulation, wherein the second topical formulation activates the PRP, wherein the second topical formulation includes a cell stimulation cocktail including calcium chloride, hydrochloric acid, thrombin, autologous thrombin, bovine thrombin, collagen, calcium, magnesium, sodium, components of snake venom, batroxobin, or combinations thereof. In some embodiments, the subject suffers from skin damage and signs of aging caused by smoking, alcohol, diet, extreme temperatures, chemicals, stress, lack of sleep, poor diet, poor immune system or a combination thereof. In some embodiments, the skin disorder is selected from a group consisting of stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobata, synovitis-acne-pustulosis-hyperostosis-osteomyelitis syndrome (SAPHO syndrome), steroid rosacea, tar acne, skin cancer, tropical acne or a combination thereof.

Accordingly, embodiments provided herein relate to methods, systems, and compositions for preserving, extending the life of, enhancing, maintaining, sustaining, or otherwise prolonging a biologic, or components of a biologic. In some embodiments, the methods include contacting a biologic with a base composition, wherein the base composition is capable of preserving, extending the life of, enhancing, maintaining, sustaining, or otherwise prolonging the biologic or components of a biologic. In some embodiments, the base composition preserves, extends the life of, enhances, maintains, sustains, or otherwise prolongs a biologic and/or components thereof for a period of more than 30, 40, 50, 60, 70, 80, 90, 100, or 120 days.

In some embodiments, the base compositions include a humectant, sodium bicarbonate, a buffering agent, magnesium chloride, and a viscosity modifying agent. In some embodiments, the base compositions further include a cell culture reagent, and wherein the viscosity modifying agent is potassium chloride, sodium chloride, or both. In some embodiments, the buffering agent is sodium citrate, sodium acetate, or both. In some embodiments, the cell culture reagent is fetal bovine serum (FBS) or a growth medium. In some embodiments, the humectant is glucose. In some embodiments, the composition further includes sodium phosphate. In some embodiments, the base compositions further include an emulsion stabilizer, a chelating agent, an antioxidant, an activation inhibitor, a protein stabilizer, or an enzyme inhibitor. In some embodiments, the base compositions further include a sun protection agent, a skin conditioning agent, a biocide, a biologic buffering agent, a pH adjuster, a cell culture reagent, a skin permeability enhancer, a botanical agent, or a skin delivery system.

In some embodiments, the composition includes water, glycerin, niacinamide, polyacrylate crosspolymer-6, Lonicera caprifolium (honeysuckle) flower extract, Persea gratissima (avocado) oil, Aloe barbadensis leaf juice, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, rosmarinus officinalis (rosemary) leaf oil, *Thymus vulgaris* (thyme) flower/leaf oil, benzyl alcohol, caprylyl glycol, caprylhydroxamic acid, or combinations thereof.

In some embodiments, the composition includes water in an amount ranging from about 85 to 95 wt %, polyacrylate crosspolymer-6 in an amount ranging from about 0.05 to 5 wt %, Lonicera japonica (honeysuckle) flower extract is present in an amount ranging from about 0.05 to 5 wt %, glycerin in an amount ranging from about 0.05 to 5 wt %, niacinamide in an amount ranging from about 0.05 to 5 wt %, Lonicera caprifolium (honeysuckle) flower extract in an amount ranging from about 0.05 to 5 wt %, Persea gratissima (avocado) oil in an amount ranging from about 0.05 to 5 wt %, Aloe barbadensis leaf juice in an amount ranging from about 0.05 to 5 wt %, citric acid in an amount ranging from about 0.05 to 5 wt %, sodium gluconate in an amount ranging from about 0.05 to 5 wt %, sodium hyaluronate (L) in an amount ranging from about 0.01 to 5 wt %, Althaea officinalis (marshmallow) root extract in an amount ranging from about 0.01 to 5 wt %, O-cymen-5-OL in an amount ranging from about 0.01 to 5 wt %, glucose (D) in an amount ranging from about 0.01 to 5 wt %, sodium chloride in an amount ranging from about 0.001 to 5 wt %, sodium citrate in an amount ranging from about 0.001 to 5 wt %, sodium acetate in an amount ranging from about 0.001 to 5 wt %, sodium bicarbonate in an amount ranging from about 0.001 to 5 wt %, tocopheryl acetate (D-alpha) in an amount ranging from about 0.001 to 5 wt %, potassium phosphate in an amount ranging from about 0.001 to 5 wt %, potassium chloride in an amount ranging from about 0.001 to 5 wt %, and/or magnesium chloride in an amount ranging from about 0.001 to 5 wt %.

In some embodiments, the water is present in an amount of about 92.72 wt %, polyacrylate crosspolymer-6 is present in an amount of about 1.3 wt %, Lonicera japonica (honeysuckle) flower extract is present in an amount of about 1.2 wt %, glycerin is present in an amount of about 1.2 wt %, niacinamide is present in an amount of about 1 wt %, Lonicera caprifolium (honeysuckle) flower extract is present in an amount of about 0.5%, Persea gratissima (avocado) oil is present in an amount of about 0.5 wt %, Aloe barbadensis leaf juice is present in an amount of about 0.5 wt %, citric acid is present in an amount of about 0.3 wt %, sodium gluconate is present in an amount of about 0.2 wt %, sodium hyaluronate (L) is present in an amount of about 0.2 wt %, Althaea officinalis (marshmallow) root extract is present in an amount of about 0.1 wt %, O-cymen-5-OL is present in an amount of about 0.1 wt %, glucose (D) is present in an amount of about 0.1 wt %, sodium chloride is present in an amount of about 0.01 wt %, sodium citrate is present in an amount of about 0.01 wt %, sodium acetate is present in an amount of about 0.01 wt %, sodium bicarbonate is present in an amount of about 0.01 wt %, tocopheryl acetate (D-alpha) is present in an amount of about 0.01 wt %, potassium phosphate is present in an amount of about 0.01 wt %, potassium chloride is present in an amount of about 0.01 wt %, and/or magnesium chloride is present in an amount of about 0.01 wt %.

In some embodiments, the base compositions further include a biologic, wherein the biologic is platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof. In some embodiments, the base compositions further include PRP and a second biologic, wherein the second biologic is fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof. In some embodiments, the biologic or the second biologic is a lyophilized powder. In some embodiments, the base composition prolongs or enhances stability of the biologic and prolongs or enhances stability of components of the biologic. In some embodiments, the biologic or the second biologic is PRP, and wherein the components of the biologic or the second biologic includes growth factors, proteins, or nucleic acids. In some embodiments, the base composition inhibits or prevents activation of the biologic or the second biologic, or wherein the base composition maintains, prolongs, preserves, or sustains activity of the biologic or the second biologic or of already active components of the biologic or the second biologic.

Some embodiments provided herein relate to a topical formulation that includes a base composition according to any of the base compositions described herein and a biologic. In some embodiments, the biologic is platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof. In some embodiments, the formulation is formulated as a cream, lotion, salve, paste, serum, gel, ointment, liquid, solution, spray, aerosol, or foam.

Some embodiments provided herein relate to methods of making a topical formulation. In some embodiments, the methods include mixing a biologic with a base composition according to any of the base compositions described herein. In some embodiments, the base composition maintains activity of the biologic for a period of 30, 45, 60, 75, 90 105, or 120 days, or longer. In some embodiments, the biologic is a serum or a powder. In some embodiments, the biologic is a lyophilized powder, and wherein the biologic powder is stable for at least 24 months. In some embodiments, the formulation is formulated for topical application to an area of skin having skin damage, and wherein the formulation improves appearance of the skin. In some embodiments, the formulation is formulated for use in combination with a skin obstruction device. In some embodiments, the skin obstruction device includes electroporation, radiofrequency, ultrasound, high intensity focused ultrasound, needling, intense pulsed light (IPL), ablative laser, non-ablative laser, microdermabrasion, hydradermabrasion, iontophoresis, chemical peel, plasma, high velocity air, high velocity aqueous solution, or combinations thereof. In some embodiments, the biologic includes platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof, or combinations thereof.

Some embodiments provided herein relate to a method of diminishing pore size, diminishing bacteria damage, diminishing red areas, reducing skin damage caused by sun, and maintaining or improving skin tone in a subject in need thereof. In some embodiments the methods include obtaining whole blood from a subject having an area of skin damage, centrifuging the blood to separate platelet rich plasma from platelet poor plasma and red blood cells, collecting the platelet rich plasma (PRP), adding a base composition according to any of the base compositions provided herein to the PRP to form PRP admixed solution thereby forming a first topical formulation, providing the first topical formulation for application to the subject for treatment of the area of skin damage, and providing a second topical formulation for application to the subject over the area of skin damage that has received the first topical formulation. In some embodiments, the second topical formulation activates the platelet rich plasma. In some embodiments, the base composition maintains activity of the PRP for a period of time ranging from at least 30 to at least 120 days. In some embodiments, the second formulation is a gel, liquid, cream, foam, or lotion. In some embodiments, the second formulation is a liquid and wherein the liquid is applied as a spray such as from an aerosol spray or pump spray. In some embodiments, the second formulation includes a platelet rich plasma activator. In some embodiments, the second formulation includes calcium chloride, thrombin, autologous thrombin, bovine thrombin, collagen, calcium, magnesium, sodium, components of snake venom, batroxobin, or combinations thereof. In some embodiments, the subject suffers from skin damage and signs of aging caused by smoking, alcohol, diet, extreme temperatures, chemicals, stress, lack of sleep, poor diet, poor immune system or a combination thereof. In some embodiments, the subject suffers from a skin disorder, a nail disorder, or hair loss. In some embodiments, the skin disorder causes skin damage and signs of aging. In some embodiments, the skin disorder is selected from a group consisting of stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof. In some embodiments, the subject has wrinkles, acne scars, reduced skin elasticity, sagging skin, increased skin dryness, rashes, redness, translucency, fine lines, loss of radiance, increase in the dullness of skin, uneven pigmentation, discoloration, blotchiness, scarring, rough and leathery appearance, freckles, moles, actinic keratosis, slower wound healing, easy bruising and tearing, ruddiness, uneven texture, fine lines, age spots, or a combination thereof. In some embodiments, treating, preventing, or delaying hair loss includes hair restoration or maintenance of hair health. In some embodiments, the base composition is a serum, lotion, liquid primer, cream, gel or a combination thereof. In some embodiments, the base composition further includes at least one keratolytic agent, at least one anti-inflammatory agent, sun protection agent, preservative for platelets in the platelet rich plasma, nutrient, at least one botanical or a combination thereof. In some embodiments, the activating step further includes degranulating platelets in the platelet rich plasma of the first topical formulation and releasing growth factors from the platelets into and through the skin of the subject. In some embodiments, the method further includes performing skin obstruction of the skin over the area of skin damage. In some embodiments, the skin obstruction includes electroporation, radiofrequency, ultrasound, high intensity focused ultrasound, needling, intense pulsed light (IPL), ablative laser, non-ablative laser, microdermabrasion, hydradermabrasion, iontophoresis, chemical peel, plasma, high velocity air, high velocity aqueous solution, or combinations thereof.

Some embodiments provided herein relate to a kit for preparing a base composition. In some embodiments, the kit includes a first vessel including lyophilized biologic powder and a second vessel containing a base composition according to any base compositions described herein. In some embodiments, the kit further includes a dissolution solution for dissolving or solubilizing the lyophilized biologic powder in the first vessel. In some embodiments, the biologic is platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof, or combinations thereof. In some embodiments, the dissolution solution includes water, an aqueous solution, saline, sodium chloride, or phosphate buffered saline. In some embodiments, the kit further includes an activator formulation. In some embodiments, the activator formulation includes calcium chloride, thrombin, autologous thrombin, bovine thrombin, collagen, calcium, magnesium, sodium, components of snake venom, batroxobin, or combinations thereof. In some embodiments, the activator formulation is formulated as a spray.

In some embodiments, a first formulation is applied to or administered to a subject, for example by topical application. Thus, in some embodiments, the first formulation including a base composition and a biologic is formulated as a topical cosmetic base, a gel, a lotion, an ointment, a spray, an aerosol, a powder, a solution, a liquid, a foam, a salve, a paste, a serum, or a cream or combination thereof. In some embodiments, the first formulation is applied by spraying, rubbing, massaging, spreading, coating, or otherwise topically applying to a subject.

Some embodiments provided herein relate to applying a second formulation to the subject following application of the first formulation, thereby activating the first formulation, or activating the biologic in the first formulation, such as by activating the PRP of the first formulation. In some embodiments, the second formulation includes an activator, such as, for example, calcium chloride, autologous thrombin, batroxobin, bovine thrombin, collagen, or other activator of the specific biologic within the first formulation.

Some embodiments provided herein relate to the use of a biologic, such as PRP, taken from a subject suffering from a disorder, such as a skin disorder, nail disorder, or hair loss. These cells can be activated and further formulations may be administered to ensure the survival of the cells. Activation can also lead to degranulation, allowing growth factors to be released into and through the skin to enhance the healing of a skin disorder or nail disorder, for hair restoration or maintenance, or for preventing signs of aging in skin. In some embodiments, the biologic, such as PRP, is taken from a subject that is not suffering from a disorder, and is used to prevent or delay the onset of a disorder, such as a skin disorder, nail disorder, or hair loss.

Some embodiments provided herein relate to methods of treating skin on a subject suffering from skin damage and/or signs of aging is provided. The method includes obtaining whole blood from a subject having skin damage, centrifuging the blood to separate platelet rich plasma from platelet poor plasma and red blood cells, collecting the platelet rich plasma (PRP), adding a base composition, wherein the base composition preserves, extends the life of, enhances, maintains, sustains, or otherwise prolongs the PRP for a period of more than 30, 40, 50, 60, 70, 80, 90, 100, or 120 days. In some embodiments, the base composition is a topical cosmetic base, a gel, a serum, a lotion, an ointment, a spray, an aerosol, a powder, a solution, a liquid, a foam, a salve, a paste, or a cream or combination thereof. In some embodiments, the base composition is added to the platelet rich plasma to form platelet rich plasma admixed solution thereby forming a first topical formulation. In some embodiments, the method includes providing the first topical formulation to the subject for treatment of the skin damage for a 90 day time period. In some embodiments, the PRP is preserved, extended, enhanced, maintained, sustained, or otherwise prolonged due to the base composition for a period of more than 30, 40, 50, 60, 70, 80, 90, 100, or 120 days, such that the first topical formulation may be used having functional PRP at a time period of more than 30, 40, 50, 60, 70, 80, 90, 100, or 120 days after being prepared.

In some embodiments, the providing includes instructions for the subject to topically apply the first topical formulation to an area of the skin and skin damage 1, 2, 3 or 4 times a day, for up to 30, 60, 90 or 120 days or any number of days in between a range defined by any two aforementioned values, and activating the platelet rich plasma. In some embodiments, the activating includes providing a second topical formulation to the subject. In some embodiments, the providing includes applying the second topical formulation over the area of the skin and skin damage that has received the first topical formulation. In some embodiments, treating the skin damage and signs of aging is selected from diminishing pore size, diminishing bacteria damage, diminishing red areas, reducing skin damage caused by sun, and maintaining or improving skin tone.

In some embodiments, the second formulation is a gel, liquid, cream or lotion. In some embodiments, the second formulation is a liquid and wherein the liquid is applied as a spray such as an aerosol spray or pump spray. In some embodiments, the second formulation includes a platelet rich plasma activator. In some embodiments, the second formulation includes calcium, magnesium, sodium, components of snake venom or combinations thereof. In some embodiments, the component of snake venom includes Batroxobin. The calcium may be provided as calcium chloride or calcium carbonate, for example. In some embodiments, the second formulation further includes Batroxobin, epinephrine and/or thrombin. In some embodiments, wherein the second formulation is provided as a spray, the second formulation includes Aqua (Water), a platelet activator, Polysorbate 80, Propylene Glycol, Sodium Chloride, Anthemis Nobilis (Chamomile) Flower Oil, Rosa Canina (Rose Hip) Fruit Oil, *Thymus Vulgaris* (Thyme) Flower/Leaf Oil, Althaea Officinalis (Marshmallow) Root Extract, Hamamelis Virginiana (Witch Hazel) Water, Alcohol, Glycerin, Ethylhexylglycerin, Citric Acid, Potassium Sorbate, Phenoxyethanol, or combinations thereof. In some embodiments, the platelet activator is calcium chloride.

In some embodiments, the subject is also suffering from a skin disorder. In some embodiments, the skin damage and signs of aging are caused by the skin disorder. In some embodiments, the skin damage and signs of aging are caused by smoking, alcohol, diet, extreme temperatures, chemicals, stress, lack of sleep, poor diet, poor immune system or a combination thereof.

In some embodiments, the skin disorder is selected from a group consisting of stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof.

In some embodiments, the subject has wrinkles, acne scars, reduced skin elasticity, sagging skin, increased skin dryness, rashes, redness, translucency, fine lines, loss of radiance, increase in the dullness of skin, uneven pigmentation, discoloration, blotchiness, scarring, rough and leathery appearance, freckles, moles, actinic keratosis, slower wound healing, easy bruising and tearing, ruddiness, uneven texture, fine lines, age spots, or a combination thereof.

In some embodiments, the subject is suffering from hair loss or hair damage. In some embodiments, the subject is not suffering from hair loss or hair damage. The compositions described herein may be used for preventing hair loss, hair restoration, the slowing of hair loss, or for maintenance of hair health. The compositions provided herein may be provided to an area of hair loss, or to slow hair loss, or to the hair for hair maintenance in the form of a salve, a spray, a shampoo, a conditioner, a hair follicle spray, a serum, an injectable composition, or any other formulations suitable for application to hair.

In some embodiments, the topical cosmetic base is a gel, a serum, a lotion, an ointment, a spray, an aerosol, a powder, a solution, a liquid, a foam, a salve, a paste, or a cream, or a combination thereof. In some embodiments, the topical cosmetic base further includes at least one keratolytic agent, at least one anti-inflammatory agent, sun protection agent, preservative for platelets in the platelet rich plasma, nutrient or a combination thereof.

In some embodiments, the activating step further includes degranulating platelets in the platelet rich plasma of the first topical formulation and releasing growth factors from the platelets into and through the skin of the subject.

In a second aspect, a method of treating a subject suffering from skin damage and signs of aging is provided. The method includes obtaining fibroblast skin cells from skin of a subject, placing the fibroblast skin cells in growth media, growing the fibroblast skin cells up to confluency; mixing the fibroblast cells with a topical cosmetic base, thereby making a first formulation including fibroblast cells and applying the formulation to the skin of the subject.

In some embodiments, the subject is also suffering from a skin disorder. In some embodiments, the skin damage and signs of aging are caused by the skin disorder. In some embodiments, the skin damage and signs of aging are caused by smoking, alcohol, diet, extreme temperatures, chemicals, stress, lack of sleep, poor diet, poor immune system or a combination thereof. In some embodiments, the skin disorder is selected from a group consisting of stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof.

In some embodiments, the subject has wrinkles, acne scars, reduced skin elasticity, sagging skin, increased skin dryness, rashes, redness, translucency, fine lines, loss of radiance, increase in the dullness of skin, uneven pigmentation, discoloration, blotchiness, scarring, rough and leathery appearance, freckles, moles, actinic keratosis, slower wound healing, easy bruising and tearing, ruddiness, uneven texture, fine lines, age spots, or a combination thereof.

In some embodiments, the topical cosmetic base is a serum, lotion, liquid primer, cream, gel, or liquid or a combination thereof. In some embodiments, the topical cosmetic base further includes at least one keratolytic agent, at least one anti-inflammatory agent, sun protection agent, or a combination thereof.

In some embodiments, the fibroblast cells are obtained from the skin on the neck, arms, legs, buttocks, stomach, back or behind the ear of the subject.

In some embodiments, the method further includes freezing the fibroblast cells and storing the fibroblast cells prior to mixing fibroblast cells with the topical cosmetic base.

In some embodiments, the method further including thawing the fibroblast cells prior to mixing the fibroblast cells with the topical cosmetic base.

In some embodiments, the growth media includes human platelet lysate, platelet rich plasma, human serum or a combination thereof In some embodiments, wherein growth media includes human platelet lysate and wherein the human platelet lysate is from the subject, the human platelet lysate is obtained by obtaining blood from the subject, centrifuging the blood to separate platelet-poor plasma, platelet rich plasma and collecting the platelet rich plasma.

In some embodiments, the method further includes subjecting the platelet rich plasma to freeze thaw cycles, thereby forming human platelet lysate.

In some embodiments, the method further includes adding and mixing the platelet rich plasma, human platelet lysate or a combination thereof, with growth media, prior to placing the fibroblast skin cells in the growth media.

In some embodiments, the method further includes activating platelets in the platelet rich plasma. The method includes providing a second formulation to the subject, wherein the providing includes applying the second topical formulation over the area of the skin and skin damage that has received the first topical formulation. In some embodiments, the activating includes degranulating platelets in the platelet rich plasma of the first topical formulation and releasing growth factors from the platelets into the skin of the subject.

In some embodiments, the second formulation is a gel, liquid, cream or lotion. In some embodiments, the second formulation is a liquid wherein the liquid is applied as a spray such as an aerosol spray or pump spray. In some embodiments, wherein the second formulation is provided as a spray, the second formulation includes Aqua (Water), a platelet activator, Polysorbate 80, Propylene Glycol, Sodium Chloride, Anthemis Nobilis (Chamomile) Flower Oil, Rosa Canina (Rose Hip) Fruit Oil, *Thymus vulgaris*(Thyme) Flower/Leaf Oil, Althaea Officinalis (Marshmallow) Root Extract, Hamamelis Virginiana (Witch Hazel) Water, Alcohol, Glycerin, Ethylhexylglycerin, Citric Acid, Potassium Sorbate, Phenoxyethanol, or combinations thereof. In some embodiments, the platelet activator is calcium chloride.

In some embodiments, the second formulation includes a platelet rich plasma activator.

In some embodiments, the platelet rich plasma activator is selected from the group consisting of calcium, magnesium, sodium, components of snake venom, thrombin, collagen, or combinations thereof. The calcium may be provided as calcium chloride or calcium carbonate, for example. In some embodiments, the second formulation further includes Batroxobin, epinephrine and/or thrombin. In some embodiments, the second formulation includes 10% calcium (e.g. calcium ion, calcium chloride calcium carbonate, calcium gluconate). In some embodiments, the second formulation includes 15%-20% ethanol, 1:4 ratio autologous thrombin to PRP, 10% calcium chloride w/10,000 units of bovine thrombin, batroxobin, chitosan, or any combination thereof.

In a third aspect, a kit for treating, preventing, or delaying a skin disorder, a nail disorder, hair loss, or signs of aging is provided. The kit includes, for example, a first formulation having a topical cosmetic base, gel, serum, and cream or combination thereof, wherein the first formulation is admixed with platelet rich plasma, and wherein the first formulation further includes nutrients, botanicals, preservatives or skin penetrators or a combination thereof; and a spray bottle or aerosol container holding a second formulation, the second formulation including a platelet rich plasma activator in liquid suspension. In some embodiments, the second formulation includes calcium, magnesium, sodium, components of snake venom or combinations thereof. In some embodiments, the component of snake venom includes Batroxobin. In some embodiments, the second formulation includes 10% calcium (e.g. calcium ion, calcium chloride calcium carbonate, calcium gluconate). In some embodiments, the second formulation includes 15%-20% ethanol, 1:4 ratio autologous thrombin to PRP, 10% calcium chloride w/10,000 units of bovine thrombin, batroxobin, chitosan, or any combination thereof. In some embodiments, the second formulation includes calcium, magnesium, sodium, components of snake venom or combinations thereof. The calcium may be provided as calcium chloride or calcium carbonate, for example. In some embodiments, the second formulation further includes Batroxobin, epinephrine and/or thrombin.

In some embodiments, the second formulation includes 10% calcium (e.g. calcium ion, calcium chloride calcium carbonate, calcium gluconate). In some embodiments, the second formulation includes 15%-20% ethanol, 1:4 ratio autologous thrombin to PRP, 10% calcium chloride w/10,000 units of bovine thrombin, batroxobin, chitosan, or any combination thereof.

In any of the embodiments provided herein, the base composition in the first formulation includes aqua (water), Lonicera japonica (honeysuckle) flower extract, glycerin, niacinamide, polyacrylate crosspolymer-6, Lonicera caprifolium (honeysuckle) flower extract, Persea gratissima (avocado) oil, Aloe barbadensis leaf juice, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, Rosmarinus officinalis (rosemary) leaf oil, *Thymus vulgaris* (thyme) flower/leaf oil, benzyl alcohol, caprylyl glycol, caprylhydroxamic acid, or combinations thereof, and any of the aforementioned components are present in an amount from about 0.001 wt % to about 99% wt %, including 0.001, 0.002, 0.003, 0.004, 0.005, 0.01, 0.02, 0.03, 0.04, 0.05, 0.1, 0.2, 0.3, 0.4, 0.5, 1, 2, 3, 4, 5, 10, 15, 20, 25, 30, 35, 40, 45, 50, 55, 60, 65, 70, 75, 80, 85, 90, 95, 96, 97, 98, or 99%, or an amount within a range defined by any two of the aforementioned values.

In any of the embodiments of the methods, systems, or compositions, the topical formulations or base compositions are formulated for cosmetic usage. In some embodiments, the cosmetic usage includes topical application to skin, for treatment, prevention, or delay of a skin disorder, nail disorder, hair loss, or other skin or hair disorder.

In any of the embodiments provided herein, the compositions are provided to a subject together with, or in conjunction with, a skin obstruction device, such as electroporation, radiofrequency, ultrasound, high intensity focused ultrasound (HIFU), intense pulsed light (IPL), ablative laser, non-ablative laser, microdermabrasion, hydradermabrasion, iontophoresis, chemical peel, plasma, high velocity air, high velocity aqueous solution, or needling, or a combination thereof. In some embodiments, the first formulation is applied to a subject, followed by skin obstruction of the skin. In some embodiments, application of a composition followed by skin obstruction improves update of the composition.

Some embodiments provided herein relate to a base composition for prolonging, preserving, or maintaining a biologic. In some embodiments, the composition includes a cell culture reagent, a buffering agent, a viscosity modifying agent, a thymol, and an anti-microbial. In some embodiments, the composition further includes a humectant and magnesium chloride. In some embodiments, the biological agent is sodium bicarbonate. In some embodiments, the buffering agent preserves the biologic at about or above physiological pH. In some embodiments, the thymol is a thymol isomer, a cresol or O-cymen-5-ol. In some embodiments, the anti-microbial is one or more of Lonicera caprifolium (honeysuckle) flower extract and Lonicera japonica (honeysuckle) flower extract. In some embodiments, the viscosity modifying agent is potassium chloride, sodium chloride, or both. In some embodiments, the cell culture reagent is fetal bovine serum (FBS) or a growth medium. In some embodiments, the humectant is glucose. In some embodiments, the composition includes water, glycerin, niacinamide, polyacrylate crosspolymer-6, Lonicera caprifolium (honeysuckle) flower extract, Lonicera japonica (honeysuckle) flower extract Persea gratissima (avocado) oil, Aloe barbadensis leaf juice, citric acid, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, Rosmarinus officinalis (rosemary) leaf oil, *Thymus vulgaris* (thyme) flower/leaf oil, benzyl alcohol, caprylyl glycol, caprylhydroxamic acid, or combinations thereof. In some embodiments, the composition includes water present in an amount of about 92.72 wt %, polyacrylate crosspolymer-6 present in an amount of about 1.3 wt %, Lonicera japonica (honeysuckle) flower extract present in an amount of about 1.2 wt %, glycerin present in an amount of about 1.2 wt %, niacinamide present in an amount of about 1 wt %, Lonicera caprifolium (honeysuckle) flower extract present in an amount of about 0.5%, Persea gratissima (avocado) oil present in an amount of about 0.5 wt %, Aloe barbadensis leaf juice present in an amount of about 0.5 wt %, citric acid present in an amount of about 0.3 wt %, sodium gluconate present in an amount of about 0.2 wt %, sodium hyaluronate (L) present in an amount of about 0.2 wt %, Althaea officinalis (marshmallow) root extract present in an amount of about 0.1 wt %, O-cymen-5-OL present in an amount of about 0.1 wt %, glucose (D) present in an amount of about 0.1 wt %, sodium chloride present in an amount of about 0.01 wt %, sodium citrate present in an amount of about 0.01 wt %, sodium acetate present in an amount of about 0.01 wt %, sodium bicarbonate present in an amount of about 0.01 wt %, tocopheryl acetate (D-alpha) present in an amount of about 0.01 wt %, potassium phosphate present in an amount of about 0.01 wt %, potassium chloride present in an amount of about 0.01 wt %, and/or magnesium chloride present in an amount of about 0.01 wt %. In some embodiments, the composition further includes a biologic. In some embodiments, the biologic is platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof. In some embodiments, the biologic is a lyophilized powder. In some embodiments, the base composition prolongs or enhances stability of the biologic and prolongs or enhances stability of components of the biologic. In some embodiments, the base composition inhibits or prevents activation of the biologic, or wherein the base composition maintains, prolongs, preserves, or sustains activity of the biologic r of already active components of the biologic. In some embodiments, the base composition is formulated for cosmetic usage, wherein the cosmetic usage includes topical application to skin.

Some embodiment provided herein relate to a topical formulation that includes a base composition as provided herein, including a cell culture reagent, a buffering agent, a viscosity modifying agent, a thymol, and an anti-microbial and a biologic. In some embodiments, the biologic is platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof. In some embodiments, the formulation is formulated as a cream, lotion, salve, paste, serum, gel, ointment, liquid, solution, spray, aerosol, or foam. In some embodiments, the topical formulation is formulated for cosmetic usage, wherein the cosmetic usage includes topical application to skin.

Some embodiments provided herein relate to a method of diminishing pore size, diminishing bacteria damage, diminishing red areas, reducing skin damage caused by sun, and maintaining or improving skin tone in a subject in need thereof. In some embodiments, the method includes obtaining whole blood from a subject having an area of skin damage, centrifuging the blood to separate platelet rich plasma from platelet poor plasma and red blood cells, collecting the platelet rich plasma (PRP), and adding a base composition as disclosed herein to the PRP to form PRP admixed solution, wherein the base composition includes a cell culture reagent, a buffering agent, a viscosity modifying agent, a thymol, and an anti-microbial, thereby forming a first topical formulation, and providing the first topical formulation for application to the subject for treatment of the area of skin damage. In some embodiments, the first topical formulation is stored at a temperature of less than about 10° C., and application of the first topical formulation, such as application to a subject (including application to the face of a subject) increases the temperature of the first topical formulation to at least room temperature. In some embodiments, the increased temperature of the formulation resulting from application to a subject activates the PRP.

In some embodiments, the method further includes providing a second topical formulation for application to the subject over the area of skin damage that has received the first topical formulation, wherein the second topical formulation activates the platelet rich plasma. In some embodiments, the base composition maintains activity of the PRP for a period of time ranging from 30 to 120 days. In some embodiments, the subject suffers from skin damage and signs of aging caused by smoking, alcohol, diet, extreme temperatures, chemicals, stress, lack of sleep, poor diet, poor immune system or a combination thereof. In some embodiments, the subject is also suffering from a skin disorder. In some embodiments, the skin disorder causes skin damage and signs of aging. In some embodiments, the skin disorder is selected from a group consisting of stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof. In some embodiments, the subject has wrinkles, acne scars, reduced skin elasticity, sagging skin, increased skin dryness, rashes, redness, translucency, fine lines, loss of radiance, increase in the dullness of skin, uneven pigmentation, discoloration, blotchiness, scarring, rough and leathery appearance, freckles, moles, actinic keratosis, slower wound healing, easy bruising and tearing, ruddiness, uneven texture, fine lines, age spots, or a combination thereof. In some embodiments, the subject is suffering from hair loss or a hair disorder. In some embodiments, the activating step further includes degranulating platelets in the platelet rich plasma of the first topical formulation and releasing growth factors from the platelets into and through the skin of the subject. In some embodiments, the method further includes performing skin obstruction of the skin over the area of skin damage. In some embodiments, the skin obstruction includes electroporation, radiofrequency, ultrasound, high intensity focused ultrasound, needling, intense pulsed light (IPL), ablative laser, non-ablative laser, microdermabrasion, hydradermabrasion, iontophoresis, chemical peel, plasma, high velocity air, high velocity aqueous solution, or combinations thereof.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In order to describe the manner in which the above-recited and other advantages and features of the invention can be obtained, a more particular description will be rendered by reference to specific embodiments thereof which are illustrated in the appended drawings. Understanding that these drawings depict only typical embodiments and are not therefore to be considered to be limiting of its scope, the invention will be described and explained with additional specificity and detail through the use of the accompanying drawings in which:

FIG. 1A depicts micrographs showing histopathology for the presence of rete pegs in control (top) compared to treatment (bottom). FIG. 1B graphically shows a quantitative measure of rete peg presence in the control and treatment groups as a measure of stratum basale/stratum ganulosum ratio.

DETAILED DESCRIPTION

Figure 1A:
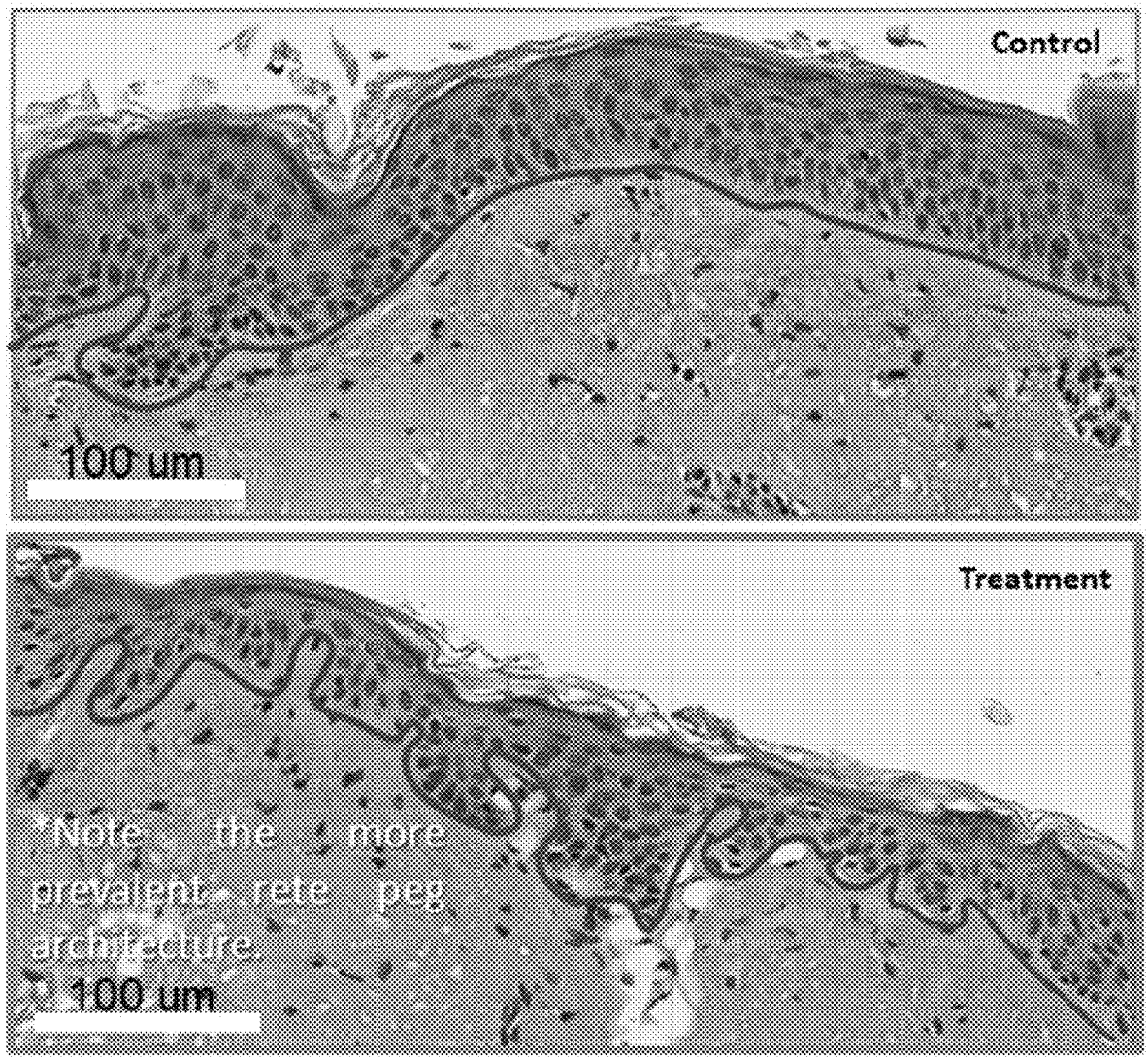
FIGS. 1A-1B depict qualitative improvement of rete peg in skin treated with compositions, some of which include platelet rich plasma (PRP).

In the description that follows, the terms should be given their plain and ordinary meaning when read in light of the specification.

"About" as used herein when referring to a measurable value is meant to encompass variations of ±20% or ±10%, more preferably ±5%, even more preferably ±1%, and still more preferably ±0.1% from the specified value.

"Human platelet lysate" (HPL) has its plain and ordinary meaning when read in light of the specification, and includes, for example, a substitute supplement for fetal bovine serum in a cell culture. In some embodiments described herein, cells used for treatment are grown in culture that is supplemented with HPL.

HPL can be manufactured by a variety of means that are known to those skilled in the art. HPL can be created from single or pooled donor-donated platelets isolated from whole blood or by apheresis, distributed in a standard platelet collection bag. There are some differences between HPL manufacturing protocols, but all can share the same step of being frozen at very low temperatures and thawed. This process can be repeated two or three times to cause complete platelet lysis. The resultant HPL can then undergo different manufacturing steps to achieve multiple grades of HPL.

A common form of HPL undergoes few processing steps, producing a product made of the supernatant following the freeze/thaw process. The included clotting factors required to add heparin to the cell culture media to prevent coagulation during incubation.

Another form of HPL is one that can be used in cell culture without the need of heparin, or any anticoagulant, addition. This grade of HPL goes through further manufacturing steps to inhibit the effect the clotting factors have.

Many labs around the world are creating small amounts of HPL to suit their laboratory needs. Large-scale manufacturing by pooling many platelet donors can be used to mitigate the donor-to-donor variability. Consistency is a top priority for experimental designs to provide reproducible results.

Human platelet lysate is commonly used for supplementation of basal media in mesenchymal stem cells culture. Prior the use, the pathogen inactivation process is recommended to prevent pathogen transmission.

Furthermore, commercially available human platelet lysate can be used, for example, such as HPL prepared commercially by Mill Creek Life Sciences, Compass Biomedical, Inc., Cook Regentec, Macopharama SA, iBiologics, PL bioscience GmbH and Trinova Biochem GmbH. Product lines can include but are not limited to PLTMax, PLUS™, Stemulate, Human Platelet Lysate, XcytePlus, PL$_{SOLUTION}$, PL$_{MATRIX}$ and CRUX RUFA Media supplements.

PLUS™ human platelet lysate which is commercially available has been used in some embodiments described herein. The PLUS™ human platelet lysate is a growth factor rich product manufactured by lysing human platelets. The base composition can be used as cell culture supplement and the lyophilized product has applications in wound healing.

The product, PLUS™ human platelet lysate, is started from raw material which is expired transfusion platelets sourced from FDA-registered and ISO-registered blood banks. The raw material inventories, which are the platelets from the blood banks, are then selected for the production initiation, in which the units are identified for thawing. The thawed pool of platelets are then pooled and transferred into a large transfer bag for serum conversion. The material is then further centrifuged and pooled in a large container for distribution into bottles or cry bags. The raw material is then tested for Human Immunodeficiency Virus I/II, Human T-Lymphotropic Virus, Hepatitis B Virus, Hepatitis C Virus, Syphilis, West Nile Virus and Trypanosoma cruzi. Testing is carried out in a CLIA certified test laboratory. After testing, the raw material is then manufactured through a GMP closed-loop production system for making of the final product, which is a liquid supplement for cell culture, lyophilized product for wound healing applications. The final product is then tested for bacterial & fungal contamination, endotoxin, mycoplasma, MSC expansion, pH, osmolality, hemoglobin, total protein and blood chemistry. The material is filter sterilized. If the material is to be made into a lyophilized powder, the base composition is then sterile lyophilized. The full GMP manufacturing system is in place with incoming product inspection, employee training, SOPs, record keeping and quality control.

The final product as a base composition is available as a research product for cell culture supplementation, in which it is provided in cryo-bags and bottles. A certificate of Analysis is always included with all products.

The final product as a lyophilized powder has minimal change in activity upon lyophilization/reconstitution and is stable at room temperature. The powder can be reconstituted in various solutions and gels (water, PPP, alginate). Currently, the powder is being testing for advanced wound healing applications.

The final product of PLUS™ human platelet lysate has several features and benefits for its use. For example, the human derived, growth factor rich, serum or powder supplement can support in vitro propagation of MSCs, keratinocytes, fibroblasts and other cell types. As such, the PLUS™ human platelet lysate has all the benefits of PRP without the inconvenience of needles and blood draws. Furthermore, the platelets have been sourced from FDA-registered blood banks, so that rigorous serology testing and infectious disease screenings have already been performed. Additionally the large-scale GMP manufacturing has already been established. There are over 100 donor platelet units pooled for each lot, there is consistent product with minimal lot-to-lot variation, and each lot has been tested for MSC expansion, total protein content, pH and several other parameters.

The PLUS™ human platelet lysate is considered very safe to use. The material sourced for the product has come from donors who have been stringently screened and tested for infectious diseases. The platelets are then collected and frozen immediately after a five day expiration. Other safety features include manufacturing the product within a fully closed loop system to prevent exposure to sources of potential contamination and then there is an additional rigorous testing of the final product to ensure that there are no bacterial and fungal contaminations, endotoxins and mycoplasma.

PLUS™ human platelet lysate has several deliverable options. It can be delivered as a cell culture supplement (GMP Plus™), as Plus™ lyophilized in individual packages for reconstitution with platelet poor plasma (PPP), as Plus™ lyophilized and shipped in bulk volumes of 500 mL to 1 L, or as a kit with lyophilized GMP Plus™ in 10 mL sterile glass vial with a crimp seal, vial adapter and a syringe. The prices for the supplements depending on volume and product can range from $275 to $845 (for example, 250 mL of GMP Plus™ Cell Culture Supplement). For the lyophilized packages, the kits can come with the instructions for the reconstitution into a liquid formula. The typical lot sizes for GMP Plus™ are 20 liters although custom lots can be made for up to 50 liters. For consistency in lab tests, lot reservations can be made and delivery for orders for up to 10 liters are immediate.

In some embodiments, a system, method, composition, or kit is provided for preparation of a first topical formulation. In some embodiments, a user obtains a sample of whole blood from the user himself, such that a biologic that is subsequently obtained is autologous. In some embodiments, the user processes the whole blood to obtain a biologic. In some embodiments, the biologic is purified and submitted to lyophilization to obtain a lyophilized biologic powder. Lyophilization techniques can include, for example, freeze drying, vacuum lyophilization, or other lyophilization techniques. In some embodiments, the lyophilized biologic powder is weighed and aliquoted in specific amounts in separate vessels, and stored for later usage. In some embodiments, the lyophilized biologic is dissolved by adding to the vessel a dissolution solution, which may include any aqueous solution capable of dissolving or solubilizing the lyophilized powder. For example, a dissolution solution may include water, sodium chloride, phosphate buffered saline, saline, a buffer, a salt solution, or any other solubilizing agent, thereby generating a biologic dissolved in solution. In some embodiments, the biologic solution is then added to a base composition as described herein, such that the base composition preserves, extends, prolongs, maintains, or sustains the biologic. In some embodiments, the base composition preserves, extends, prolongs, maintains, or sustains components of biologics, such as growth factors, proteins, nucleic acids, or other biomolecules associated with the biologic. In some embodiments, the base composition preserves the biologic in the solution for a period of 30, 45, 60, 75, 90, 105, or 120 days, or longer, such that the biologic formulation exhibits therapeutically effective results when applied on the skin of the subject over a treatment period. In some embodiments, upon complete usage of the biologic formulation, or after a period of time wherein the biologic or the components thereof are no longer viable, a second aliquot of lyophilized biologic powder may be dissolved and combined with the base composition. In some embodiments, the lyophilized PRP powder remains stable for a period of longer than 3, 4, 5, 6, 7, 8, 9, 10, 11, 12, 13, 14, 15, 16, 17, 18, 19, 20, 22, 24, 26, 28, or 30 months.

The human platelet lysate can be formed from but not limited to platelet rich plasma (PRP), pooled platelets from humans and cultured megakaryocytes from stem cell expansion technology. In some embodiments described herein, HPL is from a commercial source. In some embodiments described herein, the human platelet lysate is prepared in the laboratory from platelet rich plasma (PRP), pooled platelets from humans or cultured megakaryocytes from stem cell expansion technology.

In some embodiments herein, the platelet rich plasma and the human platelet lysate can be drawn from the subject that is in need of treatment, prevention, or delay of a skin disorder, nail disorder, or hair disorder and then used to treat the subject themselves. Thus, the subject can be the source of their own products and their own treatments.

Platelets are composed of a cytoskeleton and intracellular structures such as glycogen, lysosomes, and two granules, the dense granule and the alpha-granule. The dense granule comprises adenosine diphosphate (ADP), adenosine triphosphate (ATP), serotonin, and calcium, while the alpha-granule comprises clotting factors, growth factors, and proteins. Embodiments of the present disclosure include compositions capable of maintaining the enclosed cellular components active for extended time periods and obtaining platelets in sufficient quantity to be considered platelet rich plasma.

The normal platelet count in human blood is 150,000-350,000/microliter. "Platelet rich plasma" (PRP) has its plain and ordinary meaning when read in light of the specification, and includes, for example, a blood plasma that has been enriched with platelets. PRP is a component of blood (plasma) with concentrations of platelets above normal values. Thus, PRP refers to a sample having a platelet count of greater than 350,000 platelets per microliter, such as 350,000, 400,000, 450,000, 500,000, 550,000, 600,000, 650,000, 700,000, 750,000, 800,000, 850,000, 900,000, 950,000 or greater than 1,000,000 platelets per microliter, or in an amount within a range defined by any two of the aforementioned values. PRP may further include an amount of platelets greater than a normal platelet count with a full complement of clotting factors. Seven key growth factors may be present in PRP, including, for example, platelet derived growth factors (PDGFaa, PDGFbb, PDGFab), transforming growth factors (TGF-b 1, TGFb2), vascular endothelial growth factor (VEGF), and epithelial growth factor (EGF). These growth factors are found within a normal clot composed of fibrin, fibronectin, and vitronectin, which are cell adhesion molecules required for cell migration, as seen in wound healing. Cellular mitogenesis and angiogenesis are both upregulated by PRP, making it useful in facial rejuvenation.

After injury, platelets are on the front line of the healing response and play a critical role by releasing growth factors. These growth factors influence tissue repair in a variety of different cell types including tendon, muscle and cartilage cells. PRP was first used in dental and oral surgery to improve soft tissue healing in the 1990s. Its usage in the treatment of musculoskeletal injuries and sports medicine has increased over the past decade. PRP has been used as an injectable material for enhanced healing, hair growth, or for facial rejuvenation.

In some embodiments, autologous PRP is obtained from freshly drawn blood from a patient with an added anticoagulant and the sample then undergoes a series of two centrifugation (spin) steps. The first spin, known as the hard spin, separates the red blood cells from the plasma containing the platelets, white blood cells, and clotting factors. Three layers result from the hard spin: an upper layer containing platelets and white blood cells, a middle layer known as the buffy coat containing white blood cells, and a bottom layer containing red blood cells. The red blood cell layer is removed and discarded. The second spin, known as the soft spin, separates the platelet rich plasma in the bottom of the tube from the platelet poor plasma (PPP) in the top of the tube by removing more red blood cells. Proper preparation and centrifuge technique is critical to obtaining high quality active PRP. The literature has pointed to some preparations of PRP having a lack of biological effect which may be due to poor PRP processing or inadequate standard laboratory centrifuges that cannot properly prepare PRP rather than the specialized FDA cleared equipment with validated processes.

As a concentrated source of autologous platelets, PRP contains and releases through several different growth factors and other cytokines that stimulate healing of bone and soft tissue. The components of PRP can include but is not limited to platelet-derived growth factor, transforming growth factor beta, fibroblast growth factor, insulin-like growth factor 1, insulin-like growth factor 2, vascular endothelial growth factor, epidermal growth factor, Interleukin 8, keratinocyte growth factor, and connective tissue growth factor.

PRP can be prepared by collection of the patient's whole blood (that is anticoagulated with citrate dextrose) before undergoing two stages of centrifugation designed to separate the PRP aliquot from platelet-poor plasma and red blood cells. The PRP is denser than the platelet poor plasma and is then collected. In humans, the typical baseline blood platelet count is approximately 200,000 per μL; therapeutic PRP concentrates the platelets by roughly five-fold. The PRP can then be used to prepare human platelet lysate. Typically 20 mL of whole blood may be drawn to generate at least 3 mL of PRP. Typically 60 mL of whole blood may be drawn to generate at least 7 to 10 mL of PRP. In some embodiments, a blood draw for preparing PRP may be in an amount ranging from 1 mL to 60 mL, such as 1, 2, 3, 4, 5, 6, 7, 8, 9, 10, 15, 20, 25, 30, 35, 40, 45, 50, 55, or 60 mL of blood, or in an amount within a range defined by any two of the aforementioned values. As PRP in the embodiments here are originating from the same subject that is treated by the method embodiments herein, the safety concerns are minimal. In some embodiments herein, the platelet rich plasma are from a subject that is being treated for a skin disorder, nail disorder, hair disorder, or signs of aging. In some embodiments, the whole blood is obtained from a subject having skin damage and/or signs of aging, the whole blood is centrifuged to separate platelet rich plasma from platelet poor plasma and red blood cells and the platelet rich plasma (PRP) is collected after centrifugation. The centrifuged blood also has a layer of buffy coat, which is the fraction of anticoagulated blood that contains most of the white blood cells and some platelets. In some embodiments, the platelet rich plasma is used to manufacture platelet lysate. In some embodiments, platelet lysate may be produced by undergoing a freeze and thaw process of the PRP.

Because PRP is autologous, concerns about immune rejection are a non-issue. Growth factors can function by activating a cytoplasmic signal that promotes normal gene expression. PRP can include the same materials present in the blood stream that induce clotting, except in higher concentration. In some embodiments, PRP works through degranulation of the alpha granules in platelets, which contain the growth factors. PRP can be collected in an anticoagulated state for the growth factors to remain active explaining the need to draw the blood into a tube containing sodium citrate. The biologically active cellular components such as the growth factors can be preserved within the platelet when the platelet is held in an inactive state; premature degranulation does not occur and therefore the cellular components are held within the protective enclosure of the platelet. Upon activation of the platelet, the granules can fuse to the cell membrane, the degranulation process, activating the secretory growth factors, which can bind to the transmembrane receptors of target cells, such as mesenchymal stem cells, fibroblasts, endothelial cells, and epidermal cells. This binding can activate intracellular signal proteins that express a gene sequence directing cellular proliferation, collagen synthesis, extracellular matrix formation, and numerous other pathways to promote healing and repair processes. Damaged platelets with degraded or nonviable cellular components can be incapable of inducing this response.

Aging of the skin can be classified into two components: intrinsic and extrinsic aging. As the names imply, intrinsic aging is due to genetically controlled senescence and extrinsic aging is due to environmental factors superimposed on intrinsic aging. Platelet rich plasma (PRP) is obtained from plasma by centrifuging the blood to concentrate the stem cell materials. The PRP can be injected into various skin areas to improve appearance.

"Skin damage" has its plain and ordinary meaning when read in light of the specification, and includes, for example, damage to the skin that can be caused by aging, sun damage, cancer, skin disorder or skin diseases that can cause irritation of the skin. "Without being limiting, the "skin diseases" and/or "skin disorders" can include acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, akin cancer and tropical acne. In some embodiments described herein, a method of treating a subject in need is provided. The subject can have acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, adult male with a large, red, bulbous nose, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, akin cancer and/or tropical acne.

In some embodiments, skin damage is a result of surgery or laser treatment. Thus, in some embodiments, the formulations provided herein are used post-operatively or post-laser treatment to improve compromised skin. Without wishing to be bound by theory, treatment of the skin as described herein may follow a pathway of allowing subcellular components or microparticles to penetrate skin and release microRNAs for improving damaged skin cells. In some embodiments, the PRP formulation in the base composition is applied topically to a subject for treatment of post laser or post-operative procedures to enhancing healing effects, for minimizing scar tissue formation, or for reducing the appearance of scars.

"Hair and scalp disorders" have their plain and ordinary meaning when read in light of the specification, and includes, for example, diseases that affect the hair and skin on the scalp and are also described herein. Diseases that affect hair and scalp can include but are not limited to alopecia, androgenic alopecia, hirsutism, hair shaft disorders, inflammation, acromegaly, eczema, stretch marks (striae), psoriasis, impetigo, atopic dermatitis, darier disease, hair loss, and folliculitis. Top causes for scalp disorders can include but is not limited to acromegaly, atopic dermatitis, darier disease, eczema, fragile X syndrome, impetigo, pachydermoperiostosis, psoriasis and Rosenthal-Kloepfer syndrome. In some embodiments described herein, a method of treating a subject in need is provided. The subject can have a disease affecting the skin and scalp. In some embodiments the subject suffers from alopecia, androgenic alopecia, hirsutism, hair shaft disorders, inflammation, acromegaly, eczema, stretch marks (striae), psoriasis, impetigo, atopic dermatitis, darier disease, and/or folliculitis. In some embodiments, the subject suffers from acromegaly, atopic dermatitis, darier disease, eczema, fragile X syndrome, impetigo, pachydermoperiostosis, psoriasis and/or Rosenthal-Kloepfer syndrome. In some embodiments, the treating includes administering a formulation to the subject in need. In some embodiments, the formulation is within a hair cream, a hair gel, a scalp lotion, a shampoo, conditioner, hair spray or a hair mousse.

"Nail diseases" have their plain and ordinary meaning when read in light of the specification, and includes, for example, disorders or diseases that affect the nail, nail bed, cuticle region and the surrounding skin and are also described herein. Diseases that affect the nail and surrounding skin area such as the cuticle can lead to infection or inflammation that could require medical assistance. Diseases that infect the nail, nail bed and/or cuticle can include but is not limited to onychia, onychocryptosis, onychodystophy, onychogryposis, onycholysis, onychomadesis, onychomycosis, tinea unguium, onychophosis, onychoptosis, onchorrhexis, paronychia, Koilonychia, subungual hematoma, onychomatricoma, nail pemphigus, erythronychia and melanonychia. In some embodiments, the methods provided herein improve fingernail texture. In some embodiments, the methods provided herein improve a nail disorder, a nail disease, or a nail infection. In some embodiments described herein, a method of treating a subject in need is provided. The subject can have a disease affecting the nails, nail bed and/or cuticles. In some embodiments the subject suffers from alopecia, androgenic alopecia, hirsutism, hair shaft disorders, inflammation, acromegaly, eczema, stretch marks (striae), psoriasis, impetigo, atopic dermatitis, darier disease, and/or folliculitis. In some embodiments, the subject suffers from onychia, onchyocryptosis, onychodystophy, onychogryposis, onycholysis, onychomadesis, onychomycosis, tinea unguium, onychophosis, onychoptosis, onchorrhexis, paronychia, Koilonychia, subungual hematoma, onychomatricoma, nail pemphigus, erythronychia and/or melanonychia. In some embodiments, the treating includes administering a formulation to the subject in need. In some embodiments, the formulation is within a skin cream, a lotion or a cuticle cream.

"Inflammation" has its plain and ordinary meaning when read in light of the specification, and includes, for example, a biological response of a body tissue to harmful stimuli. The harmful stimuli can include but is not limited to pathogens, bacteria, viruses, fungi, damaged cells and other irritants that are known to those skilled in the art. Inflammation can be a protective immune response that can involve, for example, immune cells, white blood cells, blood vessels, molecular mediators, and other small molecules. Signs of inflammation can include but is not limited to pain, heat, swelling, and/or loss of function. Inflammation can be acute or chronic. In some embodiments described herein, a formation is provided for the treatment of inflammation. The formulation can include cells manufactured by the methods described herein. In some embodiments, the subject suffers from inflammation. In some embodiments, the inflammation is on the skin of the scalp, and nail area such as the cuticles.

"Tear troughs" have their plain and ordinary meaning when read in light of the specification, and includes, for example, the hollow indentations that are beneath the eye. Tear troughs can also appear due to saggy skin. Saggy skin can be caused by aging, loss of collagen and elastin underneath the skin tissues and sudden weight loss. For cosmetic purposes saggy skin is usually treated around the neck region and facial regions such as the laugh lines, tear troughs and the jaw j owls.

"Micronize" has its plain and ordinary meaning when read in light of the specification, and includes, for example, breaking of a substance into very fine particles, for example, into particles that are only a few microns in diameter. Micronizing can be performed by a micronizer. Examples of several other types of commercial type micronizers for aspirate and organ tissue are known to those skilled in the art. In some embodiments herein, it is contemplated that tissue from the subject may be micronized in order to provide cells or tissue that can be used in the embodiments of the formulations herein.

"Pharmaceutical vehicle" has its plain and ordinary meaning when read in light of the specification, and includes, for example, an inert substance with which a medication is mixed to facilitate measurement and administration of the pharmaceutical formulation. In some embodiments, the pharmaceutical vehicle may allow growth factors from granulation to go through the skin to help heal damaged skin or alleviate the symptoms of a skin disorder.

"Growth media" or "media," has its plain and ordinary meaning when read in light of the specification, and includes, for example, a solid or liquid designed to support the growth of microorganisms or cells. Common growth media for cells, for example, are nutrient broths and agar plates; specialized media are sometimes required for cell culture growth. In the embodiments herein, the media is needed for cell culture growth and expansion. Without being limiting the growth media can be a commercially obtainable growth media that is specialized for eukaryotic cells or mammalian cells. There are several types of media. Without being limiting, this can include, nutrient media, minimal media, selective media, differential media, transport media, and enriched media. The media can be obtained commercially or can easily be manufactured by one with skill in the art. Without being limiting, the cell culture media comprises a carbon source, amino acids, vitamins, minerals, antioxidants, a balanced salt solution, and/or a buffer to maintain a balanced pH in the media during cell growth. Without being limiting, commercially available nutrient media specifically for mammalian cells can be made by ThermoFisher Scientific (DMEM, IMDM, RPMI 1640, MEM, OPti-MEM medium, DMEM/F-12, GluaMax, Advanced media, Recovery freezing medium, F10 Nutrient mixture, Ham's F12 Nutrient mixture, Media 199, Opti-MEM, SensiCell Media for Sensitive cells, BME, Stem cell media (Essential 8™, StemPro™, MSC SFM media)), EMD-Millipore (Cellvento™, Cellvento™ BHK cell culture medium, Cellvento™ CHO cell culture media platform, Customized Cell Culture Media, Classical Cell Culture Media), Fisher Scientific (Corning™ Cellgro™ Minimal Essential Medium Eagle without Glutamine, Corning™ Cellgro™ DMEM with L-glucose and sodium pyruvate), Stemcell™ Technologies (mTESR™ 1, MethoCult™ H4034 Optimim, BrainPhys™), Life Technologies, Invitrogen™ (RPMI 1640 medium) and GE Healthcare (AciCHO P). Cell media for mammalian cells can also be made by those skilled in the art. Without being limiting this can include using recipes for Ham's Medium, which contains all the amino acids, purines and pyrimidines for the synthesis of nucleotides, precursors for synthesizing phospholipids, vitamins, coenzyme lipoic acid, glucose and inorganic ions (sodium, potassium, calcium, copper, zinc and cobalt). The cell media can further be modified with growth factors and proteins. Media can also be optimized for improving cell recovery and activity and/or viability of cells during a freeze-thaw step for the cells. In some embodiments, the media includes preservatives and nutrients to maintain the activity and/or viability or platelet cells and/or fibroblast cells. The term mineral has its ordinary meaning as understood in light of the specification and refers to any mineral. Non limiting examples of minerals include: iodine, manganese, potassium, sodium, selenium, chromium, molybdenum, calcium, phosphorus, zinc, iron, or copper, or any salt form thereof.

"Media Supplements" have their plain and ordinary meaning when read in light of the specification, and includes, for example, elements or a supplement that are used to help mammalian cells produce proteins, and can be used to customize the growth conditions of the cells as provided herein, by improving cell activity and/or viability and maintaining the growth of the cells. Without being limiting, the supplements can include amino acids, 2-mercaptoethanol, lipids, MEM vitamin solutions (commercially made or produced in a laboratory), BSA, human keratinocyte growth supplements, human melanocyte growth supplements, microvascular growth supplements, cholesterol supplements, transferrin, sodium pyruvate and/or vitamins. In some embodiments herein, a method of making a cell for treatment of a subject is provided, the method comprising obtaining cells from the subject, placing cells in growth media, wherein the growth media comprises human platelet lysate and growing the cells up to confluency. In some embodiments, the growth media comprises media supplements.

"Base" has its plain and ordinary meaning when read in light of the specification, and includes, for example, a base for use in a formulation that comprises cells. A base may also be a formulation in which the cells are mixed in. The base may be an emulsion base. In some embodiments, cells or platelet rich plasma is admixed with a base to produce a first formulation that can be applied to the skin.

"Admix" has its plain and ordinary meaning when read in light of the specification, and includes, for example, mixing one product with some other product. In the embodiments herein, cells are admixed with a cosmetic base or formulation. In some embodiments, platelet rich plasma is admixed with a base, such as a cosmetic base or a formulation comprising a pharmaceutical vehicle.

"Maintaining youthful appearance" has its plain and ordinary meaning when read in light of the specification, and includes, for example, decreasing the signs of aging such as fine lines, wrinkles, saggy skin, dullness, for example. This may also indicate that one can prevent further damage and signs of aging.

"Signs of aging" has its plain and ordinary meaning when read in light of the specification, and includes, for example, the appearance of the skin that may occur due to skin damage, exposure, dehydration, aging, illness, chemical treatment, harsh treatment of skin and sun exposure, for example. Signs of aging can include, wrinkles, acne scarring, acne scars, reduced skin elasticity, sagging skin, increased skin dryness, rashes, redness, translucency, fine lines, loss of radiance, increase in the dullness of skin, uneven pigmentation, discoloration, blotchiness, scarring, rough and leathery appearance, freckles, moles, actinic keratosis, slower wound healing, easy bruising and tearing, ruddiness, uneven texture, fine lines, age spots, or a combination thereof.

"Platelet rich activator" has its plain and ordinary meaning when read in light of the specification, and includes, for example, a formulation that allows platelets to degranulate.

"Degranulate" as described herein is a process of losing or releasing granules of a substance. This cellular process allows cytoplasmic granules within the cell to secrete their contents to the outside of the cell. In some embodiments, the biologic contents are then freed from the cell, enabling the biologic contents to penetrate through the skin of a subject, and thereby used as a skin rejuvenation agent. In some embodiments, the platelet rich activator is administered as a lotion, liquid or a gel. In some embodiments, the platelet rich activator is within a liquid, wherein the liquid is administered by a spray onto skin that has been first administered a first formulation comprising adding a topical cosmetic base, gel, serum, and cream or combination thereof and platelet rich plasma. In some embodiments, the first formulation further comprises a topical cosmetic base. In some embodiments, platelet rich activator is within a second formulation, and is administered as a liquid spray. In some embodiments, the platelet rich plasma activator comprises calcium, $CaCl_2$, Calcium carbonate, thrombin, autologous thrombin, bovine thrombin, collagen type I, magnesium, sodium, components of snake venom, or any other agent capable of activating platelets or allowing platelets to degranulate, or combinations thereof. Concentrations of platelet rich activators for use are known to those of skill in the art and can be found in Yuan et al. (Osteoarthritis and Cartilage 21 (2013) 1627e1637), Marx et al (Oral Medicine, Vo., 85, no. 6, June 1998, pp. 638-647), Mazzucco et al. (ISBT Science Series (2007) 2, 272-281), Ehrenfest et al. (Trends in Biotechnology Vol. 27 No. 3, pp. 158-167), and Everts et al. (JECT. 2006; 38:174-187) (all references incorporated in their entireties herein). In some embodiments, the component of snake venom comprises Batroxobin. In some embodiments, the second formulation comprises 10% calcium (e.g. calcium ion, calcium chloride calcium carbonate, calcium gluconate). In some embodiments, the second formulation comprises 15%-20% ethanol, 1:4 ratio autologous thrombin to PRP, 10% calcium chloride w/10,000 units of bovine thrombin, batroxobin, chitosan, or any combination thereof. In some embodiments, wherein the second formulation is provided as a spray, the second formulation comprises Aqua (Water), a platelet activator, Polysorbate 80, Propylene Glycol, Sodium Chloride, Anthemis Nobilis (Chamomile) Flower Oil, Rosa Canina (Rose Hip) Fruit Oil, *Thymus vulgaris* (Thyme) Flower/Leaf Oil, Althaea Officinalis (Marshmallow) Root Extract, Hamamelis Virginiana (Witch Hazel) Water, Alcohol, Glycerin, Ethylhexylglycerin, Citric Acid, Potassium Sorbate, Phenoxyethanol. In some embodiments, the platelet activator is calcium chloride.

"Collagen" has its plain and ordinary meaning when read in light of the specification, and includes, for example, the main structural protein that may be found in the extracellular space in the various connective tissues in animal bodies. In some embodiments, the second formulation which comprises the platelet rich plasma activator comprises collagen.

"Nanopearls" has its plain and ordinary meaning when read in light of the specification, and includes, for example, pharmaceutical lipid nanoparticles to allow nanoemulsions.

"Snake venom" has its plain and ordinary meaning when read in light of the specification, and includes, for example, a highly modified saliva, which contains zootoxins that facilitate the immobilization and the digestion of a snake's prey. The main toxins and proteins in snake venom may have, but is not limited to dehydrogenase lactate, L-amino-acid oxidase, Catalase, Alanine amino transferase, Phospholipase A2, Lysophospholipase, Acetylcholinesterase, Alkaline phosphatase, Acid phosphatase, 5'-Nucleotidase, Phosphodiesterase, Deoxyribonuclease, Ribonuclease 1, Adenosine triphosphatase, Amylase, Hyaluronidase, NAD-Nucleotidase, Kininogenase, Factor-X activator, Heparinase, α-Fibrinogenase, β-Fibrinogenase, Fibrinolytic enzyme, Prothrombin activator, Collagenase, Elastase and Glucosamine ammonium lyase. In some embodiments, the snake venom comprises oxydoreductases, transferases, hydrolases, or lyases or a combination thereof. In some embodiments, the snake venom comprises dehydrogenase lactate, L-amino-acid oxidase, Catalase, Alanine amino transferase, Phospholipase A2, Lysophospholipase, Acetylcholinesterase, Alkaline phosphatase, Acid phosphatase, 5'-Nucleotidase, Phosphodiesterase, Deoxyribonuclease, Ribonuclease 1, Adenosine triphosphatase, Amylase, Hyaluronidase, NAD-Nucleotidase, Kininogenase, Factor-X activator, Heparinase, α-Fibrinogenase, β-Fibrinogenase, Fibrinolytic enzyme, Prothrombin activator, Collagenase, Elastase or Glucosamine ammonium lyase or combinations thereof. In some embodiments, the snake venom comprises α-neurotoxins, β-neurotoxins, κ-Toxins, Dendrotoxins, Cardiotoxins, Myotoxins, Sarafotoxins or Hemorrhagins, or combinations thereof. In some embodiments the snake venom comprises α-Bungarotoxin, α-toxin, erabutoxin, cobratoxin, Notexin, ammodytoxin, β-Bungarotoxin, crotoxin, taipoxin, κ-Toxin, Dendrotoxin, toxins I and K, y-Toxin, cardiotoxin, cytotoxin, Myotoxin-a, crotamine, Sarafotoxin a, Sarafotoxin b, Sarafotoxin c, Phospholipase A2, mucrotoxin A, hemorrhagic toxins, HT1 or HT2 or combinations thereof. In some embodiments, the component of snake venom comprises Batroxobin.

In some embodiments, the compositions described herein relate to a base composition that preserves, extends the life of, enhances, maintains, sustains, or otherwise prolongs a biologic, such as a cell, a protein, an antibody, blood, serum, plasma, or components thereof, or other biological extracts. In some embodiments, the biologic comprises platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof, or combinations thereof. In some embodiments, the base composition is mixed with or combined with a biologic to form a first formulation. In some embodiments, the first formulation preserves, extends the life of, enhances, maintains, sustains, or otherwise prolongs a biologic, for example, for a period of more than 5, 10, 15, 20, 30, 40, 50, 60, 70, 80, 90 or 120 days, or an amount of days within a range defined by any two of the aforementioned values. In some embodiments, the second formulation causes degranulation of the platelets in the first formulation to allow growth factors and biomolecules from the granules to be released into and through the skin to promote healing of a skin disorder and to prevent or treat signs of aging.

In some embodiments, the base composition preserves, extends the life of, enhances, maintains, sustains, or otherwise prolongs components of a biologic. A component of a biologic may include, for example, growth factors, proteins, nucleic acids, or other biomolecules that are associated with, excreted from, or derived from a biologic.

Numerous challenges present for preserving and maintaining platelet rich plasma (PRP) for purposes of preparing a product. Among these challenges is the difficulty of platelet preservation, growth factor preservation, and transdermal drug delivery. In product development phases, developers focus on platelet preservation/growth factor preservation with the use of platelet additive solutions (PAS) to inhibit platelet activation and prolong growth factor degradation. Prior research suggests that the use of platelet specific components may correspond to at least 18 to 20 days of PRP storage and preservation at 22° C. Furthermore, 21-day old platelets are as proliferative in growth factor activity as two-day old platelets, which suggests that expired liquid preserved platelets can still house growth factors in the alpha granule after expiration. These teachings suggest that platelets may be viable for 18 to 20 days, and after expiration may still house the growth factors for at least 21 additional days, such that growth factor activity may remain for at least 39 days. Once the growth factors are in solution, protein degradation takes another two to three weeks, resulting in a total product shelf life of 53 days. Embodiments provided herein prolong the ability to preserve platelet and growth factors, thereby improving product development and longevity, and significantly enhancing product use.

"Botanicals" have their plain and ordinary meaning when read in light of the specification, and includes, for example, substances obtained from a plant and used as an additive. Botanical substances may be extracted from plants or plant parts thereof (for example, flowers, seeds, leaves and roots). Some botanical substances may have antioxidants. In some embodiments, botanicals are selected from a group consisting of Aloe Barbadensis Leaf Juice, Persea Gratissima (Avocado) Oil, Rosmarinus Officinalis (Rosemary) Leaf Oil, Rosa Canina (Rose Hip) Fruit Oil, Butyrospermum Parkii (Shea) Butter, Paeonia Albiflora (Peony) Root Extract, Phenyl t-Butylnitrone (Spin Trap), Camellia Sinensis (White Tea) Leaf Extract, Lavandula Angustifolia (Lavender) Oil, Santalum Austrocaledonicum (Sandalwood) Wood Oil and Hamamelis Virginiana (Witch Hazel).

Accordingly, embodiments provided herein relate to a composition that maintains or that is capable of maintaining a biologic, such as platelet rich plasma (PRP), or a component thereof, fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof.

As used herein, the term "maintain" refers to an ability of a compound or agent to preserve, extend the life of, enhance, sustain, or otherwise prolong a biologic over a given period of time in the compositions described herein. Maintain does not necessarily refer to complete maintenance, but may include partial maintenance, such as maintenance of less than 100% of the biologic over a period of time. For example, maintain may include maintenance of an amount of at least 10%, at least 20%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, or at least 99% maintenance of the biologic over a period of time. The period of time may range in length from at least 1 day to at least 500 days, for example, 1, 2, 3, 4, 5, 6, 7, 14, 21, 28, 30, 60, 90, 120, 150, 180, 210, 240, 270, 300, 330, 360, 365, 400, 450, or 500 days, or for a period of time within a range defined by any two of the aforementioned periods of time.

In some embodiments, the base composition includes a cell nutrient; a biological buffer; a viscosity modifying agent; a thymol; and an anti-microbial. As used herein, a cell nutrient includes, for example fetal bovine serum (FBS), glucose, human platelet lysate, bovine serum albumin, fibroblast growth supplement, vitamins, trace elements, amniotic cell culture supplements, or lipo-polysaccharides, or other cell supplements that are used to maintain a cell (such as a fibroblast), a cell fragment (such as a platelet), or intracellular or extracellular components thereof (such as cytokines within a cell or cell fragment). As used herein, a biological buffer includes, for example, any buffer of sodium, potassium, magnesium, calcium, alpha hydroxy acid, beta hydroxy acid, polyhydroxy acid, hyaluronic acid, and/or carboxylic acid, or a cell culture buffering agent, or a derivative or any combination thereof. In some embodiments, the biological buffer is sodium bicarbonate, sodium gluconate, sodium chloride, sodium citrate, sodium acetate, potassium phosphate, potassium chloride, and/or magnesium chloride. In some embodiments, the biological buffer preserves the biologic at about or above physiological pH. In some embodiments, the biological buffer comprises a cosmetic pH adjuster, including, for example, sodium hydroxide, citric acid, acetic acid, ascorbic acid, benzoic acid, malic acid, formic acid, fumaric acid, hydrochloric acid, glycolic acid, lactic acid, magnesium hydroxide, maleic acid, malonic acid, nitric acid, sodium carbonate, azelaic acid, glucosamine, glycinate, propane derivative, proponal, sodium phosphate, sulfuric acid, triethanolamine, ammonium, lithium hydroxide, magnesium carbonate, oxalic acid, phosphoric acid, tartaric acid, glyoxylic acid, imidazole, lactobionic acid, dibenzothiophene, glutaric acid, guanidine carbonate, galacturonic acid, calcium hydroxide, succinic acid, strontium hydroxide, or derivatives thereof, or any combination thereof.

In some embodiments, the biological buffer includes a cell culture buffer, including, for example, MES (2-(N-Morpholino)ethanesulfonic acid, 4-Morpholineethanesulfonic acid), BIS-TRIS, ADA (N-(2-Acetamido)iminodiacetic acid), PIPES (Piperazine-N,N'-bis(2-ethanesulfonic acid), ACES, MOPSO (3-morpholinopropanesulfonic acid), BES (N,N-bis[2-hydroxyethyl]-2-aminoethanesulfonic acid), MOPS (3-Morpholinopropane-1-sulfonic acid, 3-(N-Morpholino)propanesulfonic acid and 3-Morpholinopropanesulfonic acid), TES (2-[[1,3-dihydroxy-2-(hydroxymethyl)propan-2-yl]amino]ethanesulfonic acid), HEPES (4-(2-hydroxyethyl)-1-piperazineethanesulfonic acid)), DIPSO (3-(N,N-Bis[2-hydroxyethyl]amino)-2-hydroxypropanesulfonic acid, N,N-Bis(2-hydroxyethyl)-3-amino-2-hydroxypropanesulfonic acid), TRIS base, Tricine (N-[Tris(hydroxymethyl)methyl]glycine), Gly-Gly (Glycyl-glycine), HEPPS (4-(2-Hydroxyethyl)-1-piperazinepropanesulfonic acid, 4-(2-Hydroxyethyl)piperazine-1-propanesulfonic acid, N-(2-Hydroxyethyl)piperazine-N'-(3-propanesulfonic acid)), Bicine (N,N-Bis(2-hydroxyethyl)glycine), TAPS (N-[Tris(hydroxymethyl)methyl]-3-aminopropanesulfonic acid, [(2-Hydroxy-1,1-bis(hydroxymethyl)ethyl)amino]-1-propanesulfonic acid), AMPD (2-Amino-2-methyl-1,3-propanediol, Ammediol), AMPSO (N-(1,1-Dimethyl-2-hydroxyethyl)-3-amino-2-hydroxypropanesulfonic acid), CHES (2-(Cyclohexylamino)ethanesulfonic acid, CAPSO (3-(Cyclohexylamino)-2-hydroxy-1-propanesulfonic acid, CAPSO Free Acid), AMP (β-Aminoisobutyl alcohol, 2-Amino-2-methyl-1-propanol), or CAPS (3-(Cyclohexylamino)-1-propanesulfonic acid), or any derivative thereof, or any combination thereof.

A base composition for preserving, extending the life of, enhancing, sustaining, maintaining, or otherwise prolonging a biologic as provided herein may include a cell culture reagent, a buffering agent, a viscosity modifying agent, a thymol, or an anti-microbial agent, or any combination thereof.

As used herein, a cell culture reagent may include any culture reagent that is capable of maintaining a composition that includes biological substances, and can include any media as disclosed herein, including, for example, DMEM, IMDM, RPMI 1640, MEM, OPti-MEM medium, DMEM/F-12, GluaMax, Advanced media, Recovery freezing medium, F10 Nutrient mixture, Ham's F12 Nutrient mixture, Media 199, Opti-MEM, SensiCell Media for Sensitive cells, BME, Stem cell media (Essential 8™, StemPro™, MSC SFM media), EMD-Millipore (Cellvento™, Cellvento™ BHK cell culture medium, Cellvento™ CHO cell culture media platform, Customized Cell Culture Media, Classical Cell Culture Media), Fisher Scientific (Corning™ Cellgro™ Minimal Essential Medium Eagle without Glutamine, Corning™ Cellgro™ DMEM with L-glucose and sodium pyruvate), Stemcell™ Technologies (mTESR™ 1, MethoCult™ H4034 Optimim, BrainPhys™), Life Technologies, Invitrogen™ (RPMI 1640 medium) and GE Healthcare (AciCHO P).

As used herein, a thymol refers to 2-isopropyl-5-methylphenol, and is a natural monoterpenoid phenol derivative of cymene, $C_{10}H_{14}O$, isomeric with carvacrol, found in oil of thyme, and extracted from *Thymus vulgaris* (common thyme) and various other kinds of plants as a white crystalline substance of a pleasant aromatic odor and strong antiseptic properties. Thymol may include, for example, a thymol isomer, a cresol, or O-cymen-5-ol.

As used herein, an anti-microbial agent, refers to an agent that has antimicrobial properties. An anti-microbial agent may include, for example, any agent known or discoverable for its ability to kill microbes, including partial or complete antimicrobial properties. An anti-microbial agent may include, for example, one or more of Lonicera caprifolium (honeysuckle) flower extract or Lonicera japonica (honeysuckle) flower extract, or a combination thereof.

In some embodiments, the base composition provided herein includes a cell nutrient, a biological buffer, a viscosity modifying agent, and a botanical extract. As used herein, a botanical extract has its ordinary meaning in light of the specification, and refers to a composition from a plant source (a botanical). A botanical extract can include, for example, an aqueous extract, wherein the botanical extract is obtained by soaking the botanical in a solvent to extract a portion of the botanical into the solvent. In some embodiments, the extract is an alcohol extract, such as a methanolic extract or an ethanolic extract (for example, a botanical extract obtained by extracting with a methanol mixture or with an ethanol mixture). In some embodiments, a botanical extract is an aqueous ferment extract, such that the botanical is soaked in a solvent that includes a fermenting agent, such as a probiotic. In some embodiments, the botanical extract includes a cosmetic compound. In some embodiments, the botanical extract exhibits antimicrobial properties, including antibacterial, antifungal, antiviral, or antiparasitic properties.

In some embodiments, a botanical extract is obtained from *Cocos nucifera* fruit, radish root, Sambucus Nigra fruit, Ribes Nigrum fruit, Populus Tremuloides bark, Wasabia japonica root, Zingiber officinale root, allium sativum bulb, wasabi, honeysuckle, cedar wood, aspen bark, willow bark, Brahmi (Bacopa monnieri) extract, citrus extract Camellia sinensis (green tea), grapes, pomegranate, Echinacea, Centella Asiatica, Elderflower, Irish moss, Mallow, soap bark, Yucca, Clary sage, oregano, thyme, curcumin compounds, resveratrol (polyphenolic compound from grape, berries, etc.) vetivert, chamomile, rosemary, aloe, nettle, Centella asiatica, Ginkgo biloba, betula, witch hazel, green tea, white tea, grape skin, grape seed, resveratrol grapefruit, grapefruit seed, grapefruit peel, citrus fruits (other than grapefruit extract) bilberry, blueberry, Ginkgo biloba, soy isoflavones, soy extract, fermented soy protein, black cohosh, St. John's wort, echinacea, chamomile, rosemary, aloe extract and juice, nettle, coconut fruit, or Centella asiatica, or combinations thereof. The botanical utilized to obtain the botanical extract may be obtained from any of the plant parts including the leaves, pulp, seeds, or stems, fruit and fruit seeds, as well as the whole plant.

As used herein, "probiotics" has its ordinary meaning as understood in light of the specification, and refers to live microorganisms that confer health benefits when consumed. In some embodiments, a probiotic includes *Lactobacillus*, Leuconostoc, Bacillus, Saccharomyces, Pediococcus, Weissella, Bifidobacterium, Streptococcus, Lactococcus, Gluconacetobacter, Zygosaccharomyces, Acetobacter, or Gluconobacter, or any derivative, ferment, or ferment filtrate thereof, or any combination thereof.

In some embodiments, the cosmetic compound includes a salicylate, a phenolic compound, or a phytonutrient. In some embodiments, the salicylate is derived from an aspen bark isolate, willow bark isolate, or other botanical having salicylate.

As used herein, a "phenolic compound" has its ordinary meaning as understood in light of the specification, and refers to a group of small molecules having at least one phenol unit. Phenolic compounds can include, for example, phenolic acids, flavonoids, tannins, coumarins, lignans, quinones, stilbenes, or curcuminoids. Examples of phenolic acids include, for example, hydroxybenzoic acids (including, for example, gallic acid, gentisic acid, 4-hydroxybenzoic acid, protocatechuic acid, β-resorcylic acid, salicylic acid, syringic acid, or vanillic acid) or hydroxycinnamic acids (including, for example, chlorogenic acid, trans-cinnamic acid, caffeic acid, p-coumaric acid, ferulic acid, isoferulic acid, or sinapic acid), or derivatives or analogues thereof. Examples of flavonoids include, for example, flavan-3-ols (including, for example, (+)-catechin, (−)-epicatechin, (−)-gallocatechin gallate, (−)-epigallocatechin gallate, (−)-epicatechin gallate, (−)gallocatechin, or (−)-epigallocatechin), flavonols (including, for example, datiscetin, fisetin, flavonol, galangin, hyperoside, isorhametin, kaempferol, morin, myricetin, myricitrin, quercetagetin, quercetin, quercitrin, robinetin, rutin, or tamarixetin), flavones (including, for example, apigenin, aposide, balcalcin, balcalin, chrysin, chrysoeriol, diosmetin, gardenin A, genkwanin, lueolin, vitexin, isovitexin, sinensetin, tangeretin, or wogonoside), isoflavones (including, for example, biochanin A, daidzein, daidzin, formononetin, genistin, genistein, glycitin, glycitein, or pucrarin), flavanones (including, for example, dihydromyricetin, eriodictyol, hesperetin, hesperidin, neohesperidin, liquiritigenin, liquiritin, naringenin naringin, narinatin, or (+)-taxifolin), or anthocyanidins (including, for example, cyaniding, delphinidin, malvidin, pelargonidin, peonidin, petunidin, or propelargonidin) or analogues or derivatives thereof. Examples of tannins include, for example, hydrolyzable tannins (including, for example, gallotannins or ellagitannins) or condensed tannins (including, for example, proanthocyanidins or leucoanthocyanidins) or analogues or derivatives thereof. Examples of coumarins include, for example, simple coumarins, furanocoumarins, pyranocoumarins, isocoumarins, or analogues or derivatives thereof. Examples of lignans include, for example, lignanolides, cyclolignanolides, bisepoxylignans, neolignans, or analogues or derivatives thereof. Examples of quinones include, for example, anthraquinones, phenanthraquinones, napthoquinones, benzoquinones, or analogues or derivatives thereof. Examples of stilbenes include, for example, isorhapontigenin, oxyresveratrol, piceid, piceatannol, pinostilbene, pterostilbene, resveratrol, or analogues or derivatives thereof. Examples of curcuminoids include, for example, curcumin or ginerol analogues, or analogues or derivatives thereof. Other phenolic compounds may include, for example, chalcone derivatives, isoliquiritigenin, butein, phloretin, phenolic alkaloids, phenolic terpenoids, m-benzotriphenol derivatives, or cresol, or derivatives or analogues thereof. In some embodiments, the phenolic compound is a thymol or analogue or derivative thereof, such as O-cymen-5-ol.

As used herein, "phytonutrient" has its ordinary meaning as understood in light of the specification, and refers to a plant derived substance associated with positive health effects. A phytonutrient may broadly include natural materials having antimicrobial properties, and further exhibit antioxidant and/or anti-inflammatory properties. Phytonutrients may be derived from a variety of botanicals, such as from Sambucu nigra fruit extract, populous termuloides bark extract, ribes nigrum fruit extract, other botanicals. A phytonutrient may include, for example betalain, indole, organosulfide, phenol, terpene, triterpene, carotenoid, curcuminoid, flavonoids, glucosinolate, isothiocyanate, hydroxycinnamic acid, lignan, lipid, stilbene, sulphide, tocopherol, lutein, zeanthin, isoflavone, flavonoid, coumestna, lycopene, ellagic acid, caffeoylquinic acid, hydroxybenzoic acid, hesperetin, flavonol, terpenoid, phthalide, flavonol, allicin quercetin, sulphide, anthocyanin, resveratrol, and anthoxanthin. In some embodiments, the phytonutrient is a pigmented phytonutrient, such as anthocyanin, lutein, zeaxanthin, lycopene, carotenoids, and/or anthoxanthin.

Some embodiments include any combination of the aforementioned botanical extracts with any of the aforementioned probiotics and/or cosmetic compounds. Non-limiting examples of such combinations include, for example; *Lactobacillus* and *Cocos Nucifera* fruit extract; Leuconostoc and Radish root ferment filtrate; *Lactobacillus* ferment; Bacillus ferment and Saccharomyces ferment filtrate; Leuconostoc, radish root ferment filtrate, *Lactobacillus*, and *Cocos nucifera* fruit extract; *Lactobacillus* ferment, *Lactobacillus*, and *Cocos nucifera* fruit extract; and hexylene glycol, caprylyl glycol, Wasabia japonica root extract, Zingiber officinale root extract, and allium sativum bulb extract.

In some embodiments, the base composition includes a cell nutrient, a biological buffer, a polymer, a thymol, and an antimicrobial. As used herein a "polymer" has its ordinary meaning as understood in light of the specification, and refers to a polymeric compound prepared by polymerizing monomers, whether of the same or a different type. The generic term polymer thus embraces the term homopolymer (employed to refer to polymers prepared from only one type of monomer, with the understanding that trace amounts of impurities can be incorporated into the polymer structure), and the term interpolymer, which are polymers prepared by the polymerization of at least two different types of monomers. The generic term interpolymer thus includes copolymers (employed to refer to polymers prepared from two different types of monomers), and polymers prepared from more than two different types of monomers. The term polymer includes trace amounts of impurities, for example catalyst residue, that may be incorporated into and/or within the polymer. In some embodiments, the polymer includes copolymer or a crosspolymer, or a derivative thereof. In some embodiments, the polymer includes an acrylate crosspolymer, an acrylate copolymer, or a silicone crosspolymer, or derivatives thereof, such as polyacrylate crosspolymer-6, dimethicone crosspolymer, hydroxyethyl acrylate/sodium acryloyldimethyl taurate copolymer, or derivatives thereof. In some embodiments, the polymer includes a natural or a synthetic polymer, and may include, for example, starch, xanthan gum, guar gum, carrageenan, alignates, polysaccharids, pectin, gelatin, agar, cellulose, polyacrylate, polyacrylamide, silicone or derivates or analogues thereof.

In some embodiments, a base composition includes a cell nutrient, a biological buffer, a polymer, a thymol, an antimicrobial, a viscosity modifying agent, a phytonutrient, a phenolic compound, a salicylate, a botanical extract, or any combination of any of the aforementioned compounds or agents.

In any of the embodiments described herein, the first and/or second formulation includes a skin conditioning agent, an emulsion stabilizer, a humectant, a chelating agent, a biocide, a buffering agent, a biologic buffering agent, an antioxidant, a pH adjuster, a viscosity modifying agent, a sun protection agent, a cell culture reagent, an enzyme inhibitor, an activation inhibitor, a skin permeability enhancer, a skin delivery system, or a combination thereof.

In some embodiments, the base composition further includes a protein transport inhibitor agent, including, for example, brefeldin A or monensin, or a combination thereof.

In some embodiments, the first and/or second formulation includes a skin conditioning agent. A skin conditioning agent as used herein refers to a substance that is used to maintain, improve, or enhance a skin condition, and may include, for example, water, Lonicera japonica (honeysuckle) flower extract, niacinamide, lonicera caprifolium (honeysuckle) flower extract, persea gratissima (avocado) oil, aloe barbadensis leaf juice, sodium hyaluronate (L), althaea officinalis (marshmallow) root extract, caprylyl methicone, retinyl palmitate, a mixture of palmitoyl tri- and hepta-peptides, ectoin, acetyl glucosamine, panthenol, caprylyl glycol, caffeine, lactic acid/glycolic acid copolymer, allantoin or bisabolol, or combinations thereof.

In some embodiments, the first and/or second formulation includes an emulsion stabilizer. An emulsion stabilizer refers to a compound or mixture of compounds that helps maintain an emulsion. In some embodiments, the emulsion stabilizer includes, for example, polyacrylate crosspolymer-6, an alcohol, cetyl alcohol, stearyl alcohol, acetic acid, carbomer, gum palmitic acid, polyethylene glycol, isostearic acid, stearic acid, or mixtures thereof.

In some embodiments, the first and/or second formulation includes a humectant. A humectant as used herein refers to a compound or mixture of compounds that increase water content of the top layers of skin. A humectant may include, for example, glycerin, glucose (D), polyhydric alcohols such as glycerol, other polyalkylene glycols (e.g., dipropylene glycol, polypropylene glycol, and polyethylene glycol) and derivatives thereof, alkylene polyols and their derivatives, sorbitol, hydroxy sorbitol, hexylene glycol, 1,3-dibutylene glycol, 1,2,6-hexanetriol, ethoxylated glycerol, propoxylated glycerol, sodium hyaluronate, or mixtures thereof.

In some embodiments, the first and/or second formulation includes a chelating agent. A chelating agent refers to a compound or mixture of compounds that stabilize compositions by preventing precipitation by binding to a particular compound. A chelating agent may include, for example, citric acid, sodium gluconate, EDTA (ethylenediamine tetraacetic acid), HEDTA (hydroxyethylenediamine triacetic acid), NTA (nitriolotriacetic acid), DTPA (diethylenetriaminepentaacetic acid), MGDA (methylglycinediacetic acid), HEIDA (2-hydroxyethyliminodiacetic acid), CDTA (trans-cyclohexane-1,2-diaminetetraacetic acid), EGTA (ethylene glycol-bis((3-aminoethyl ether)-N,N,N',N'-tetraacetic acid), EDDA (ethylenediaminediacetic acid), propylene diamine tetraacetic acid (PDTA), ethylene diamine-N,N"-di(hydroxyphenylacetic) acid (EDDHA), ethylene diamine-N,N"-di-(hydroxy-methylphenyl acetic acid (EDDHMA), or sodium, potassium, and/or ammonium salts, or combinations thereof.

In some embodiments, the first and/or second formulation includes a biocide. A biocide is a compound or mixture of compounds for use in formulations that are used to eliminate, remove, reduce, prevent, or protect against harmful or unwanted organismal growth. A biocide may include a cosmetic biocide, and may include, for example, ammonium phenolsulfonate, benzalkonium chloride, benzethonium chloride, cetylpyridinium chloride, chlorophyllin-copper complex, chlorothymol, chloroxylenol, cloflucarban, dichloro-m-xylenol, methylbenzethonium chloride, O-cymen-5-OL, phenol, sodium phenolsulfonate, triclocarban, triclosan, zinc phenolsulfonate, zinc ricinoleate, or mixtures thereof.

In some embodiments, the first and/or second formulation includes a viscosity modifier. A viscosity modifying agent is a compound or mixture of compounds that modifies viscosity of a composition, and may either increase or decrease the viscosity of a formulation, depending on whether it is desirable to have a formulation with increased or decreased viscosity. For example, a viscosity modifying agent can include any substance suitable to achieve a viscosity of about 1 to about 10 centipoise. The viscosity modifier may include, for example, glycerol, glycerol derivatives, ethylene glycol, propylene glycol (dihydroxypropane), polyethylene glycol, water soluble polymer, natural hydrocolloids (and derivatives), Acacia, tragacanth, alginic acid, carrageenan, locust bean gum, guar gum, xanthan gum, gum arabic, gelatin, cellulose, alginates, starches, honeys, hydrogels, chitosans, dextrans, gelatin, sugars (and derivatives), dextrose, fructose, polydextrose, polydextrans, saccharides, polysaccharides, semisynthetic hydrocolloids (and derivatives), methylcellulose, hydroxyethyl starch (hetastarch), sodium carboxymethylcellulose, sodium chloride, potassium chloride, magnesium chloride, hydroxyethylcellulose, hydroxypropylmethylcellulose, polyvinylpyrrolidone (PVP), synthetic hydrocolloids (and derivatives), Polyvinyl alcohol (PVA) or Carbopol® or combinations thereof.

In some embodiments, the first and/or second formulation includes a buffering agent. A buffering agent refers to an agent use to maintain pH of a solution near a chose pH value. Such agents may include acids, bases, or combinations thereof. Buffering agents may include biologic buffering agents, and may include, for example, for example, phosphate salts, boric acids or boric salts, magnesium chloride, potassium chloride, glucose, sodium bicarbonate, sodium chloride, sodium acetate, sodium phosphate, fetal bovine serum (FBS), N-cyclohexyl-2-aminoethanesulfonic acid (CHES) or salts thereof, 3-[[1,3-dihydroxy-2-(hydroxymethyl)propan-2-yl]amino]propane-1-sulfonic acid (TAPS) or salts thereof, 2-(N-morpholino)ethanesulfonic acid (MES) and salts thereof, piperazine-N,N'-bis(2-ethanesulfonic acid (PIPES) and salts thereof, N-(2-acetamido)-2-aminoethanesulfonic acid (ACES) and salts thereof, cholamine chloride, BES, 2-[[1,3-dihydroxy-2-(hydroxymethyl)-propan-2-yl]amino]ethanesulfonic acid (TES) and salts thereof, 2-[4-(2-hydroxyethyl)piperazin-1-yl]ethanesulfonic acid (HEPES) and salts thereof, acetamidoglycine; N-(2-hydroxy-1,1-bis (hydroxyl-methyl)ethyl)glycine (tricine), glycinamide, 2-(bis(2-hydroxyethyl)amino)acetic acid (bicine) and salts thereof, propionate salts, 3-[[1,3-dihydroxy-2-(hydroxymethyl)propan-2-yl]-amino]-2-hydroxy-propane-1-sulfonic acid (TAPSO) and salts thereof, 3-morpholinopropane-1-sulfonic acid (MOPS) and salts thereof, saline-sodium citrate (SSC) buffer, 2-amino-2-hydroxymethyl-propane-1,3-diol (synonyms: TRIS, trisamine, THAM, tromethamine, trometamol, tromethane), citric acid or citrate salts (e.g. sodium citrate), trisodium phosphate, disodium hydrogen phosphate, sodium dihydrogen phosphate, tripotassium phosphate, dipotassium phosphate, monopotassium phosphate and/or any other buffering agent containing phosphate, or combinations thereof.

In some embodiments, the first and/or second formulation includes an antioxidant. An antioxidant refers to a compound or mixture of compounds that inhibit, suppress, or reduce oxidative damage to cells or biomolecules by stabilizing free radicals before they can cause harmful reactions. Antioxidants may include, for example, tocopheryl acetate (D-alpha), vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, vitamin A, vitamin C, vitamin E, ubiquinone, mineral selenium, manganese, melatonin, a-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q 10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC), theaflavin and its gallate forms, thearubigins, isoflavone, phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-a-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or synthetic antioxidant such as butylated hydroxytolune or butylated hydroxyanisole, or combinations thereof.

In some embodiments, the first and/or second formulation includes a pH adjuster. A pH adjuster refers to a compound or mixture of compounds that can change the pH of a composition. Exemplary pH adjusters include acids, bases, buffers, phosphates (such as potassium phosphate) or combinations thereof.

In some embodiments, the first and/or second formulation includes a sun protection agent. A sun protection agent refers to a compound or mixture of compounds that provide protection to skin against damaging effects of the sun. In some embodiments, the sun protection agent provides protection against ultraviolet radiation. A sun protection agent may include, for example, petrolatum, metal oxides, zinc oxide, titanium dioxide, para-aminobenzoic acid, PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate (octinoxate), isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives (e.g., avobenzone), octocrylene, octyl triazone, digalloyl trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidene camphor, isopentyl 4-methoxycinnamate, kaolin, talc, or derivatives or analogues thereof, or combinations thereof.

In some embodiments, the first and/or second formulation includes a cell culture reagent. A cell culture reagent is a compound or mixture of compounds used in cell culture for proliferation, maintenance, or induction of a cell culture. Cell culture reagents may include, for example, cell culture media (including the growth media described herein), cell culture serum, cell culture additives, media supplements, feeder cells, or combinations thereof.

In some embodiments, the first and/or second formulation includes an enzyme inhibitor. An enzyme inhibitor is a compound or mixture of compounds that inhibits or reduces function and/or activity of an enzyme. An inhibitor may prevent a substrate from entering the active site of the enzyme and/or prevent the enzyme from catalyzing a chemical reaction. Enzyme inhibitors may be reversible (non-covalently bound to the enzyme) or irreversible (covalently bound to the enzyme).

In some embodiments, the first and/or second formulation includes an activation inhibitor. An activation inhibitor is a compound or mixture of compounds that prevents or reduces activation of a biologic. A biologic may undergo activation, thereby resulting in subsequent lysis and death. For example, platelet activation results in platelet lysis and death. Activation of a biologic is desired to be controlled, and preferably at the time of or after application of a formulation to a subject. An activation inhibitor is capable of reducing, minimizing, or preventing activation of the biologic during storage or after the formulation is prepared but prior to application of the formulation. In some embodiments, the activation inhibitor prevents activation for a period of greater than 15, 30, 45, 60, 75, 90, 105, or 120 days, or greater. An activation inhibitor may include, for example, an inhibitor or chelator of thrombin, calcium chloride, batroxobin, or collagen.

In some embodiments, the first and/or second formulation includes a skin permeability enhancer. A permeability enhancer increases or enhances an ability of a formulation or compounds within a formulation to penetrate or absorb into skin. A kin permeability enhancer may include, for example, magainin, short synthetic peptide (ACSSSPSKHCG), biotinylated hepta-D-arginine, sulphoxides (such as dimethylsulphoxide, DMSO), Azones (e.g. laurocapram), pyrrolidones (for example 2-pyrrolidone, 2P), alcohols and alkanols (ethanol or decanol), glycols (for example propylene glycol), surfactants, or terpenes, or combinations thereof.

In some embodiments, the first and/or second formulation includes a skin delivery system. A skin delivery system refers to a combination of compounds that enhance delivery of a formulation to skin, and may include, for example, emulsions (such as micro- and nano-encapsulation emulsions), vesicles, liposomes, solid-lipid nanoparticles (SLN), nanostructured lipid carriers (NLC), phytosomes, transferosomes, nanocrystals, cubosomes, or fulvate fraction liposomes, or any combination thereof.

"Foam" has its plain and ordinary meaning when read in light of the specification, and includes, for example, a substance that is formed by trapping pockets of gas in a liquid or solid. In some alternative formulations herein, a formulation is provided as a foam to be absorbed into the skin.

"Batroxobin," has its plain and ordinary meaning when read in light of the specification, and includes, for example, snake venom produced by Bothrops atrox and Bothrops moojeni, venomous species of pit viper. Batroxobin may act as a hemotoxin which acts as a serine protease closely related to thrombin and has been the subject of many medical studies as a replacement of thrombin.

This disclosure provides for a method of treating for a skin disorder or treating signs of again in a subject in need. This disclosure also describes formulations for treating a skin disorder and signs of aging. A kit comprising formulations is also contemplated.

Methods of Treating Skin of a Subject

In some embodiments, a method of preparing a formulation for treatment is provided. A method of making a topical formulation for treatment for a subject is also provided. Previous methods of preparing mammalian cells involve the use of media, wherein the media contains fetal bovine serum. As shown in exemplary embodiments herein, formulations comprising a biologic, such as cells, platelet rich plasma, human platelet lysate or combinations thereof, in combination with a base composition may lead to a surprising increase in the proliferation or longevity of the biologic with a shorter doubling time of cells, which is more cost effective. In some embodiments, the biologic also exhibit an increase in the expression of the protein collagen, which is known to improve the appearance of the skin. Additionally, the increase in proliferation or longevity of the biologic can lead to a larger amount of biologics to be used for treatment and to treat a larger surface area of skin on a subject in need. Human platelet lysate can be prepared for use, which is known to those skilled in the art. Furthermore, commercially available human platelet lysate can be used, for example, such as HPL prepared commercially by Mill Creek Life Sciences, Compass Biomedical, Inc., Cook Regentec, Macopharama SA, iBiologics, PL bioscience GmbH and Trinova Biochem GmbH. Product lines can include but are not limited to PLTMax, PLUS™, Stemulate, Human Platelet Lysate, XcytePlus, $PL_{SOLUTION}$, $PL_{MATRIX}$ and CRUX RUFA Media supplements. Furthermore, platelet rich plasma and platelet lysate may also be prepared from the subject for their own treatment. Activation of the platelets in the platelet rich plasma is also contemplated, as this would allow degranulation or the platelets, allowing growth factors to be released and absorbed into the skin.

Human platelet lysate can also be prepared for use in the embodiments described herein, and their preparation is known to those skilled in the art. The preparation of human platelet lysate is described in Schallmoser et al. (J Vis Exp. 2009 Oct. 30; (32), Fekete et al. (Cytotherapy. 2012 May; 14(5): 540-554) and Shih et al. (New Biotechnology Volume 32, Issue 1, 25 Jan. 2015, Pages 199-211) (each of these references, and all references cited herein, are hereby expressly included by reference in their entireties). Human platelet lysate can also be produced by use of a commercially available platelet lysate preparation kit, such as ones by Macopharma. The human platelet lysate can be comprised from but not limited to platelet rich plasma (PRP), pooled platelets from humans and cultured megakaryocytes from stem cell expansion technology.

As used herein, human platelet lysate can be a substitute supplement for fetal bovine serum in experimental as well as in clinical cell cultures. The human platelet lysate is obtained from human blood platelets after several freeze/thaw cycles, which case the platelets to lyse and release a large quantity of growth factors for cell expansion. In some embodiments, the media in which the cells are growing comprise 1%, 2%, 3%, 4%, 5%, 6%, 7%, 8%, 9%, 10%, 11%, 12%, 13%, 14% or 15% volume/volume human platelet lysate in the medium, or any amount in between any two aforementioned values. In some embodiments, whole blood from a subject having skin damage is obtained and centrifuged. The centrifugation leads to the separation of the blood into fractions of platelet rich plasma from platelet poor plasma and red blood cells. The platelet rich plasma is then separated. The platelet rich plasma may be added to a base composition, wherein the base compositions is a topical cosmetic base, a gel, a serum, a lotion, an ointment, a spray, an aerosol, a powder, a solution, a liquid, a foam, a salve, a paste, or a cream or combination thereof. In some embodiments, the platelet rich plasma is subjected to a freeze thaw cycle to break up the platelets, thus forming platelet lysate.

The first formulation may be stored in a temperature controlled unit, such as a refrigerator, prior to use to preserve the PRP of the formulation. The formulation can be stored in a refrigerator for a period of more than 5, 10, 15, 20, 30, 40, 50, 60, 70, 80, 90 or 120 days, or an amount of days within a range defined by any two of the aforementioned values. The first formulation may be stored at 0, 1, 2, 3, 4, 5, 6, 7, 8, 9, 10, 11, 12, 13, 14, 15, 20, 25, or 30° C., or at a temperature within a range defined by any two of the aforementioned values.

In some embodiments, the first formulation comprises a base composition in which the cells are mixed into thereby producing the first formulation. In some embodiments, the base composition of the first formulation comprises aqua (water), Lonicera japonica (honeysuckle) flower extract, glycerin, niacinamide, polyacrylate crosspolymer-6, Lonicera caprifolium (honeysuckle) flower extract, Persea gratissima (avocado) oil, Aloe barbadensis leaf juice, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, Rosmarinus officinalis (rosemary) leaf oil, *Thymus vulgaris* (thyme) flower/leaf oil, benzyl alcohol, caprylyl glycol, caprylhydroxamic acid, or combinations thereof. In some embodiments, any of the aforementioned components are present in an amount from about 0.001 wt % to about 99% wt %, including 0.001, 0.002, 0.003, 0.004, 0.005, 0.01, 0.02, 0.03, 0.04, 0.05, 0.1, 0.2, 0.3, 0.4, 0.5, 1, 2, 3, 4, 5, 10, 15, 20, 25, 30, 35, 40, 45, 50, 55, 60, 65, 70, 75, 80, 85, 90, 95, 96, 97, 98, or 99%, or an amount within a range defined by any two of the aforementioned values.

In some embodiments, a method of treating skin on a subject suffering from skin damage and/or signs of aging is provided. The method comprises obtaining whole blood from a subject having skin damage, centrifuging the blood to separate platelet rich plasma from platelet poor plasma and red blood cells, collecting the platelet rich plasma (PRP), adding a base composition, wherein the base composition is a topical cosmetic base, a gel, a serum, a lotion, an ointment, a spray, an aerosol, a powder, a solution, a liquid, a foam, a salve, a paste, or a cream or combination thereof to the platelet rich plasma to form platelet rich plasma admixed solution thereby forming a first topical formulation, providing the first topical formulation to the subject for treatment of the skin damage for a 90 day time period, wherein the providing comprises instructions for the subject to topically apply the first topical formulation to an area of the skin and skin damage 1, 2, 3 or 4 times a day, for up to 30, 60, 90 or 120 days or any number of days in between a range defined by any two aforementioned values, activating the platelet rich plasma. In some embodiments, activating the PRP comprises time, chemical, or temperature activation. Time activation may occur, for example, by providing sufficient time for the biologic, such as PRP to be activated. Chemical activation may occur, for example, by providing a chemical that induces activation, such as by the use of a cell stimulation cocktail. A cell stimulation cocktail may include, for example, phorbol 12-myristate 13-acetate (PMA), ionomycin, or other chemical agents. Such chemical agents may include, for example, calcium, $CaCl_2$, Calcium carbonate, thrombin, autologous thrombin, bovine thrombin, collagen type I, magnesium, sodium, components of snake venom, or any other agent capable of activating platelets or allowing platelets to degranulate, or any combinations thereof. Thus, chemical activation may occur, in some embodiments, by providing a second topical formulation having activator agents to the subject. In some embodiments, the providing comprises applying the second topical formulation over the area of the skin and skin damage that has received the first topical formulation, wherein treating the skin damage and signs of aging is selected from the group consisting of diminishing pore size, diminishing bacteria damage, diminishing red areas, reducing skin damage caused by sun, and maintaining or improving skin tone. The first formulation may not be applied to the ears, eyes, mouth area or other body orifices.

Temperature activation may occur, for example, by changing the temperature of the base composition. In some embodiments, a change in temperature induces stress on the biologic, such as on PRP or platelets, thereby degranulating the biologic, resulting in activation of the biologic. Thus, in some embodiments, temperature activation occurs by decreasing the temperature or by increasing the temperature of the base composition. In one embodiment, the base composition is prepared having a biologic, and is stored at refrigeration, such as a temperature of less than about 10° C., such as 10° C., 9° C., 8° C., 7° C., 6° C., 5° C., 4° C., 3° C., 2° C., or 1° C. The refrigerated base composition is stored for a period of time, and is then applied to skin of a subject, such as to a face of a subject. Application of the base composition to the skin of the subject causes the temperature of the base composition to increase from refrigerated temperature to greater than room temperature, whereupon the biologic is activated due to the increase in temperature. In some embodiments, a kit is provided, wherein the kit includes a base composition and a means for refrigeration of the base composition, such as a refrigerator or cooling device. The kit may be used by adding a biologic to the base composition, and placing the composition in the refrigerator or cooling device, where the composition is stored until application. Upon application of the base composition or a portion thereof, the base composition increases in temperature, resulting in activation of the biologic, such as activation of PRP, platelets, or components thereof.

In some embodiments, the methods include use of a temperature differential to activate a biologic, such as activation of PRP, platelets, or components thereof. For example, a volume of the base composition at room temperature may be topically applied to a user, for example to a hand of a user, and mechanical force may be applied to apply the base composition onto the skin. The resulting change in temperature of the base composition, due to the surface temperature of the skin and/or the application of mechanical force, activates the biologic. Without wishing to be limited to mechanistic actions, such activation of a biologic results in release of the biologic contents, enabling the ability of the biologic contents to penetrate skin of the subject, as described herein.

Mechanical activation can include agitation, such as rubbing, massaging, spreading, or otherwise topically applying the compositions. Other means of mechanical force may include use of a mechanical device, such as, for example, microdermabrasion, oscillating fibers (Clarisonic), suction, microneedling, roller, or other mechanical cleansing devices. Mechanical force may also be complemented with ultrasound, radiofrequency, electromagnetic energy, or other sources of radiation to increase temperature of the composition during application to the skin.

In some embodiments, contacting the base composition with the biologic, preserves, extends the life of, enhances, maintains, sustains, or otherwise prolongs the biologic, such as cells, proteins, antibodies, blood, serum, plasma, or components thereof, or other biological extracts.

In some embodiments, the second formulation is a gel, liquid, cream or lotion. In some embodiments, the second formulation is a liquid and wherein the liquid is applied as a spray such as an aerosol spray or pump spray. In some embodiments, the second formulation comprises a platelet rich plasma activator. In some embodiments, the second formulation further includes Batroxobin, epinephrine and/or thrombin. In some embodiments, the second formulation comprises calcium, magnesium, sodium, components of snake venom or combinations thereof. In some embodiments, the snake venom comprises oxydoreductases, transferases, hydrolases, or lyases or a combination thereof. The calcium may be provided as calcium chloride or calcium carbonate, for example. In some embodiments, the snake venom comprises Batroxobin. In some embodiments, the snake venom comprises dehydrogenase lactate, L-aminoacid oxidase, Catalase, Alanine amino transferase, Phospholipase A2, Lysophospholipase, Acetylcholinesterase, Alkaline phosphatase, Acid phosphatase, 5'-Nucleotidase, Phosphodiesterase, Deoxyribonuclease, Ribonuclease 1, Adenosine triphosphatase, Amylase, Hyaluronidase, NAD-Nucleotidase, Kininogenase, Factor-X activator, Heparinase, α-Fibrinogenase, β-Fibrinogenase, Fibrinolytic enzyme, Prothrombin activator, Collagenase, Elastase or Glucosamine ammonium lyase or combinations thereof. In some embodiments, the snake venom comprises α-neurotoxins, β-neurotoxins, κ-Toxins, Dendrotoxins, Cardiotoxins, Myotoxins, Sarafotoxins or Hemorrhagins, or combinations thereof. In some embodiments the snake venom comprises α-Bungarotoxin, α-toxin, erabutoxin, cobratoxin, Notexin, ammodytoxin, β-Bungarotoxin, crotoxin, taipoxin, κ-Toxin, Dendrotoxin, toxins I and K, y-Toxin, cardiotoxin, cytotoxin, Myotoxin-a, crotamine, Sarafotoxin a, Sarafotoxin b, Sarafotoxin c, Phospholipase A2, mucrotoxin A, hemorrhagic toxins, HT1 or HT2 or combinations thereof. In some embodiments, the second formulation further includes Batroxobin, epinephrine and/or thrombin. The second formulation may not be applied to the ears, eyes, mouth area or other orifices. In some embodiments, wherein the second formulation comprises thrombin, the second formulation may not be applied to the ears, eyes, mouth area or other orifices. In some embodiments, wherein the second formulation includes thrombin, the second formulation may not be applied to the ears, eyes, mouth area or other body orifices. In some embodiments, the snake venom comprises Batroxobin. In some embodiments, the second formulation comprises 10% calcium (e.g. calcium ion, calcium chloride calcium carbonate, calcium gluconate). In some embodiments, the second formulation comprises 15%-20% ethanol, 1:4 ratio autologous thrombin to PRP, 10% calcium chloride w/10,000 units of bovine thrombin, batroxobin, chitosan, or any combination thereof.

In some embodiments, the biologic, such as PRP is activated by a change in temperature, such as by an increase or decrease in temperature. For example, in some embodiments, the first topical formulation (the base composition) having a biologic is stored at a refrigerated temperature, such as at a temperature of less than about 10° C., such as at a temperature of 10° C., 9° C., 8° C., 7° C., 6° C., 5° C., 4° C., 3° C., 2° C., or 1° C. Storage of the base composition at low temperature may serve to prevent activation of PRP. Upon application of the base composition to skin of a subject, for example, to the face of the subject, the base composition increases in temperature, for example, to a temperature of greater than 10° C., including to room temperature or to a temperature greater than room temperature, such as body temperature. The increase in temperature may serve to activate PRP, such that the PRP is activated only upon application of the composition to the subject.

In some embodiments, the subject is also suffering from a skin disorder. In some embodiments, the skin damage and signs of aging are caused by the skin disorder. In some embodiments, the skin damage and signs of aging are caused by smoking, alcohol, diet, extreme temperatures, chemicals, stress, lack of sleep, poor diet, poor immune system or a combination thereof. In some embodiments, the skin disorder is selected from a group consisting of stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof. In some embodiments, the subject has wrinkles, acne scars, reduced skin elasticity, sagging skin, increased skin dryness, rashes, redness, translucency, fine lines, loss of radiance, increase in the dullness of skin, uneven pigmentation, discoloration, blotchiness, scarring, rough and leathery appearance, freckles, moles, actinic keratosis, slower wound healing, easy bruising and tearing, ruddiness, uneven texture, fine lines, age spots, or a combination thereof.

In some embodiments, the base composition is a topical cosmetic base is a serum, lotion, liquid primer, cream, gel or a combination thereof. In some embodiments, the base composition further includes at least one keratolytic agent, at least one anti-inflammatory agent, sun protection agent, preservative for platelets in the platelet rich plasma, nutrient or a combination thereof.

In some embodiments, the activating step further includes degranulating platelets in the platelet rich plasma of the first topical formulation and releasing growth factors from the platelets into and through the skin of the subject. The degranulation may lead to release of three major types of secretory granules in platelets, such as lysosomes, alpha and dense granules.

Application of the second formulation may be applied 5, 10, 20, 30, 40, 50, 60, 70, 80, 90 or 120 days after application of the first formulation. In some embodiments, the second formulation may be applied every five days after the first application of the first formulation for up to 120 days. In some embodiments, the first formulation is reapplied to an area of skin that is afflicted with the skin disorder or to an area of skin that is showing signs of aging, and the second formulation is applied over the area 5, 10, 20, 30, 40, 50, 60, 70, 80, 90 or 120 days after application of the first formulation. The second formulation may not be applied to the ears, eyes, mouth area or other body orifices. In some embodiments, wherein the second formulation includes thrombin, the second formulation may not be applied to the ears, eyes, mouth area or other body orifices.

In some embodiments, a method of treating skin on a subject suffering from skin damage and/or signs of aging is provided. The method comprises obtaining whole blood from a subject having skin damage, centrifuging the blood to separate platelet rich plasma from platelet poor plasma and red blood cells, collecting the platelet rich plasma (PRP), —adding a topical cosmetic base, gel, serum, and cream or combination thereof to the platelet rich plasma to form a solution thereby forming a first topical formulation, providing the first topical formulation to the subject for treatment of the skin damage for a 90 day time period wherein the providing includes instructions for the subject to topically apply the first topical formulation to an area of the skin and skin damage multiple times a day, activating the platelet rich plasma, wherein the activating includes providing a second topical formulation to the subject or changing the temperature of the base composition thereby activating the PRP through a temperature change; wherein the providing includes applying the second topical formulation over the area of the skin and skin damage that has received the first topical formulation, wherein treating the skin damage and signs of aging is selected from the group consisting of diminishing pore size, diminishing bacteria damage, diminishing red areas, reducing skin damage caused by sun, and maintaining or improving skin tone. The method further comprises providing topical formulation to the subject comprising of calcium, sodium, or other platelet rich plasma activator to be applied onto base and platelet rich plasma admixed solution. In some embodiments, the first formulation is applied 1, 2, 3 or 4 times a day. In some embodiments, the first formulation is applied for up to 30, 60, 90 or 120 days or any number of days in between a range defined by any two aforementioned values. In some embodiments, the first formulation is applied for up to 90, 120, 150, 200 or 250 days. The first and second formulation may not be applied to the ears, eyes, mouth area or other orifices. In some embodiments, wherein the second formulation includes thrombin, the second formulation may not be applied to the ears, eyes, mouth area or other orifices.

In some embodiments, the second formulation is a gel, liquid, cream or lotion. The second formulation may be applied over the area of skin that has received the first formulation in order to activate the platelets in the first formulation.

In some embodiments, the second formulation is a liquid and wherein the liquid is applied as a spray such as an aerosol spray or pump spray. In some embodiments, the second formulation includes a platelet rich plasma activator. In some embodiments, the second formulation includes calcium, magnesium, sodium, components of snake venom or combinations thereof. In some embodiments, the component of snake venom comprises Batroxobin. In some embodiments, the second formulation further includes Batroxobin, epinephrine and/or thrombin. The calcium may be provided as calcium chloride or calcium carbonate, for example. In some embodiments, the second formulation comprises 10% calcium (e.g. calcium ion, calcium chloride calcium carbonate, calcium gluconate). In some embodiments, the second formulation comprises 15%-20% ethanol, 1:4 ratio autologous thrombin to PRP, 10% calcium chloride w/10,000 units of bovine thrombin, batroxobin, chitosan, or any combination thereof. In some embodiments, wherein the second formulation is provided as a spray, the second formulation comprises Aqua (Water), a platelet activator, Polysorbate 80, Propylene Glycol, Sodium Chloride, Anthemis Nobilis (Chamomile) Flower Oil, Rosa Canina (Rose Hip) Fruit Oil, *Thymus vulgaris*(Thyme) Flower/Leaf Oil, Althaea Officinalis (Marshmallow) Root Extract, Hamamelis Virginiana (Witch Hazel) Water, Alcohol, Glycerin, Ethylhexylglycerin, Citric Acid, Potassium Sorbate, Phenoxyethanol. In some embodiments, the platelet activator is calcium chloride. The second formulation may not be applied to the ears, eyes, mouth area or other body orifices. In some embodiments, wherein the second formulation comprises thrombin, the second formulation may not be applied to the ears, eyes, mouth area or other body orifices.

In some embodiments, the subject is also suffering from a skin disorder. In some embodiments, the skin damage and signs of aging are caused by the skin disorder. In some embodiments, the skin damage and signs of aging are caused by smoking, alcohol, diet, extreme temperatures, chemicals, stress, lack of sleep, poor diet, poor immune system or a combination thereof.

In some embodiments, the skin disorder is selected from a group consisting of stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof.

In some embodiments, the subject has stretch marks, wrinkles, acne scars, reduced skin elasticity, sagging skin, increased skin dryness, rashes, redness, translucency, fine lines, loss of radiance, increase in the dullness of skin, uneven pigmentation, discoloration, blotchiness, scarring, rough and leathery appearance, freckles, moles, actinic keratosis, slower wound healing, easy bruising and tearing, ruddiness, uneven texture, fine lines, age spots, or a combination thereof.

In some embodiments, the base composition is a serum, lotion, liquid primer, cream, gel or a combination thereof.

In some embodiments, the base composition further comprises at least one keratolytic agent, at least one anti-inflammatory agent, sun protection agent, preservative for platelets in the platelet rich plasma, nutrient or a combination thereof.

In some embodiments, the activating step further comprises degranulating platelets in the platelet rich plasma of the first topical formulation and releasing growth factors from the platelets into and through the skin of the subject.

In some embodiments, the second formulation comprises a platelet rich plasma activator. In some embodiments, the second formulation is a liquid, and wherein the liquid is in a spray bottle. In some embodiments, the second formulation comprises calcium, magnesium, sodium, components of snake venom or combinations thereof. In some embodiments, the component of snake venom comprises Batroxobin. The calcium may be provided as calcium chloride or calcium carbonate, for example. In some embodiments, the kit stored at 4° C. to preserve the first and second formulation. In some embodiments, wherein the second formulation does not include snake venom, the kit does not need to be stored in refrigeration. In some embodiments, the second formulation comprises 10% calcium (e.g. calcium ion, calcium chloride calcium carbonate, calcium gluconate). In some embodiments, the second formulation comprises 15%-20% ethanol, 1:4 ratio autologous thrombin to PRP, 10% calcium chloride w/10,000 units of bovine thrombin, batroxobin, chitosan, or any combination thereof. The second formulation may not be applied to the ears, eyes, mouth area or other orifices. In some embodiments, wherein the second formulation comprises thrombin, the second formulation may not be applied to the ears, eyes, mouth area or other orifices.

Application of the second formulation may be applied 5, 10, 20, 30, 40, 50, 60, 70, 80, 90 or 120 days after application of the first formulation. In some embodiments, the second formulation may be applied every five days after the first application of the first formulation for up to 120 days. In some embodiments, the first formulation is reapplied to an area of skin that is afflicted with the skin disorder or to an area of skin that is showing signs of aging, and the second formulation is applied over the area 5, 10, 20, 30, 40, 50, 60, 70, 80, 90 or 120 days after application of the first formulation. The second formulation may not be applied to the ears, eyes, mouth area or other orifices. In some embodiments, wherein the second formulation comprises thrombin, the second formulation may not be applied to the ears, eyes, mouth area or other orifices.

In some embodiments, the method of treating skin further includes subjecting the skin to skin obstruction, such as electroporation, radiofrequency, ultrasound, high intensity focused ultrasound (HIFU), intense pulsed light (IPL), ablative laser, non-ablative laser, microdermabrasion, hydradermabrasion, iontophoresis, chemical peel, plasma, high velocity air, high velocity aqueous solution, or needling, or a combination thereof. In some embodiments, skin obstruction takes place before administration of the first formulation, during administration of the first formulation, after administration of the first formulation but prior to administration of the second formulation, during administration of the second formulation, or after administration of the second formulation. In some embodiments, skin obstruction takes place for a period of time of about 0.5 minutes to 20 minutes, such as 0.5, 1, 2, 3, 4, 5, 6, 7, 8, 9, 10, 11, 12, 13, 14, 15, 16, 17, 18, 19, or 20 minutes, or for an amount of time within a range defined by any two of the aforementioned values. In some embodiments, skin obstruction takes place using a therapeutic skin obstruction device that may be used on skin of a subject. In some embodiments, skin obstruction prior to, concomitantly with, or following application of the formulations generates channels through which the biologic, such as the PRP can penetrate into the viable epidermis and dermis to improve a skin condition.

In any of the methods provided herein, the method may further include providing a low concentration acidic spray to be applied to the composition following topical application of the composition to the subject. In some embodiments, the low concentration acid spray includes low concentrations of hydrochloric acid (HCl), such as hydrochloric acid in an amount ranging from about 0.01% to about 10% HCl, such as 0.01%, 0.05%, 0.1%, 0.5%, 1%, 2%, 3%, 4%, 5%, 6%, 7%, 8%, 9%, or 10%, or in an amount with a range defined by any two of the aforemented values.

Formulations Comprising Fibroblasts

In some embodiments, a method of treating a subject suffering from skin damage and signs of aging is provided. The method comprise obtaining fibroblast skin cells from skin of a subject, placing the fibroblast skin cells in growth media, growing the fibroblast skin cells up to confluency, mixing the fibroblast cells with a base composition wherein the base composition preserves, extends the life of, enhances, maintains, sustains, or otherwise prolongs the cells, thereby making a first formulation comprising fibroblast cells, and applying the formulation to the skin of the subject. In some embodiments, the base composition preserves, extends the life of, enhances, maintains, sustains, or otherwise prolongs the cells for a period of more than 30, 40, 50, 60, 70, 80, 90, 100, or 120 days.

In some embodiments, the subject is also suffering from a skin disorder. In some embodiments, the skin damage and signs of aging are caused by the skin disorder. In some embodiments, the skin damage and signs of aging are caused by smoking, alcohol, diet, extreme temperatures, chemicals, stress, lack of sleep, poor diet, poor immune system or a combination thereof. In some embodiments, the skin disorder is selected from a group consisting of stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof. In some embodiments, the subject has wrinkles, acne scars, reduced skin elasticity, sagging skin, increased skin dryness, rashes, redness, translucency, fine lines, loss of radiance, increase in the dullness of skin, uneven pigmentation, discoloration, blotchiness, scarring, rough and leathery appearance, freckles, moles, actinic keratosis, slower wound healing, easy bruising and tearing, ruddiness, uneven texture, fine lines, age spots, or a combination thereof.

In some embodiments, the base composition is a serum, lotion, liquid primer, cream, gel, or liquid or a combination thereof. In some embodiments, the base composition further comprises at least one keratolytic agent, at least one anti-inflammatory agent, sun protection agent, or a combination thereof.

In some embodiments, the fibroblast cells are obtained from the skin on the neck, arms, legs, buttocks, stomach, back or behind the ear of the subject. In some embodiments, the method further comprises freezing the fibroblast cells and storing the fibroblast cells prior to mixing fibroblast cells with the topical cosmetic base.

In some embodiments, the method further comprising thawing the fibroblast cells prior to mixing the fibroblast cells with the base composition.

In some embodiments, the growth media comprises human platelet lysate, platelet rich plasma, human serum or a combination thereof.

In some embodiments, growth media comprises human platelet lysate and wherein the human platelet lysate is from the subject, wherein the human platelet lysate is obtained by: obtaining blood from the subject, centrifuging the blood to separate platelet-poor plasma, platelet rich plasma; and collecting the platelet rich plasma.

In some embodiments, the method further comprises subjecting the platelet rich plasma to freeze thaw cycles, thereby forming human platelet lysate.

In some embodiments, the method further comprises adding mixing the platelet rich plasma, human platelet lysate or a combination thereof, with growth media, prior to placing the fibroblast skin cells in the growth media.

In some embodiments, the method further comprises activating platelets in the platelet rich plasma. The method comprises providing a second formulation to the subject, wherein the providing comprises applying the second topical formulation over the area of the skin and skin damage that has received the first topical formulation.

In some embodiments, activating platelets in the PRP includes changing the temperature of the first topical formulation from a refrigerated temperature to room temperature, thereby activating the platelets through a change in temperature. In some embodiments, changing the temperature of the first topical formulation includes application of the formulation to a subject, wherein the application increases the temperature of the formulation, thereby activating the platelets.

In some embodiments, the activating comprises degranulating platelets in the platelet rich plasma of the first topical formulation and releasing growth factors from the platelets into the skin of the subject.

In some embodiments, the second formulation is a gel, liquid, cream or lotion. In some embodiments, the second formulation is a liquid and wherein the liquid is applied as a spray such as an aerosol spray or pump spray. In some embodiments, the second formulation comprises a platelet rich plasma activator. In some embodiments, the platelet rich plasma activator calcium, magnesium, sodium, components of snake venom or combinations thereof. In some embodiments, the component of snake venom comprises Batroxobin. The calcium may be provided as calcium chloride or calcium carbonate, for example. In some embodiments, the second formulation comprises calcium, magnesium, sodium, components of snake venom or combinations thereof. In some embodiments, the snake venom comprises oxydoreductases, transferases, hydrolases, or lyases or a combination thereof. In some embodiments, the snake venom comprises dehydrogenase lactate, L-amino-acid oxidase, Catalase, Alanine amino transferase, Phospholipase A2, Lysophospholipase, Acetylcholinesterase, Alkaline phosphatase, Acid phosphatase, 5'-Nucleotidase, Phosphodiesterase, Deoxyribonuclease, Ribonuclease 1, Adenosine triphosphatase, Amylase, Hyaluronidase, NAD-Nucleotidase, Kininogenase, Factor-X activator, Heparinase, α-Fibrinogenase, β-Fibrinogenase, Fibrinolytic enzyme, Prothrombin activator, Collagenase, Elastase or Glucosamine ammonium lyase or combinations thereof. In some embodiments, the snake venom comprises α-neurotoxins, β-neurotoxins, κ-Toxins, Dendrotoxins, Cardiotoxins, Myotoxins, Sarafotoxins or Hemorrhagins, or combinations thereof. In some embodiments the snake venom comprises α-Bungarotoxin, α-toxin, erabutoxin, cobratoxin, Notexin, ammodytoxin, β-Bungarotoxin, crotoxin, taipoxin, κ-Toxin, Dendrotoxin, toxins I and K, y-Toxin, cardiotoxin, cytotoxin, Myotoxin-a, crotamine, Sarafotoxin a, Sarafotoxin b, Sarafotoxin c, Phospholipase A2, mucrotoxin A, hemorrhagic toxins, HT1 or HT2 or combinations thereof. In some embodiments, the second formulation further comprises Batroxobin, epinephrine and/or thrombin. In some embodiments, the snake venom comprises Batroxobin. In some embodiments, the second formulation comprises 10% calcium (e.g. calcium ion, calcium chloride calcium carbonate, calcium gluconate). In some embodiments, the second formulation comprises 15%-20% ethanol, 1:4 ratio autologous thrombin to PRP, 10% calcium chloride w/10,000 units of bovine thrombin, batroxobin, chitosan, or any combination thereof. In some embodiments, wherein the second formulation is provided as a spray, the second formulation comprises Aqua (Water), a platelet activator, Polysorbate 80, Propylene Glycol, Sodium Chloride, Anthemis Nobilis (Chamomile) Flower Oil, Rosa Canina (Rose Hip) Fruit Oil, *Thymus vulgaris*(Thyme) Flower/Leaf Oil, Althaea Officinalis (Marshmallow) Root Extract, Hamamelis Virginiana (Witch Hazel) Water, Alcohol, Glycerin, Ethylhexylglycerin, Citric Acid, Potassium Sorbate, Phenoxyethanol. In some embodiments, the platelet activator is calcium chloride.

In some embodiments, the subject is also suffering from a skin disorder. In some embodiments, the skin damage and signs of aging are caused by the skin disorder. In some embodiments, the skin damage and signs of aging are caused by smoking, alcohol, diet, extreme temperatures, chemicals, stress, lack of sleep, poor diet, poor immune system or a combination thereof. In some embodiments, the skin disorder is selected from a group consisting of stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof. In some embodiments, the subject has wrinkles, acne scars, reduced skin elasticity, sagging skin, increased skin dryness, rashes, redness, translucency, fine lines, loss of radiance, increase in the dullness of skin, uneven pigmentation, discoloration, blotchiness, scarring, rough and leathery appearance, freckles, moles, actinic keratosis, slower wound healing, easy bruising and tearing, ruddiness, uneven texture, fine lines, age spots, or a combination thereof.

In some embodiments, the topical cosmetic base is a serum, lotion, liquid primer, cream, gel or a combination thereof. In some embodiments, the topical cosmetic base further comprises at least one keratolytic agent, at least one anti-inflammatory agent, sun protection agent, preservative for platelets in the platelet rich plasma, nutrient or a combination thereof.

In some embodiments, the activating step further comprises degranulating platelets in the platelet rich plasma of the first topical formulation and releasing growth factors from the platelets into and through the skin of the subject. The degranulation may lead to release of three major types of secretory granules in platelets, such as lysosomes, alpha and dense granules.

Application of the second formulation may be applied 5, 10, 20, 30, 40, 50, 60, 70, 80, 90 or 120 days after application of the first formulation. In some embodiments, the second formulation may be applied every five days after the first application of the first formulation for up to 120 days. In some embodiments, the first formulation is reapplied to an area of skin that is afflicted with the skin disorder or to an area of skin that is showing signs of aging, and the second formulation is applied over the area 5, 10, 20, 30, 40, 50, 60, 70, 80, 90 or 120 days after application of the first formulation.

Advantages of Using the Inactivated First Formulation with the Activation Spray

An advantage of the first formulation is that the first formulation is not activated when first applied, which allows the absorption of the topical formulation into the skin and to the area with skin damage. The second formulation to activate the first formulation is in a liquid. The liquid may be administered as a spray, such as an aerosol spray. After which the spray is applied to activate or degranulate the platelets in the first formulation. The advantage of the spray would be to prevent touching or irritating skin damage, as the formulation applied directly to the affected area could cause additional irritation from rubbing as well as contamination and infection of the skin site. Thus the first formulation is absorbed first without being bound to any theory, this first absorption allows the absorption of the growth factors to be released into and through the skin to enhance the healing of a skin disorder of for preventing signs of aging in skin after the spray comprising the activator is applied. In some embodiments, the first formulation is allowed to absorb prior to applying the second formulation. The first formulation may be applied 1, 2, 3, 4, 5, 6, 7, 8, 9, 10, 11, 12, 13, 14, 15, 16, 17, 18, 19, 20, 21, 22, 23 or 24 hours prior to adding the second formulation. In some embodiments, the waterproof dressing is applied onto the skin after the addition of the first formulation to prevent contamination or to prevent wash off. Depending on the type of damage of the skin, the first formulation is allowed to be absorbed for some time in order to allow penetration of the growth factors that are released during degranulation. For example, if the damage is extended deep into the epidermis or dermis, the first formulation may be allowed to absorb on the skin for at least 24 hours prior to allowing degranulation by applying the second formulation. In some embodiments, the second formulation is applied on top of the first formulation right away to start the activation process of the platelets by the platelet activator. In some embodiments, right away is within a few seconds to 1, 2, 3, 4, 5, 6, 7, 8, 9 or 10 minutes after application of the first formulation. In some embodiments, the first formulation may be applied 1, 2, 3, 4, 5, 6, days or even 1 or 2 weeks prior to administration of the second formulation.

The use of an inactivated first formulation increases the lifespan of the platelets within the PRP and therefore the lifespan of the platelet factors essential for skin rejuvenation because the platelet factors stay dormant within the granules of the cell. The lifespan of the platelet factors is prolonged due to the components of the base composition, which is capable of preserving, extending the life of, enhancing, maintaining, sustaining, or otherwise prolonging the platelets and platelet factors for a period of more than 30, 40, 50, 60, 70, 80, 90, 100, or 120 days. Therefore, activating the first formulation with the second formulation increases the efficacy of first formulation when the platelets of the first formulation remain inactivated.

In some embodiments, the first formulation may also be applied as a spray, to reduce contact with skin damage and to protect against additional irritation from rubbing as well as contamination and infection of the skin site.

Activation of the PRP after the first formulation is on the skin would allow one to regulate the growth factors release and endothelial cell division. During activation or degranulation, platelet derived growth factor, vascular endothelial growth factor (VEGF), transforming growth factor beta (TGF-beta), and interleukin 1 beta levels are released.

In some embodiments, the compositions provided herein preserve, extend the life of, enhance, maintain, sustain, or otherwise prolong the biologic, such as cells, proteins, nucleic acids, growth factors, antibodies, blood, serum, plasma, or components thereof, or other biomolecules. In some embodiments, biomolecules include PDGF, VEG, IGF, TGF-B1, FGF, EGF, CTGF PDGF-A, PDGF-AB, PDGF-B, CTGF, CTAP-3, basic fibroblast GF, TGF-B1, PF4, PDAF, endothelial cell growth inhibitor, EPF, EGI, KGF, ANGPTL6, IGF, IGFBP-3, TGF-B2, Estrogen receptor-related protein, VEGF, f-ECGF, HGF, Histamine-releasing factors, Human collagenase inhibitor, fibronectin, PMP-1, t-PMP, TC1, TC2, Vitronectin, Thrombospondin, Serotonin, Cathepsin, CXCL7, NAP-2, NAP-4, SST, RANTES, CTAP-3, PP14, SCUBE1, CCN family, Annexin 11, HSP27, HSP60, von Willebrand factor, Albumin, Immunoglobulins IgG, IgM, IgA, Coagulation factors V, VII, XI, XIII, Fibrinogen, Histamine, ATP, ADP, GPT, GDP, Collagenase, ADAMTS-13. Superoxide dismutase (SOD), Heparinase, α1-α2 anti/trypsin, α2-antiplasmin, α2-macroglobulin, C1-INH, aldolase, carboxypeptidases, acid phosphatase, arylsulphatase, β-galactoidase, β-glucoronidase, β-glycerolphosphatase, α/β-glucosidases, α/β-fucosidases, α-mannosidase, α-arabinosidase, SIG, JE, KC, inducible BMP-2,-6,-7, Metalloprotease MMP-1,-2,-9,-13, ECM remodeling factors, ERK, PC, LPA, or HMGB1 or a combination thereof. Components released after degranulation is provided in Borzini et al (Borzini, P. and Mazzucco, I., 2007. Platelet-rich plasma (PRP) and platelet derivatives for topical therapy. What is true from the biologic view point? *ISBT Science Series,* 2(1), pp. 272-281; incorporated by reference in its entirety herein.

Advantages of administering the second formulation as a spray also leads to a better coverage of the first layer comprising the first formulation on the skin, thus allowing the all the cells of the first formulation to be degranulated. Providing the second formulation as a spray prevents disturbing the first formulation layer and irritating the cells of the first formulation that is already in the skin. Additionally, a spray may lead to even coverage over the skin allowing an improved efficacy of the two formulations to work together.

First Formulation

In some embodiments, the first formulation comprises a base composition that comprises a humectant, sodium bicarbonate, a buffering agent, magnesium chloride, and a viscosity modifying agent. In some embodiments, the first formulation further includes a skin conditioning agent, an emulsion stabilizer, a chelating agent, a biocide, a biologic buffering agent, an antioxidant, a pH adjuster, a sun protection agent, a cell culture reagent, an enzyme inhibitor, an activation inhibitor, a skin permeability enhancer, a skin delivery system, or a combination thereof. In some embodiments, the base composition comprises aqua (water), Lonicera japonica (honeysuckle) flower extract, glycerin, niacinamide, polyacrylate crosspolymer-6, Lonicera caprifolium (honeysuckle) flower extract, Persea gratissima (avocado) oil, Aloe barbadensis leaf juice, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, Rosmarinus officinalis (rosemary) leaf oil, *Thymus vulgaris* (thyme) flower/leaf oil, benzyl alcohol, caprylyl glycol, caprylhydroxamic acid, or combinations thereof. In some embodiments, any of the aforementioned components are present in an amount from about 0.001 wt % to about 99% wt %, including 0.001, 0.002, 0.003, 0.004, 0.005, 0.01, 0.02, 0.03, 0.04, 0.05, 0.1, 0.2, 0.3, 0.4, 0.5, 1, 2, 3, 4, 5, 10, 15, 20, 25, 30, 35, 40, 45, 50, 55, 60, 65, 70, 75, 80, 85, 90, 95, 96, 97, 98, or 99%, or an amount within a range defined by any two of the aforementioned values. In some embodiments, any of the aforementioned components are present in a composition in a therapeutically effective amount. For example, any of the aforementioned components may be present in the base composition in an amount from about 0.001 mg to about 10 mg, such as 0.001, 0.05, 0.1, 0.5, 1, 2, 3, 4, 5, 6, 7, 8, 9, or 10 mg, or an amount within a range defined by any two of the aforementioned values.

In some embodiments, the first formulation is provided to a subject in need in an amount of about 0.05 mg to about 10 mg, such as 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10 mg, or an amount within a range defined by any two of the aforementioned values. One of skill in the art will recognize that the amount that is provided to a subject will depend on the condition being treated, the severity of the condition, the size or area of the region being treated, or other such considerations, and thus, the amount or quantity of first formulation that is applied to a subject may vary.

Importantly, the base composition is capable of preserving, extending the life of, enhancing, maintaining, sustaining, or otherwise prolonging a biologics with which it is mixed to form the first formulation, such that the biologic has an extended life or activity when mixed with the base composition. In some embodiments, the biologic has an extended life or activity for a period of more than 30, 40, 50, 60, 70, 80, 90, 100, or 120 days, such that the first formulation may be applied or administered to a subject in need many days, weeks, or months after preparation of the formulation. This is in contrast to currently available compositions, which have a short shelf-life due to the inability of the biologic to maintain viability or activity over time. The base composition described herein enables increased longevity and activity due to the specific components and quantities of components provided and described herein.

Following application of a first formulation to a subject in need thereof, the biologic, such as PRP, may be activated by application of the second formulation.

Second Formulation

In some embodiments, the second formulation is provided as a spray, the second formulation comprises aqua (Water), a platelet activator, Polysorbate 80, Propylene Glycol, Sodium Chloride, Anthemis Nobilis (Chamomile) Flower Oil, Rosa Canina (Rose Hip) Fruit Oil, *Thymus vulgaris* (Thyme) Flower/Leaf Oil, Althaea Officinalis (Marshmallow) Root Extract, Hamamelis Virginiana (Witch Hazel) Water, Alcohol, Glycerin, Ethylhexylglycerin, Citric Acid, Potassium Sorbate, Phenoxyethanol. In some embodiments, the platelet activator is calcium chloride.

In some embodiments, the first and/or second formulation comprises skin penetrators, preservatives and/or botanicals. In some embodiments, the skin penetrators include Fulvate fractions (Omni Bioceutical Innovations) liposomes, nanoparticles, dimethylsulfoxide, sodium lauryl sulfate, hyaluronic acid, nanostructured lipid.

In some embodiments of the first or second formulation, the formulation may be provided within a spray or aerosol bottle. Formulation 1 may comprise aqua (water), Lonicera japonica (honeysuckle) flower extract, glycerin, niacinamide, polyacrylate crosspolymer-6, Lonicera caprifolium (honeysuckle) flower extract, Persea gratissima (avocado) oil, Aloe barbadensis leaf juice, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, Rosmarinus officinalis (rosemary) leaf oil, *Thymus vulgaris* (thyme) flower/leaf oil, benzyl alcohol, caprylyl glycol, caprylhydroxamic acid, or combinations thereof. In some embodiments, any of the aforementioned components are present in an amount from about 0.001 wt % to about 99% wt %, including 0.001, 0.002, 0.003, 0.004, 0.005, 0.01, 0.02, 0.03, 0.04, 0.05, 0.1, 0.2, 0.3, 0.4, 0.5, 1, 2, 3, 4, 5, 10, 15, 20, 25, 30, 35, 40, 45, 50, 55, 60, 65, 70, 75, 80, 85, 90, 95, 96, 97, 98, or 99%, or an amount within a range defined by any two of the aforementioned values.

Platelet buffering ingredients may include magnesium chloride, potassium chloride, glucose, sodium bicarbonate, sodium chloride, sodium citrate, sodium acetate, sodium phosphate, Fetal Bovine Serum (FBS). These can also be included for the first formulation.

EXAMPLES

Some aspects of the embodiments discussed above are disclosed in further detail in the following examples, which are not in any way intended to limit the scope of the present disclosure. Those in the art will appreciate that many other embodiments also fall within the scope of the disclosure, as it is described herein above and in the claims.

Example 1: Preparation of a Base Composition

The following example demonstrates preparation of a base composition that preserves, extends the life of, enhances, maintains, sustains, or otherwise prolongs biologics for extended periods of time.

The base composition was prepared by mixing the ingredients provided in Table 1.

TABLE 1

| Component | Wt % |
| --- | --- |
| Water | 92.72 |
| Polyacrylate crosspolymer-6 | 1.3 |
| *Lonicera japonica* (honeysuckle) flower extract | 1.2 |
| Glycerin | 1.2 |
| Niacinamide | 1 |
| *Lonicera caprifolium* (honeysuckle) flower extract | 0.5 |
| *Persea gratissima* (avocado) oil | 0.5 |
| *Aloe barbadensis* leaf juice | 0.5 |
| Citric acid | 0.3 |
| Sodium gluconate | 0.2 |
| Sodium hyaluronate (L) | 0.1 |
| *Althaea officinalis* (marshmallow) root extract | 0.1 |
| O-cymen-5-OL | 0.1 |
| Glucose (D) | 0.1 |
| Sodium chloride | 0.01 |
| Sodium citrate | 0.01 |
| Sodium acetate | 0.01 |
| Sodium bicarbonate | 0.01 |
| Tocopheryl acetate (D-alpha) | 0.01 |
| Potassium phosphate | 0.01 |
| Potassium chloride | 0.01 |
| Magnesium chloride | 0.01 |

Example 2: Kits for Formulations for Treating a Skin Disorder or Signs of Aging

In some embodiments, a kit for treating a skin disorder or signs of aging is provided. The kit comprises a first formulation having a topical cosmetic base, gel, serum, and cream or combination thereof, wherein the first formulation is mixed with platelet rich plasma, and wherein the first formulation further comprises nutrients, botanicals, preservatives or skin penetrators or a combination thereof, and a spray bottle or aerosol container holding a second formulation, the second formulation including a platelet rich plasma activator in liquid suspension. In some embodiments of the kit, the kit comprises the second formulation as a liquid, wherein the liquid is stored in a spray bottled. In some embodiments, the spray is a pump spray or an aerosol spray.

Selection of Subjects for Treatment Formulations

In the embodiments herein, subjects are selected based on their skin ailments or disorders which may be selected from stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof.

Whole blood is obtained from a subject having skin damage which is then centrifuged to separate platelet rich plasma from platelet poor plasma and red blood cells. Speeds to separate the PRP from platelet poor plasma can be adjusted accordingly and is a technique known to those of skill in the art. The platelet rich plasma (PRP) is then collected and a base composition is added such as a topical cosmetic base, a gel, a serum, a lotion, an ointment, a spray, an aerosol, a powder, a solution, a liquid, a foam, a salve, a paste, or a cream or combination thereof to form PRP admixed solution thereby forming a first topical formulation. The base composition preserves, extends, enhances, maintains, sustains, or otherwise prolongs the PRP for a period of more than 30, 40, 50, 60, 70, 80, 90, 100, or 120 days such that the first topical formulation may be used having functional PRP at a time period of more than 30, 40, 50, 60, 70, 80, 90, 100, or 120 days after being prepared.

The first topical formulation is then added to the skin damage for a 90 day time period, for up to 1, 2, 3 or 4 times a day, for up to 30, 60, 90 or 120 days or any number of days in between a range defined by any two aforementioned values.

The cells in the first formulation are then activated by providing a second topical formulation to the subject, wherein the providing comprises instructions to the subject for applying the second topical formulation over the area of the skin and skin damage that has received the first topical formulation, wherein the second topical formulation activates the platelet rich plasma, and wherein the activating comprises administering the second topical formulation onto the skin of the subject, and wherein the second topical formulation is applied over the skin that has received the first formulation.

The subject is then monitored by a medical professional. The second formulation may be sprayed onto the subject or may be applied as a lotion.

In an alternative of this example, the first formulation is provided to the subject and retained at a refrigerated temperature. The first formulation is then applied to the skin of the subject, such as to the face of the subject, and application of the first formulation increases the temperature of the first formulation to room temperature or greater. The change in temperature activates the PRP.

An alternative kit and/or method is provided, wherein the kit provides instructions for the user to obtain a sample of whole blood from the subject, and to process the whole blood to obtain PRP. The PRP is then submitted to lyophilization to obtain a lyophilized PRP powder. The PRP powder is weighed and aliquoted in specific amounts in separate vessels, and stored for later usage. When ready for use, the PRP is dissolved by adding to the vessel a dissolution solution, which includes sodium chloride, phosphate buffered saline, saline, or other dissolving agent, thereby generating a PRP solution. The PRP solution is then added to a base composition as described herein, such that the base composition preserves, extends, prolongs, maintains, or sustains the PRP. Furthermore, the base composition preserves, extends, prolongs, maintains, or sustains components of PRP, such as growth factors, or other biomolecules associated with PRP. The base composition preserves the PRP in the solution for a period of 30, 45, 60, 75, 90, 105, or 120 days, or longer, such that the PRP formulation exhibits therapeutically effective results when applied on the skin of the subject over a treatment period. Upon complete usage of the PRP formulation, or after a period of time wherein the PRP or the components thereof are no longer viable, a second aliquot of lyophilized PRP powder may be dissolved and combined with the base composition. Thus, due to the combination of both prolonged activity of the PRP and components thereof in the base composition and the securement of multiple aliquots of lyophilized PRP powder, following the initial draw of whole blood and subsequent processing to obtain PRP, the subject does not need to further draw blood or process the blood to obtain PRP for an extended period of time.

In some embodiments, the lyophilized PRP powder remains stable for a period of longer than 22 months. In some embodiments, the PRP formulation in the base composition is applied topically to a subject for treatment of post laser or post-operative procedures to enhancing healing effects, for minimizing scar tissue formation, or for reducing the appearance of scars.

Example 3: Improved Outcome Based on the Time of Incubation of the First Formulation on the Skin of a Subject In the embodiments herein, subjects were selected based on their skin ailments or disorders which may be selected from stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof.

Whole blood is obtained from a subject having skin damage which is then centrifuged to separate platelet rich plasma from platelet poor plasma and red blood cells. The platelet rich plasma (PRP) is then collected and a topical cosmetic base is added such as a gel, serum, and cream or combination thereof to form PRP admixed solution thereby forming a first topical formulation.

The first topical formulation is then applied to the skin damage for a 90 day time period, for up to 1, 2, 3 or 4 times a day, for up to 30, 60, 90 or 120 days or any number of days in between a range defined by any two aforementioned values.

Example 4: Study of the Formulation

In a study of 6 patients, the first formulation is applied to subjects who have skin damage and spots which are due to excessive sun exposure. The patients are selected by a dermatologist for the treatment.

The cells in the first formulation are then activated by providing a second topical formulation to the subject, wherein the providing comprises instructions to the subject for applying the second topical formulation over the area of the skin and skin damage that has received the first topical formulation, wherein the second topical formulation activates the platelet rich plasma, and wherein the activating comprises administering the second topical formulation onto the skin of the subject, wherein the second topical formulation is applied over the skin that has received the first formulation.

The subject is then monitored by a medical professional. Two patients are selected to have the second formulation applied as a lotion, two patients are selected to have the second formulation applied as a foam and two patients are selected to have the second formulation applied as a spray.

The first formulation is applied on each patient for 30 days. The second formulation is applied on the area of application of the first formulation for each patient for 30 days. Alternatively, the second formulation is applied each day after until 30 days after a single application of the first formulation. The first formulation is washed off once it is fully activated by the second formulation. The first formulation can be applied 1, 2, 3, 4 times a day and therefore each time the first formulation is applied the second formulation would be then applied and kept on the face until fully activated.

The patients are monitored for improvement of their skin in the area of treatment each week for two months after application. Improvement of the skin tone, coloring, skin damage and spots is expected to be markedly improved for all patients receiving treatment. However, the greatest improvement in skin tone, coloring, skin damage and spots is expected in the patients that received the second formulation as a spray.

Example 5: The Base of Formulation 1

In some embodiments, the first formulation is provided, wherein the first formulation comprises a base into which the cells are mixed thereby forming the first formulation. In some embodiments, the base composition comprises aqua (water), Lonicera japonica (honeysuckle) flower extract, glycerin, niacinamide, polyacrylate crosspolymer-6, Lonicera caprifolium (honeysuckle) flower extract, Persea gratissima (avocado) oil, Aloe barbadensis leaf juice, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, Rosmarinus officinalis (rosemary) leaf oil, *Thymus vulgaris* (thyme) flower/leaf oil, benzyl alcohol, caprylyl glycol, caprylhydroxamic acid, or combinations thereof.

In some embodiments, formulation 1 and/or formulation 2 comprises skin penetrators, preservatives and/or botanicals. In some embodiments, the skin penetrators include Fulvate fractions (Omni Bioceutical Innovations) liposomes, nanoparticles, dimethylsulfoxide, sodium lauryl sulfate, hyaluronic acid, nanostructured lipid.

In some embodiments, the a method of diminishing pore size, diminishing bacteria damage, diminishing red areas, reducing skin damage caused by sun, and maintaining or improving skin tone in a subject in need thereof is provided. The method comprises obtaining whole blood from a subject having an area of skin damage; centrifuging the blood to separate platelet rich plasma from platelet poor plasma and red blood cells; collecting the platelet rich plasma (PRP); adding a base to the PRP to form PRP admixed solution thereby forming a first topical formulation; providing the first topical formulation to the subject for treatment of the area of skin damage for a 90 day time period, wherein the providing comprises instructions for the subject to topically apply the first topical formulation to the area of skin damage 1, 2, 3 or 4 times a day, for up to 30, 60, 90 or 120 days or any number of days in between a range defined by any two aforementioned values; and providing a second topical formulation to the subject, wherein the providing comprises instructions to the subject for applying the second topical formulation over the area of skin damage that has received the first topical formulation, and wherein the second topical formulation activates the platelet rich plasma. In some embodiments, the base comprises botanicals and preservatives. In some embodiments, the base comprises aqua (water), Lonicera japonica (honeysuckle) flower extract, glycerin, niacinamide, polyacrylate crosspolymer-6, Lonicera caprifolium (honeysuckle) flower extract, Persea gratissima (avocado) oil, Aloe barbadensis leaf juice, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, Rosmarinus officinalis (rosemary) leaf oil, *Thymus vulgaris* (thyme) flower/leaf oil, benzyl alcohol, caprylyl glycol, caprylhydroxamic acid, or combinations thereof.

In some alternatives, the base comprising aqua (water), Lonicera japonica (honeysuckle) flower extract, glycerin, niacinamide, polyacrylate crosspolymer-6, Lonicera caprifolium (honeysuckle) flower extract, Persea gratissima (avocado) oil, Aloe barbadensis leaf juice, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, Rosmarinus officinalis (rosemary) leaf oil, *Thymus vulgaris* (thyme) flower/leaf oil, benzyl alcohol, caprylyl glycol, caprylhydroxamic acid, or combinations thereof, is provided in a kit.

The kit comprises a first formulation having a topical cosmetic base, gel, serum, and cream or combination thereof, wherein the first formulation is admixed with platelet rich plasma, and wherein the first formulation further comprises nutrients, botanicals, preservatives or skin penetrators or a combination thereof, and a spray bottle or aerosol container holding a second formulation, the second formulation including a platelet rich plasma activator in liquid suspension. The second formulation comprises calcium, magnesium, sodium, components of snake venom or combinations thereof. In some embodiments, the component of snake venom comprises Batroxobin. In some alternatives of the kit, the a base is provided wherein the base comprises aqua (water), Lonicera japonica (honeysuckle) flower extract, glycerin, niacinamide, polyacrylate crosspolymer-6, Lonicera caprifolium (honeysuckle) flower extract, Persea gratissima (avocado) oil, Aloe barbadensis leaf juice, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, Rosmarinus officinalis (rosemary) leaf oil, *Thymus vulgaris* (thyme) flower/leaf oil, benzyl alcohol, caprylyl glycol, caprylhydroxamic acid, or combinations thereof.

Example 6: A Base Composition for the First Formulation

In some embodiments, the first formulation is provided as described in Example 1. The first formulation comprises a base composition in which the cells are mixed, thereby forming the first formulation. In some embodiments, a kit is provided, wherein the kit comprises a first formulation having a topical base wherein PRP is admixed into, thereby forming the first formulation. In some embodiments of the kit, the base comprises aqua (water), Lonicera japonica (honeysuckle) flower extract, glycerin, niacinamide, polyacrylate crosspolymer-6, Lonicera caprifolium (honeysuckle) flower extract, Persea gratissima (avocado) oil, Aloe barbadensis leaf juice, sodium gluconate, sodium hyaluronate (L), Althaea officinalis (marshmallow) root extract, O-cymen-5-OL, sodium hydroxide, glucose (D), sodium chloride, sodium citrate, sodium acetate, sodium bicarbonate, tocopheryl acetate (D-alpha), potassium phosphate, potassium chloride, magnesium chloride, phenoxyethanol, Anthemis Nobilis (chamomile) flower oil, Rosmarinus officinalis (rosemary) leaf oil, *Thymus vulgaris* (thyme) flower/leaf oil, benzyl alcohol, caprylyl glycol, caprylhydroxamic acid, or combinations thereof.

Example 7: The Activator Spray Comprising the Second Formulation

The second formulation may be provided as an activator spray. The activator spray comprises Aqua (Water), Calcium Chloride (Can be any platelet activator), Polysorbate 80, Propylene Glycol, Sodium Chloride, Anthemis Nobilis (Chamomile) Flower Oil, Rosa Canina (Rose Hip) Fruit Oil, *Thymus vulgaris* (Thyme) Flower/Leaf Oil, Althaea Officinalis (Marshmallow) Root Extract, Hamamelis Virginiana (Witch Hazel) Water, Alcohol, Glycerin, Ethylhexylglycerin, Citric Acid, Potassium Sorbate, Phenoxyethanol.

Example 8: Longevity of PRP when Formulated in Base Composition

The following example demonstrates methods of increasing the longevity and activity of PRP over time when combined in a base composition.

PRP was collected from a subject. Five compositions were prepared in duplicate as follows: base composition alone; PRP alone; base composition+PRP; base composition+PRP+activator spray composition; base composition+PRP+calcium chloride. One group of formulations is prepared and stored at room temperature for a period of 0, 5, 15, 30, 45, 60, 75, and 90 days, and the second group of formulations is prepared and stored at 4° C. for a period of 0, 5, 15, 30, 45, 60, 75, and 90 days.

The base composition of Example 1 is combined with PRP, and PRP activity is assessed by ELISA activity and Western blot analysis at time point 0, 5, 15, 30, 45, 60, 75, and 90 days to verify that the growth factors remain active over the time period. Various growth factors are analyzed over time, including EGF, FGF basic, PDGF-AB, TGF-B1, and VEGF. Samples for the ELISA and Western blot analysis is performed at room temperature over the test period or at 4° C. during the test period, and includes the following conditions: the base composition alone (control), PRP alone (either fresh or lyophilized-control), base composition+PRP, base composition+PRP+activator (including one or more of calcium chloride, autologous thrombin, batroxobin, bovine thrombin, or collagen). The activator is included either as a direct component added by mixing or as prepared activator composition, such as a spray.

Platelets are analyzed via apoptosis. Platelet apoptosis can be triggered by multiple cell-external chemical stimuli, including platelet agonists thrombin and calcium ionophore A23187, pro-apoptotic anti-platelet antibodies, von Willebrand factor (VWF) in combination with the antibiotic ristocetin, mimetics of pro-apoptotic 'BH3-only' proteins of the Bcl-2 family and other chemical stimuli, as well as by exposure of platelets to very high pathological shear stresses. These chemical and physical stimuli induce transformation of resting (non-apoptotic) platelets to an apoptotic state. Depending on the nature of the trigger, this transformation is accompanied by stimulation of various apoptotic events, which may include DWm depolarization, MPTP formation, expression, activation and translocation to mitochondria of pro-apoptotic members of Bcl-2 family proteins (such as Bax, Bak and Bid), cytochrome c release from mitochondria to the cytosol, activation of caspases, cleavage of cytoskeleton proteins, PS exposure on the outer leaflet of plasma membrane, platelet shrinkage, shedding of platelet derived MPs, and blebbing, and filopod formation on platelet membrane. Driven by the plasma membrane alterations, damaged platelets can be recognized by the reticuloendothelial system as 'unwanted' cells and removed from the circulation. Different markers of platelet apoptosis can characterize apoptotic events in different cellular compartments, such as mitochondria, cytosol and plasma membrane, as well as at the whole-cell level. Various markers, methods, and probes may be used for studying platelet apoptosis, as shown in Table 2, and as described in further detail in Gyulkhendanyan et al., BJH, 2013.

TABLE 2

| Markers of apoptosis | Cell compartments | Methods | Detecting probes |
|---|---|---|---|
| Upstream markers | | | |
| $\Delta\Psi m$ depolarization | mitochondria | Flow cytometry | DiOC6(3), JC-1 |
| Bax, Bak and Bcl-2 proteins expression and translocation to mitochondria | Cytosol and outer mitochondrial membrane | Flow cytometry; Western blot | Anti-Bax/-Bak/-Bcl-2 antibodies + FITC-conjugated secondary antibody; |

TABLE 2-continued

| Markers of apoptosis | Cell compartments | Methods | Detecting probes |
|---|---|---|---|
| | | | anti-Bax/-Bak/-Bcl-2 antibodies + HRP-conjugated secondary antibody; anti-cytochrome c antibody |
| Cytochrome c release | Mitochondrial intermembrane space and cytosol | Western blot | Anti-cytochrome c antibody |
| Downstream markers | | | |
| Caspase-3 activation | cytosol | Flow cytometry | FAM-DEVD-FMK |
| Phosphatidyl serine exposure | Plasma membrane | Flow cytometry | FITC or PE labeled annexin V |
| Microparticle shedding | Whole-cell level | Flow cytometry; scanning electron microscopy | FSC-anti-GPIIbIIIa dot plot analysis |
| Platelet shrinkage | Whole-cell level | Flow cytometry; scanning electron microscopy | FSC histogram analysis |
| Membrane blebbing and filopod extrusion | Plasma membrane | Scanning electron microscopy | |

ELISA, Western blot, or flow cytometry analysis are performed on apoptotic members of Bcl-2 family proteins Bax, Bak, and Bid for time points of 0, 5, 15, 30, 45, 60, 75, and 90 days. Expression of Bcl-2 family proteins in each sample (control, base composition with PRP, and base composition with PRP and activator), and is determined by flow cytometry.

In addition, ELISA, Western blot, and flow cytometry analysis is performed for cytochrome c release, caspase release, cytoskeleton proteins, and platelet derived MPs that are associated with platelets in PRP at time points 0, 5, 15, 30, 45, 60, 75, and 90 days where a gradual increase is observed over time as more platelets go through apoptosis. In addition, the activation of executioner caspase-3 in each sample is observed, which is dependent on MPTP formation, and is performed at each time point for all samples.

Platelet morphology changes as platelet lose stability and activate under stress, time, activation, and temperature. Platelet morphology is verified by observing microparticle shedding, platelet shrinkage, membrane blebbing, and filopod extrusion. Experimental techniques include flow cytometry, scanning electron microscopy, specific fluorescent probing analysis, and light scattering characteristic analysis.

Example 9: Base Formulation with PRP for Treating Skin Disorders

The following example demonstrates methods of treating skin disorders by applying to a patient PRP provided in a base composition. This example examines the ability of the formulations described herein including PRP in a base composition, wherein the PRP is obtained from the subject to whom it will be applied. This allows the creation of a personalized PRP cream to improve the appearance of the individual from whom the PRP was harvested. However, PRP is a large molecular weight protein that does not readily penetrate the skin. This research enhances the PRP delivery through the adjunctive use of a skin obstruction device, such as electroporation, ultrasound, radiofrequency, high intensity focused ultrasound, intense pulsed light (IPL), ablative laser, non-ablative laser, microdermabrasion, hydradermabrasion, iontophoresis, chemical peel, plasma, high velocity air, high velocity aqueous solution, or needling, or a combination thereof. Skin obstruction is used to create channels through which the PRP can penetrate into the viable epidermis and dermis to induce an anti-aging effect.

Female and male subjects were enrolled in this single site double blind vehicle controlled split face study to evaluate the effect of a PRP-containing cream on facial photoaging. Subjects completed a 3-day washout of any facial treatment, including moisturizers and cosmetics, except for lip and eye cosmetics. Subjects were asked to continue their self-selected cleanser unchanged throughout the 8-week study. Subjects were randomized to determine which side of the face received a PRP-containing cream and which side received a base control cream. Dermatologist investigator and subject assessments for efficacy and tolerability were conducted on a 5-point ordinal scale separately for each cheek. Transepidermal water loss (TEWL) was performed from the right and left cheeks and Visia CR photography of the front, right, and left face were completed prior to any treatment as baseline documentation.

The base composition with PRP was prepared using the base composition described in Example 1, formulated as a cream. Subjects applied one quarter sized amount of the cream twice daily into the freshly washed randomized half of the face to include the right or left cheeks, forehead, periocular, and perioral areas until the cream absorbs. To the other half of face was applied a quarter sized amount of a control cream (base composition alone without PRP) rubbed into the cheek, forehead, periocular, and perioral area twice daily until the cream absorbs. This split face application was performed twice daily (morning and evening) for the duration of the study. The creams were refrigerated during the study period.

Subjects underwent a phlebotomy procedure for harvesting of 50 mL of blood from which 6-9 mL of PRP was prepared according to directions supplied by the sponsor. Due to patient compliance, lower quantities of blood may be obtained, such as an amount of less than 50 mL, such as 5, 10, 15, 20, 25, 30, 35, 40, or 45 mL. PRP is prepared, wherein the PRP has platelet counts that are greater than normal platelet counts (for example, PRP has platelet counts greater than 150,000-350,000 platelets per microliter). Following phlebotomy, subjects underwent electroporation for 5 minutes total to the surface of the cheeks, forehead, periocular area, and perioral area. During this time, the subjects were educated on how to use the device at home for the duration of the study. The device was used in the evening only for 5 minutes. The device was used prior to the application of the study moisturizers in the evening only. 3 mL of PRP was added to a cosmetic base composition (outlined in Example 1) formulated as a cream that was applied to one randomized side of the face twice daily. To the other half of the face was applied a cosmetic base composition cream alone applied twice daily. Neither the subjects nor the investigator knew the identity of the creams that were applied to each side of the face. Subjects were instructed to return to the research facility at weeks 4 and 8.

Subjects were queried at week 4 and 8 for any adverse events. Compliance diaries were checked along with adequacy of the assigned study cream supply and proper electroporation device functioning. Diaries were checked for proper use of the electroporation device to the entire face for 5 minutes in the evening. Dermatologist investigator and subject assessments for efficacy and tolerability were conducted on a 5-point ordinal scale separately for each side of the face. TEWL is performed from the right and left cheeks and Visia CR photography of the front, right, and left face was completed. TEWL measurements (Dermalab, Cortex Technologies, Hadsund, Denmark) were taken from the right cheek in all subjects. Measurements occur at baseline, week 4, and week 8. Each side of the face was assessed separately. Visia CR4.3 photographs were taken of the front, right, and left face. Photographs were taken with the following lighting modes: Standard 1, Standard 2, Standard 3, Cross Polarized, and Parallel Polarized. Assessments occurred at baseline, week 4, and week 8.

The dermatologist and subject each assessed efficacy of the formulation by assessing dryness, lack of tactile smoothness, lack of visual smoothness, lack of softness, lack of luminosity, lack of radiance, lack of firmness, poor skin texture, fine facial lines, wrinkles, poor skin tone, mottled hyperpigmentation, overall appearance. All assessments were made on a 5-point ordinal scale (0=none, 1=minimal, 2=mild, 3=moderate, 4=severe) at baseline, week 4, and week 8. Each side of the face was assessed separately. The dermatologist and subject each assessed tolerability by assessing itching, stinging, burning, redness, and swelling. All assessments were made on a 5-point ordinal scale (0=none, 1=minimal, 2=mild, 3=moderate, 4=severe) at baseline, week 4, and week 8. Each side of the face was assessed separately.

A primary efficacy endpoint was a statistically significant improvement in facial photoaging, as assessed by the dermatologist investigator, produced by the PRP+cosmetic base composition cream as compared to the cosmetic base cream only when used in conjunction with home electroporation device. A secondary efficacy endpoint was a statistically significant improvement in facial photoaging, as assessed by the subjects, produced by the PRP+cosmetic base cream as compared to the cosmetic base cream only when used in conjunction with an electroporation device. A tertiary efficacy endpoint was a statistically significant improvement in skin barrier, as measured by a reduction in TEWL, produced by the PRP+cosmetic base cream as compared to the cosmetic base cream only when used in conjunction with an electroporation device.

The ordinal investigator and subject nonparametric data were analyzed using a Mann Whitney paired two-tailed analysis evaluating change from baseline comparing the active PRP+base cream treated side of the face to the base cream only treated side of the face. The parametric TEWL data were analyzed using a Student t test comparing the active PRP treated side of the face to the control vehicle treated side of the face. Significance was defined at p less than or equal to 0.05.

Subjects in the biopsy study underwent a 2 mm punch biopsy from the left and right preauricular areas, following anesthesia with 2% lidocaine plus epinephrine. The biopsy sites were closed with one suture. The biopsies showed increased collagen and elastin expression over time in portions of the skin having the base composition with PRP applied. Biopsies for qPCR and immunohistochemistry showed upregulation of key factors of tissue healing. The specimens were processed, sectioned, and hematoxylin and eosin (H&E) stained. H&E stained 5 μm serial sections from paraffin blocks and were digitally scanned (NanoZoommer, Hamamatsu, Japan). Length profile measurements of the stratum basale and stratum granulosum layers of the epidermis were obtained, generating a ratio between basale/granulosum layers. Nuclear counting and epithelial thickness measurements were conducted. Quantitative immunohistochemistry analysis for collagen I and elastin were quantified using a color deconvolution algorithm from digitally scanned immunohistochemistry slides. Quantitative polymerase chain reaction was conducted analyzing Collagen 1A1 (COL1 A), keratinocyte proline rich protein (KPRP), and matrix metalloproteinase 1 (MMP1) genes.

Quantitative PCR (qPCR) was performed on biopsy tissue samples that were preserved in RNA later solution. Fold change in mRNA expression between treatment and control for each subject was calculated using the following equation:

$$\text{Fold Change(FC)} = 2^{-(\Delta\Delta CT)}$$

An average fold change of 2 represents a significant upregulation in gene expression, and a 0.5 fold change represents a 2 fold decrease (downregulation) in gene expression. Next, the opposite integer of the ΔΔCT value was determined.

$$-\Delta\Delta CT = \log_2(FC)$$

Lastly an average FC was calculated for the specific probe analysis according to the following formula:

$$\text{Average FC} = 2^{\bar{x}}, \text{ where } \bar{x} \text{ is the average of the } -\Delta\Delta CT \text{ values}$$

Ordinal investigator and subject nonparametric data were analyzed using a Mann Whitney paired two-tailed analysis evaluating change from baseline comparing the active PRP+ base composition treated side of the face to the base composition only treated side of the face. The parametric TEWL, histology, and immunohistochemistry data were analyzed using a paired Student's t-test (p≤0.05).

All 20 subjects in the main study and the subjects in the biopsy sub-study successfully completed the study. No tolerability issues were noted by either the blinded investigator or the subjects with either the PRP+base composition or the base composition alone. This was confirmed by the lack of change in TEWL readings from both sides of the face. In addition, no statistically significant differences between the PRP+base composition treatment or the base composition alone treatment was noted by either the blinded investigator or the subjects after 8 weeks of use in any of the assessed parameters. Both sides of the face demonstrated statistically significant (p<0.001) improvement for dryness, tactile smoothness, visual smoothness, softness, luminosity, and radiance at 8 weeks. PRP+base composition did demonstrate directional improvement of radiance, luminosity, smoothness at 4 weeks, increasing at 8 weeks versus the base composition alone.

Figure 1B:
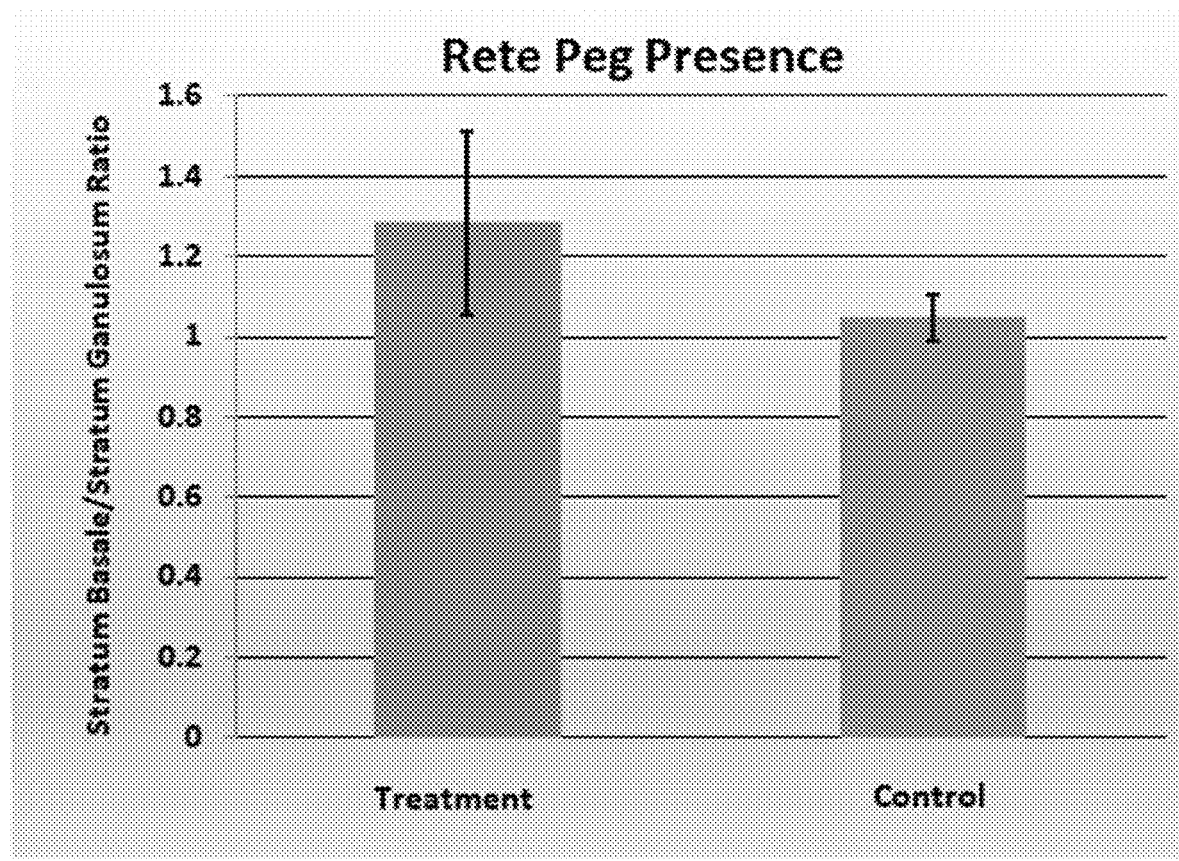
Figure 2A:
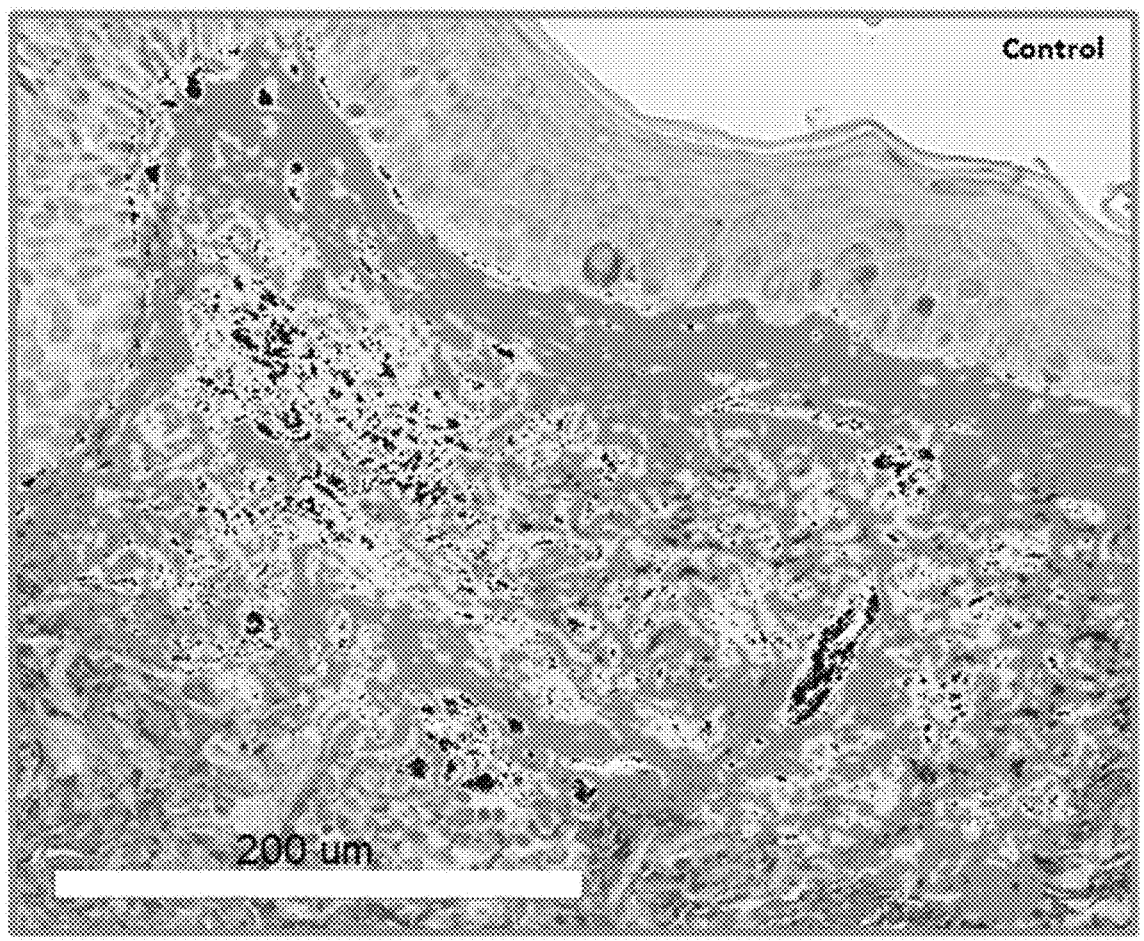
FIGS. 2A-2B illustrate micrographs showing collagen type I expression in control (FIG. 2A) and treatment (FIG. 2B) groups.
Figure 2B:
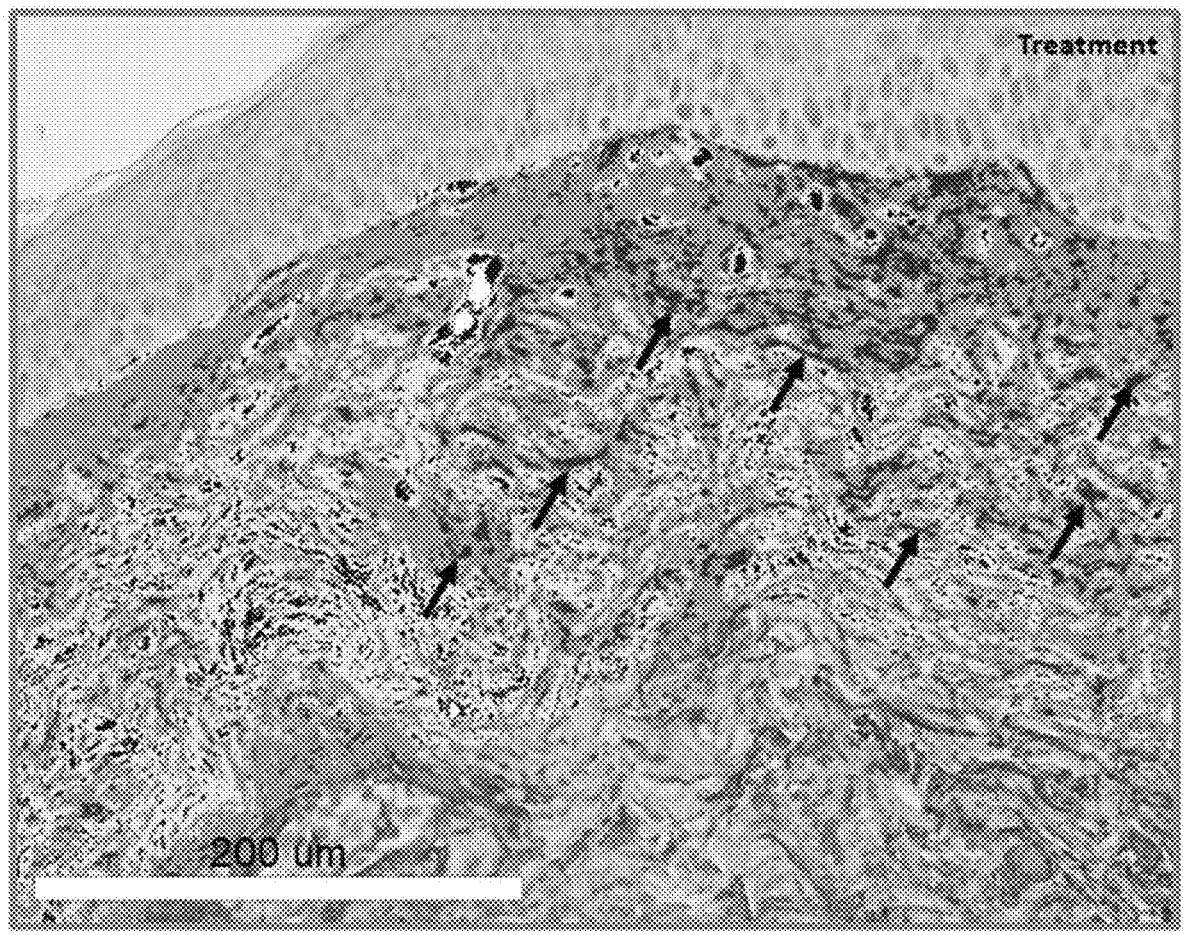

The histopathology findings demonstrated a qualitative improvement in the PRP+base composition treated group with a trend of greater rete peg presence in the PRP+base composition group compared to base composition controls (FIGS. 1A-1B). Immunohistochemistry revealed enhanced Collagen type I expression in the PRP+base composition treatment versus the base composition without PRP (FIGS. 2A-2B). These collagen findings were further supported by the qPCR data. Three target genes (collagen IA, matrix metalloproteinase 1 gene, and keratinocyte proline rich protein) and a housekeeping gene control was evaluated. Results demonstrated a 2.5-fold increase in collagen gene upregulation in the PRP treatment base composition vs. control base composition for collagen type I.

Figure 3:
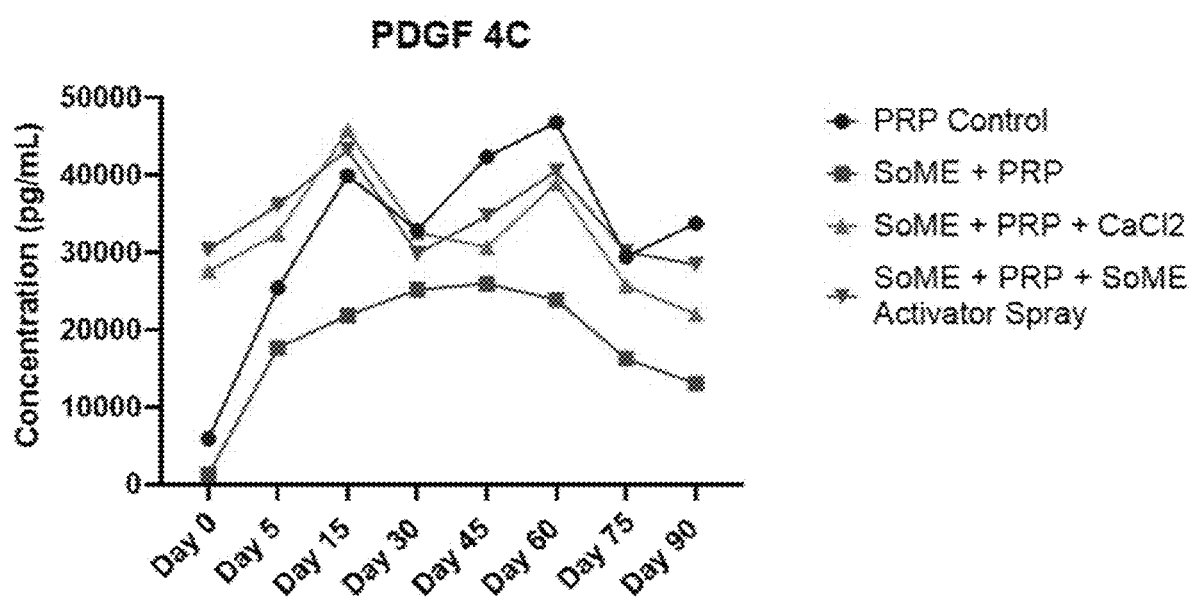
FIG. 3 illustrates intact platelet derived growth factor (PDGF) in compositions at 4° C. assessed over a period of 90 days after preparation. PRP control refers to PRP alone, whereas SoME+PRP refers to the PRP in base composition. Samples were stored at 4° C. and brought to room temperature at the time of the experiment.
Figure 4:
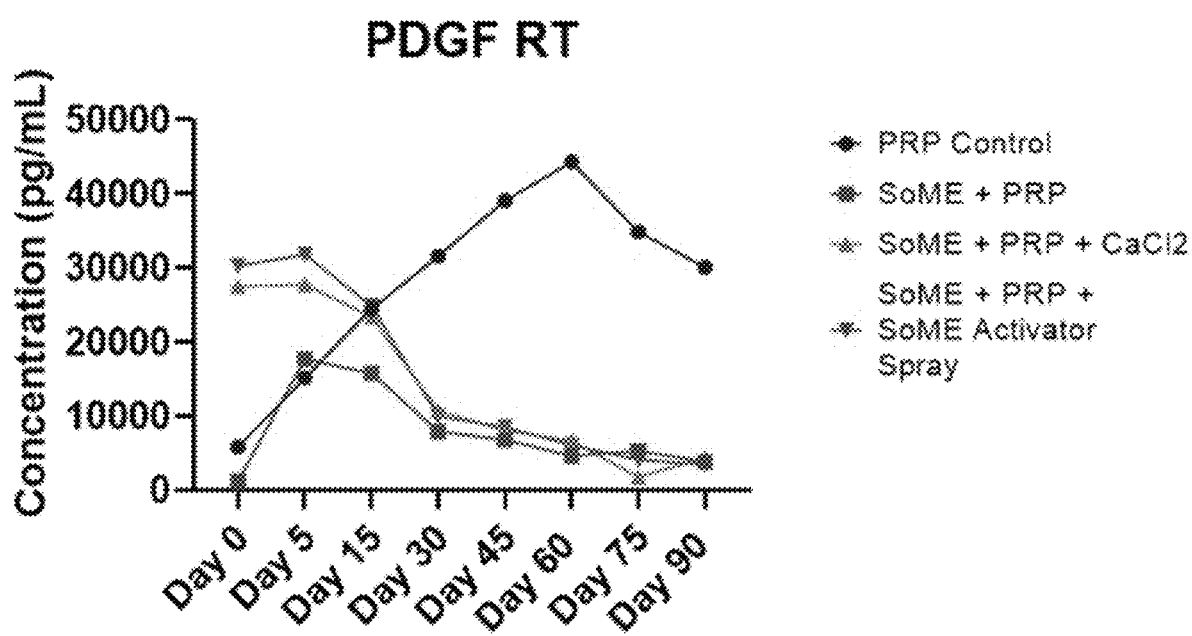
FIG. 4 illustrates intact PDGF in compositions stored at room temperature over a period of 90 days. SoME refers to the base composition.

The PRP+base composition formulation was evaluated for PRP stability as the effective duration of blood derived products has always been a limiting factor for topical application (FIG. 3). Intact PDGF was identified in the 4 degree Celsius constantly refrigerated preservative base composition 90 days after preparation. This was an important finding to allow further development of topical PRP cosmetics. The same compositions were evaluated at 4 degree Celsius with the addition of activator (activator spray or $CaCl_2$). The formulation was also evaluated at room temperature, as shown in FIG. 4.

Figure 5A:
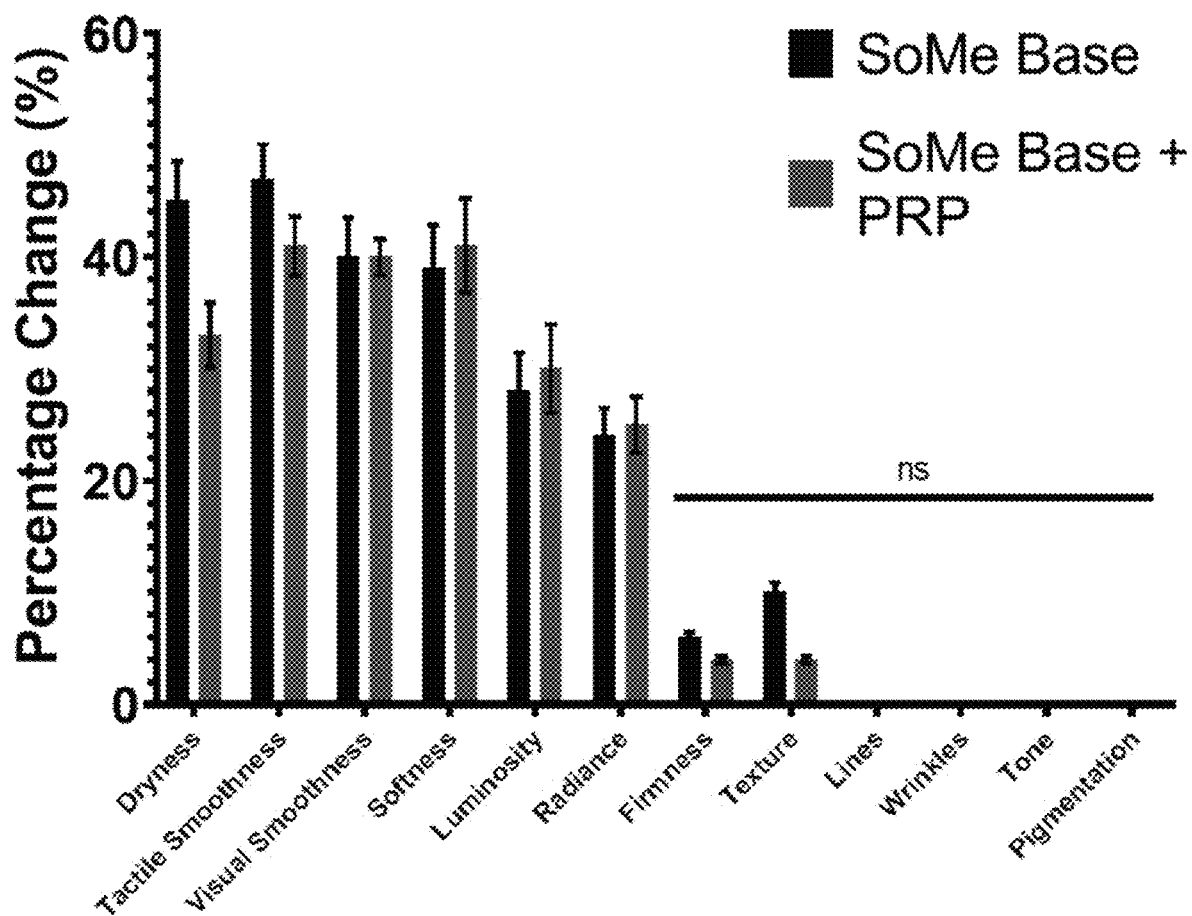
FIGS. 5A-5D graphically depict percentage change in assessment parameters. Various skin assessment parameters are shown for the base composition (SoME) compared to PRP+base composition at 4 weeks (FIG. 5A) and 8 weeks (FIG. 5B). The parameters are directly compared at 4 vs 8 weeks for PRP+base composition (FIG. 5C) and for the base composition alone (FIG. 5D).
Figure 5B:
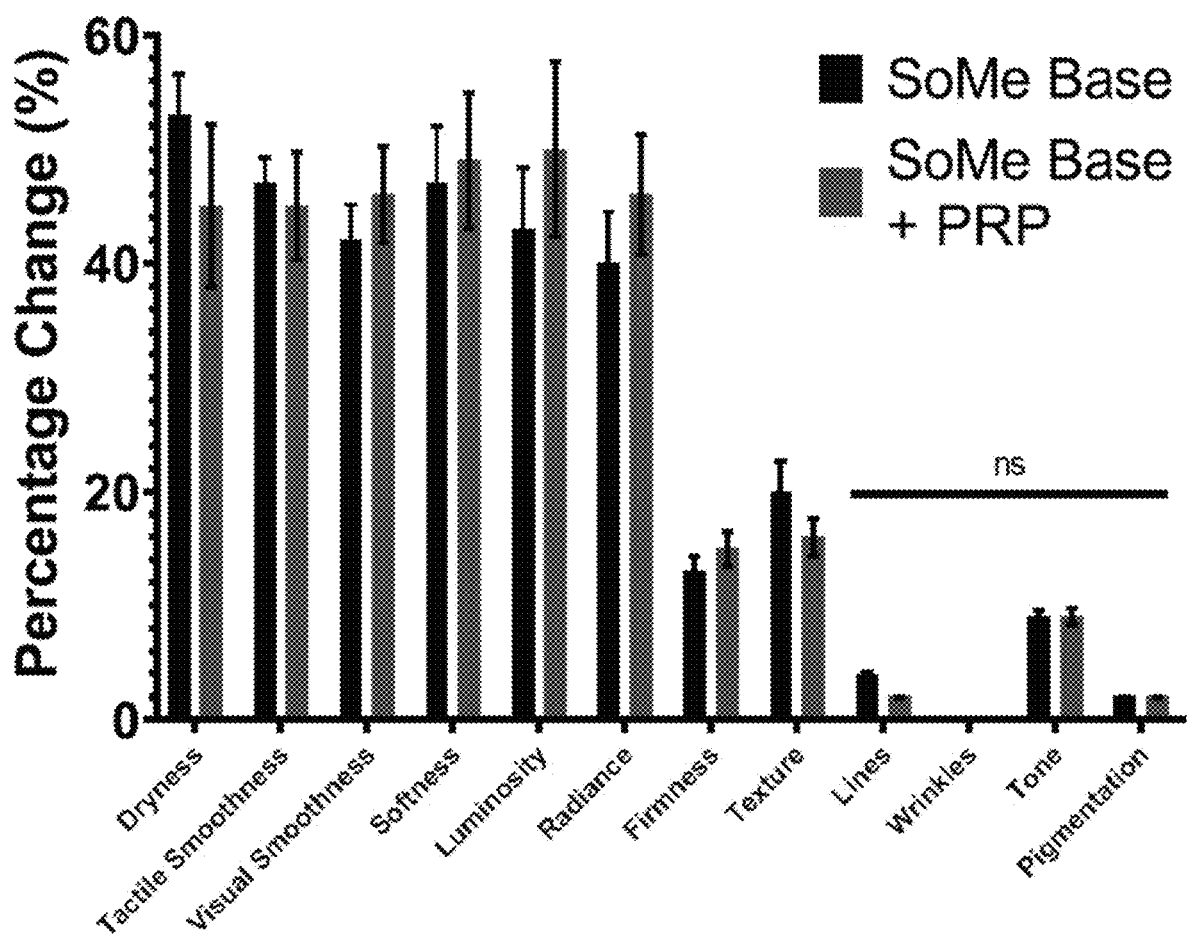
Figure 5C:
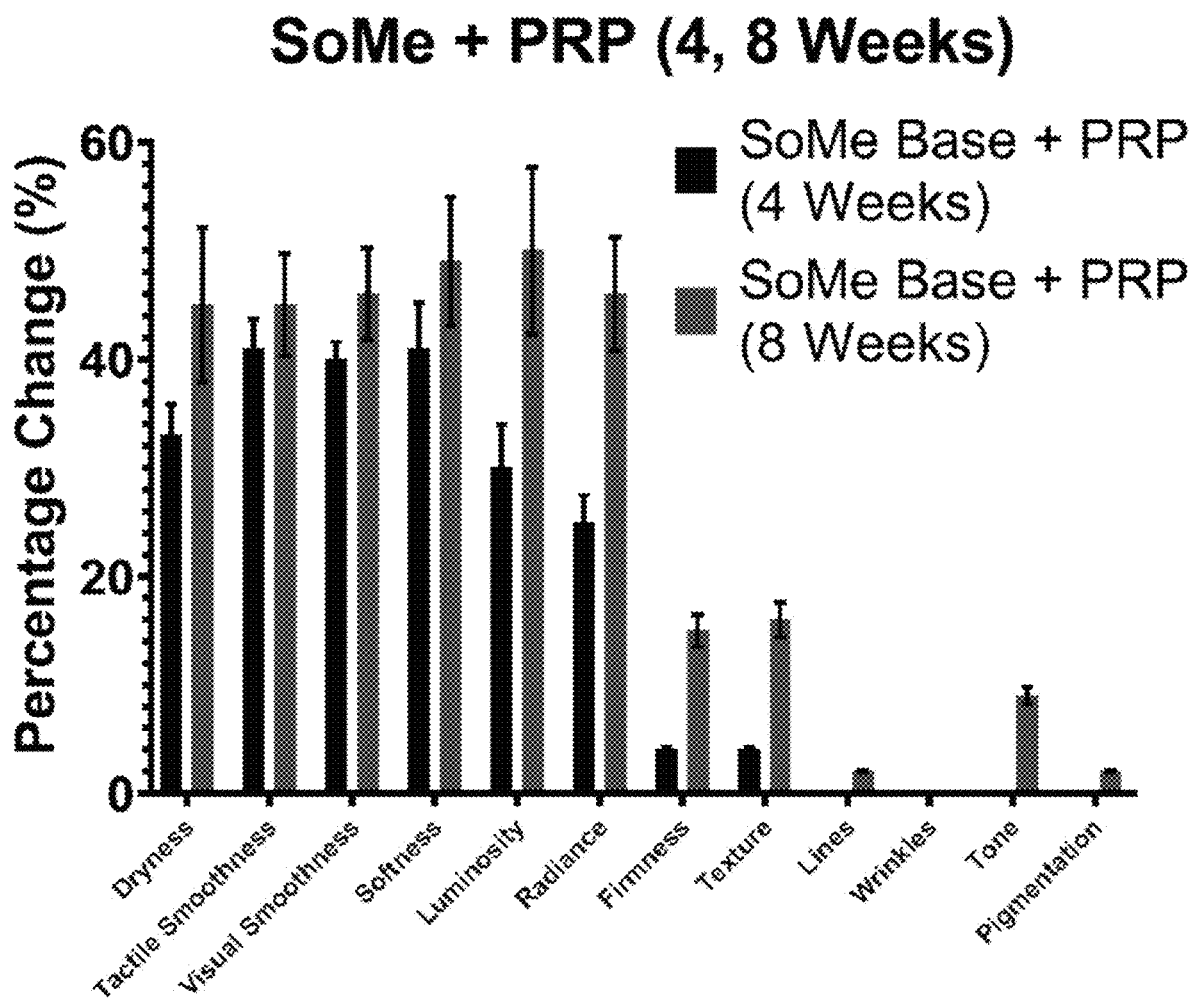
Figure 5D:
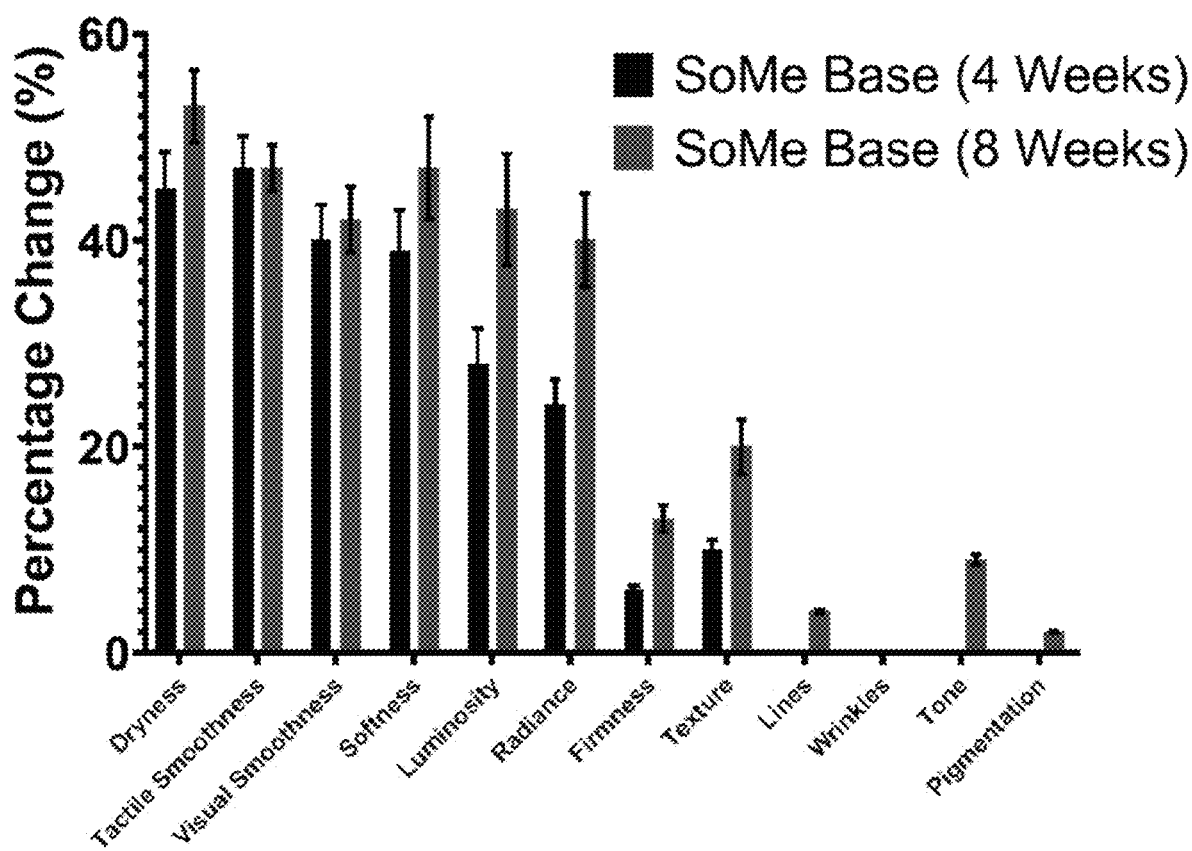
Figure 6:
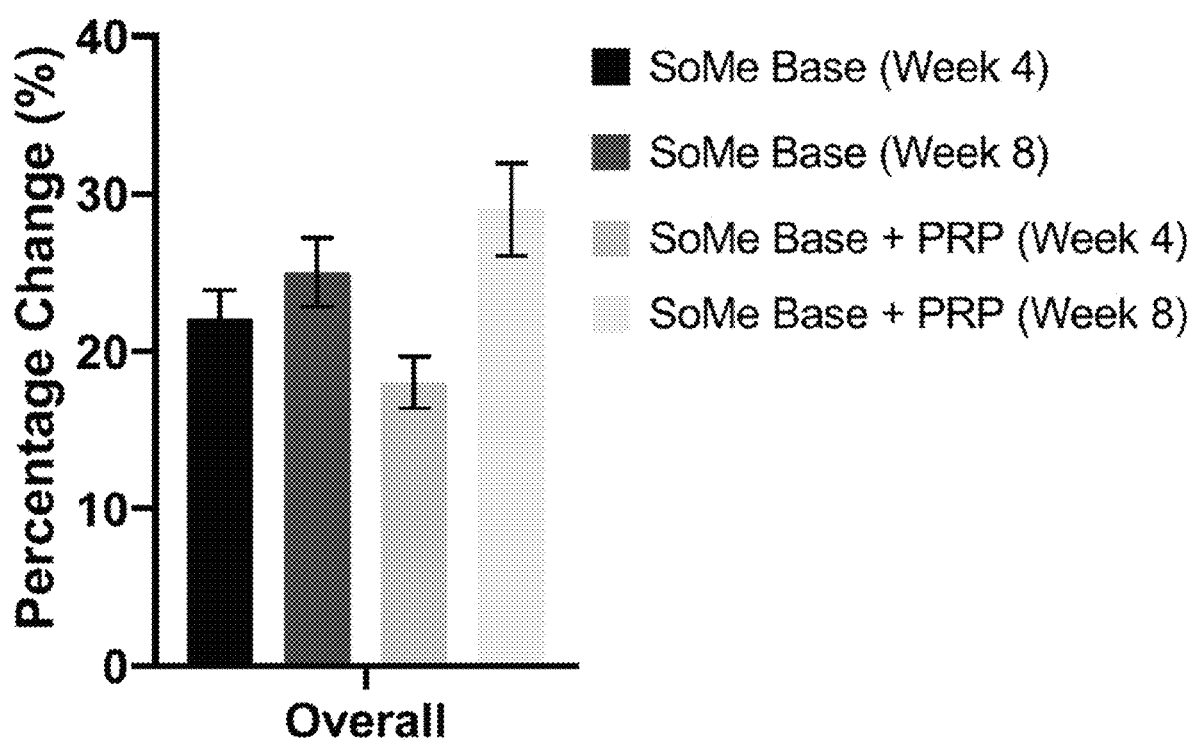
FIG. 6 graphically illustrates the overall assessment parameters as a function of percentage change for the base composition alone at 4 and 8 weeks and the PRP+base composition at 4 and 8 weeks.
Figure 7A:
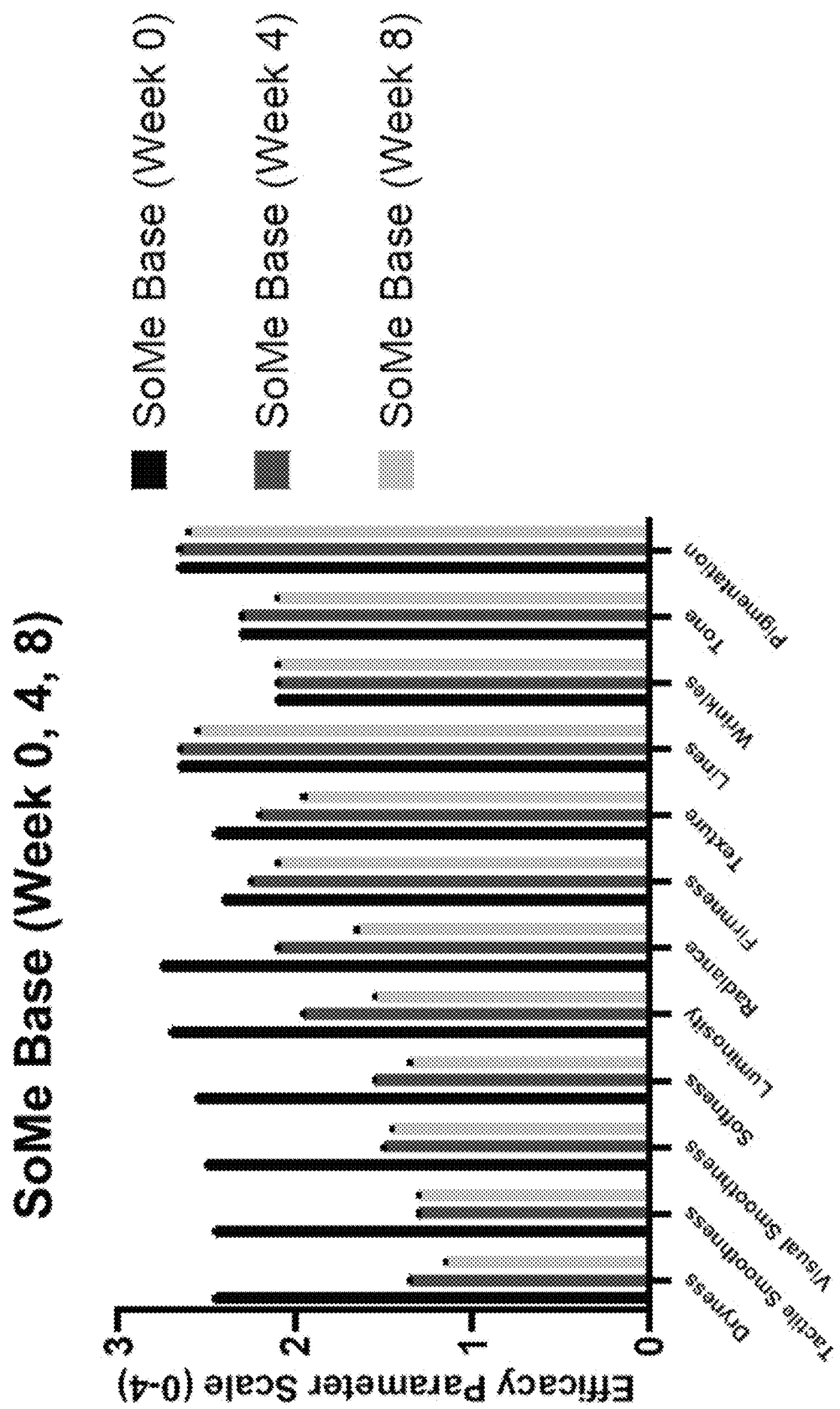
FIGS. 7A-7D graphically depict efficacy parameter scales for the change in skin assessment parameters. The efficacy parameters for weeks 0, 4, and 8 are shown for the base composition alone (FIG. 7A) and for the PRP+base composition (FIG. 7B). The efficacy parameters for 0 and 8 weeks are shown for the PRP+base composition (FIG. 7C) and for the base composition alone (FIG. 7D).
Figure 7B:
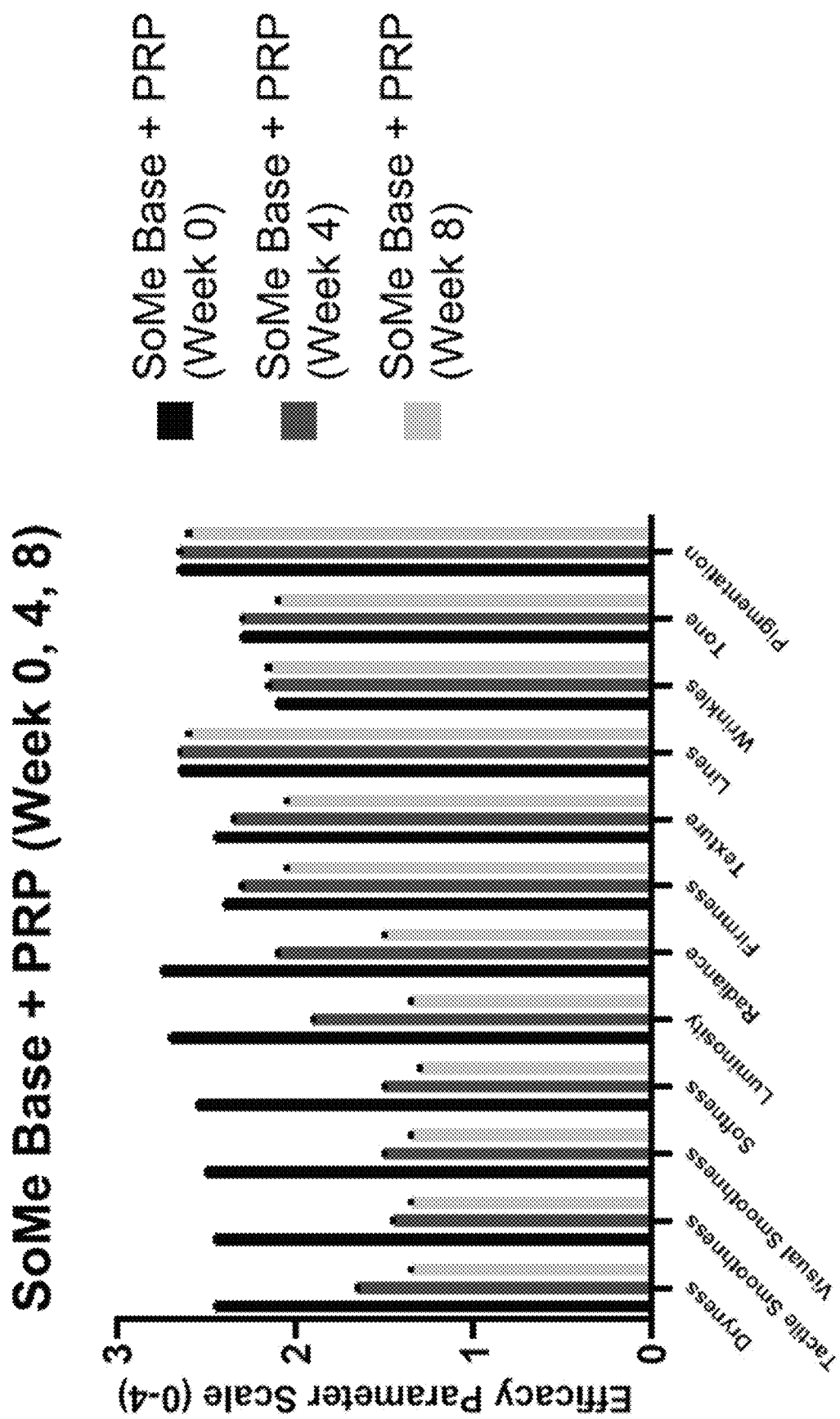
Figure 7C:
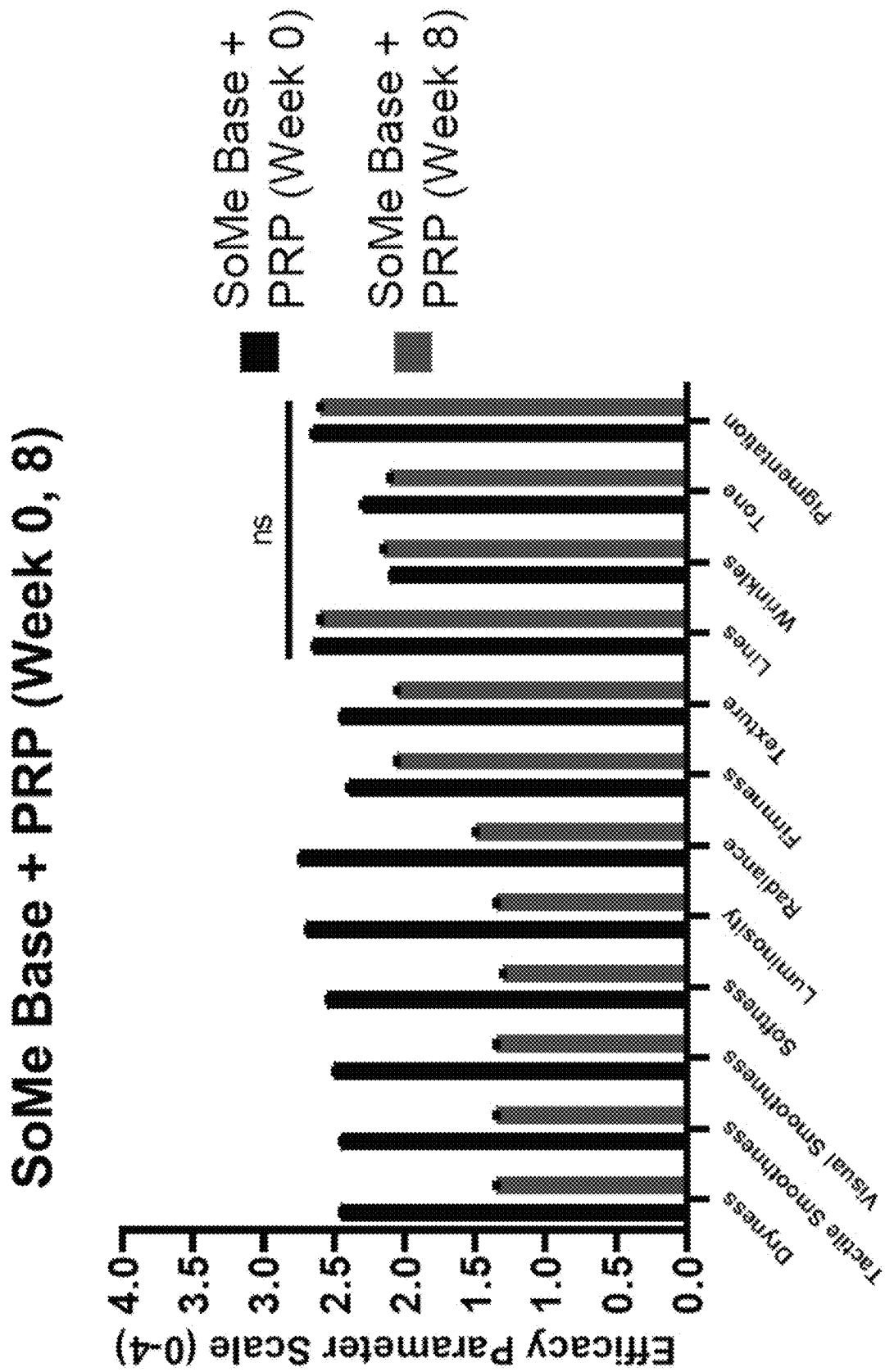
Figure 7D:
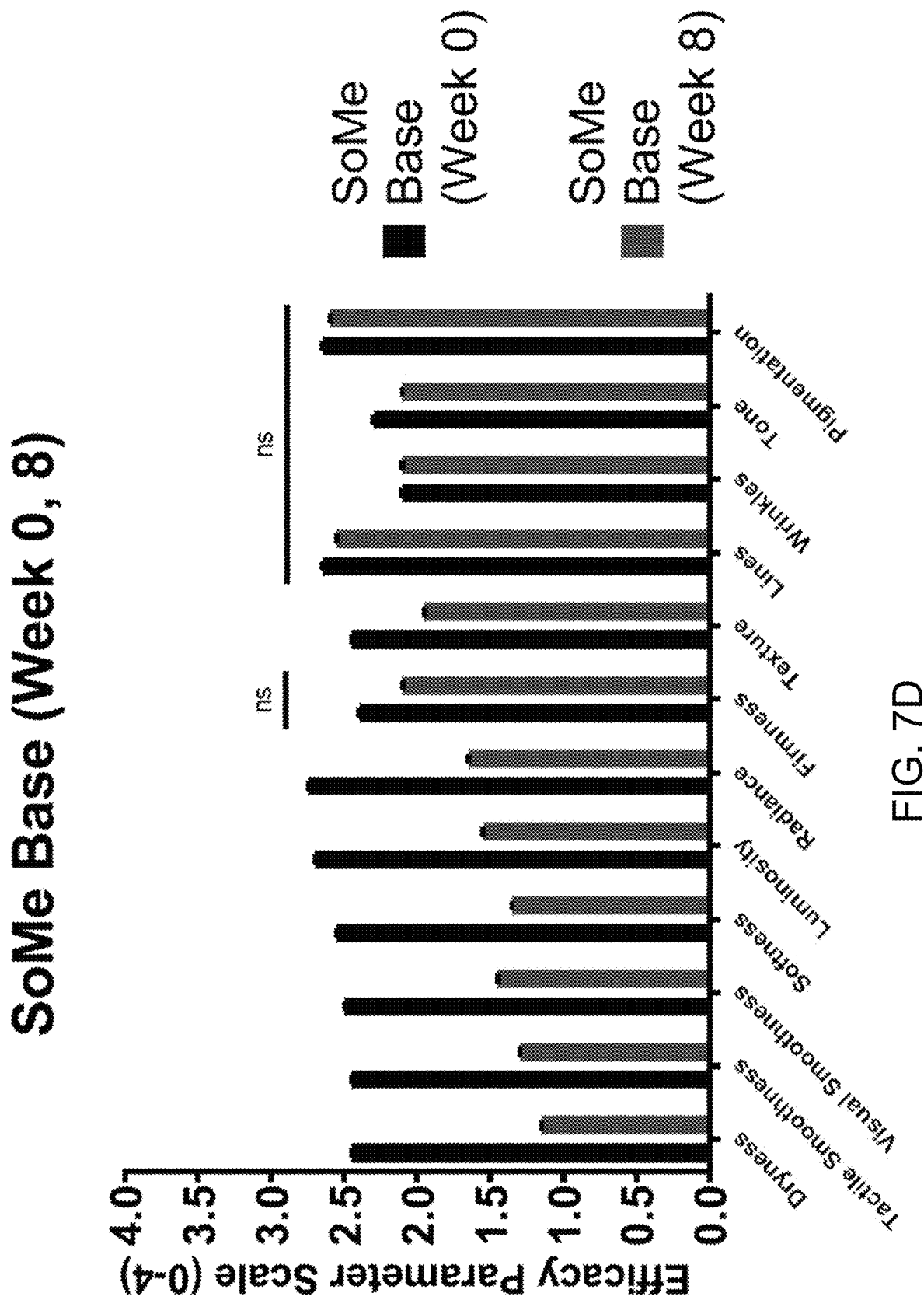
Figure 8:
FIGS. 8-15 show photographs of facial assessment prior to (week 0, left image) and after treatment (week 8, right image) in an example embodiment provided herein.
Figure 9:
Figure 10:
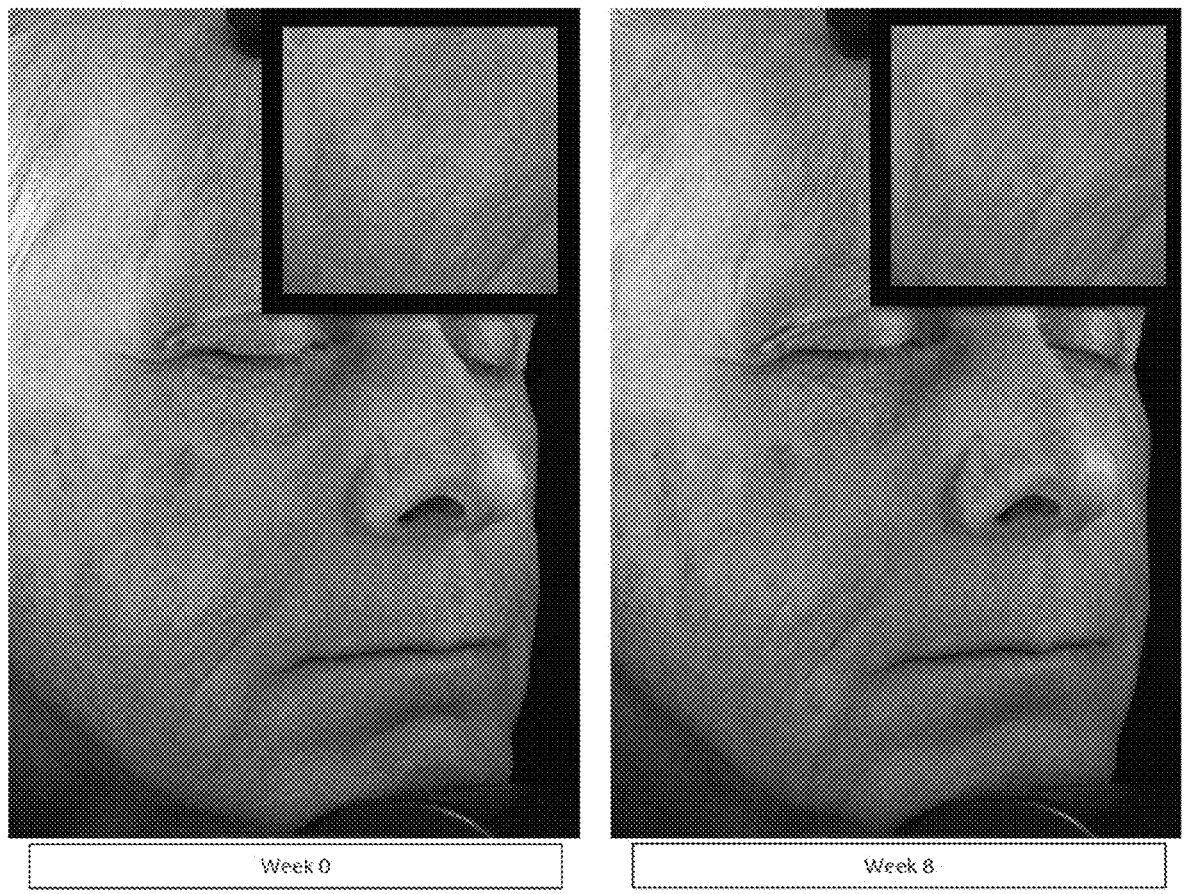
Figure 11:
Figure 12:
Figure 13:
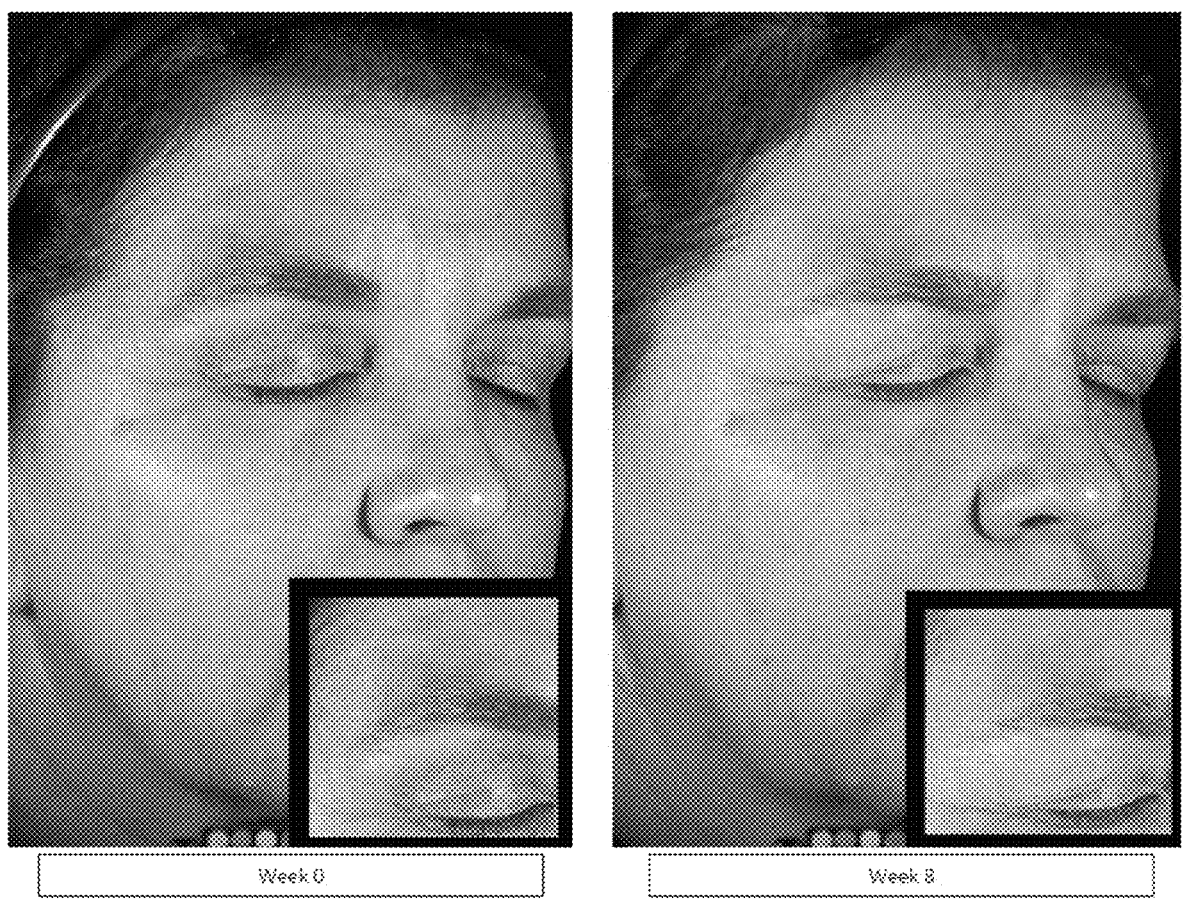
Figure 14:
Figure 15:
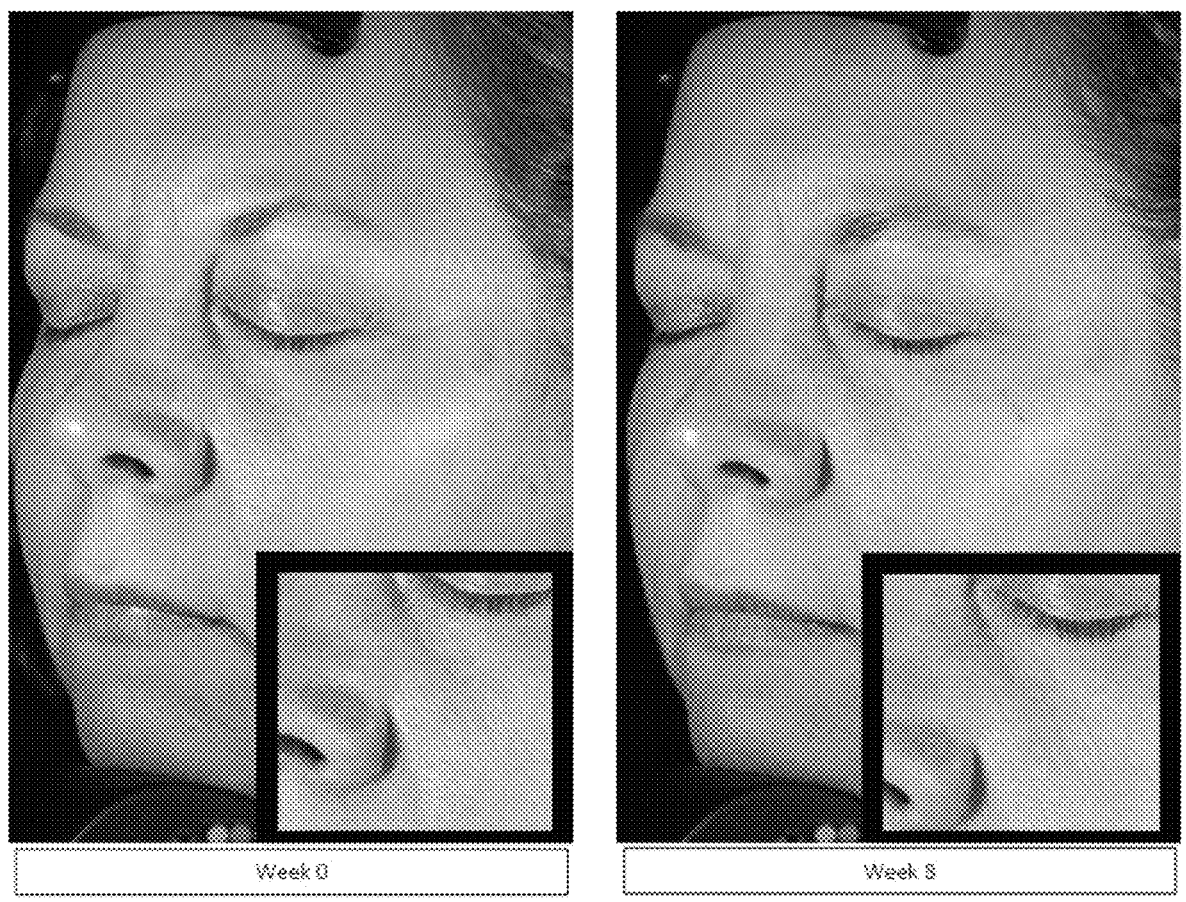

Assessments of skin rejuvenation in the base composition compared to PRP+base composition at 4 weeks is shown in FIG. 5A, and at 8 weeks is shown in FIG. 5B, with the 4 week to 8 week comparison of the PRP+base composition shown in FIG. 5C, and the comparison of 4 weeks to 8 weeks of the composition alone shown in FIG. 5D. The overall percentage change is shown in FIG. 6. The outcomes were also shown as a function of efficacy parameter scales on a scale of 0 to 4, with the composition alone shown in FIG. 7A, and the PRP+base composition shown in FIG. 7B. The 0 to 8 week comparisons are shown in FIGS. 7C and 7D.

The PRP+base composition demonstrated a directional enhanced performance at 4 weeks, increasing in performance at 8 weeks for radiance, luminosity, firmness, and softness versus the base composition alone. Further, the PRP+base composition demonstrated less epidermal cell compacting and greater cellular hydration versus the base composition alone. In addition, rete pegs typically extend into the dermis in younger individuals helping to solidify the integrity of dermal-epidermal junction (DEJ), improving skin strength. With increasing age, the rete pegs regress into the upper epidermis. The PRP+base composition demonstrated continued elongation of the rete pegs versus the base composition alone, with retraction of the rete pegs into the upper regions of the epidermis. Less rete peg connectivity to the DEJ results in the fragile crepey skin observed with aging. Immunohistochemistry results demonstrated higher levels of collagen type I and qPCR results showed upregulation of collagen mRNA.

Each subject was assessed by Visia CR4.3 photographs, with an initial photograph taken at the starting point (week 0), and a treatment photograph taken during treatment periods (week 8). The photographs were compared to assess each of a variety of skin assessments, including dryness, tactile smoothness, visual smoothness, softness, luminosity, radiance, firmness, texture, lines, wrinkles, tone, and pigmentation. The photographs show decreased red areas, decreased wrinkles, decreased pore size, improved skin tone, fewer spotting, indicating the ability of the PRP+base composition to mitigate signs of facial photoaging (FIGS. 8-15 depict exemplary images showing improvement in wrinkles, acne scars, skin elasticity, sagging skin, skin dryness, rashes, redness, translucency, fine lines, radiance, skin tone, pigmentation, discoloration, blotchiness, scarring, rough and leathery appearance, freckles, moles, actinic keratosis, wound healing, bruising and tearing, ruddiness, uneven texture, fine lines, age spots, or a combination thereof after treatment).

The side of the face having the base composition in combination with PRP exhibited a diminished pore size, diminished bacteria damage, diminished red areas, reduced skin damage caused by the sun, improved texture, and enhanced skin tone. In addition, skin of subjects having laser treatment also showed improved healing.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those of skill within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Any of the features of an embodiment of the first through second aspects is applicable to all aspects and embodiments identified herein. Moreover, any of the features of an embodiment of the first through third aspects is independently combinable, partly or wholly with other embodiments described herein in any way, e.g., one, two, or three or more embodiments may be combinable in whole or in part. Further, any of the features of an embodiment of the first through third aspects may be made optional to other aspects or embodiments.

What is claimed is:

1. A base composition for prolonging, preserving, or maintaining a biologic, the composition comprising:
   a cell culture nutrient;
   a biological buffer;
   a viscosity modifying agent, wherein the viscosity modifying agent comprises polyacrylate crosspolymer-6; and
   apple extract or apple skin extract.

2. The base composition of claim 1, wherein the cell culture nutrient comprises fetal bovine serum (FBS), glucose, human platelet lysate, bovine serum albumin, fibroblast growth supplement, vitamins, trace elements, antioxidants, minerals, amniotic cell culture supplements, or lipopolysaccharides.

3. The base composition of claim 1, wherein the biological buffer comprises sodium, potassium, magnesium, calcium, alpha hydroxy acid, beta hydroxy acid, polyhydroxy acid, hyaluronic acid, carboxylic acid, or a cell culture buffering agent, or a derivative or any combination thereof, and wherein the biological buffer preserves the biologic at about or above physiological pH.

4. The base composition of claim 3, wherein the biological buffer is sodium citrate.

5. The base composition of claim 1, wherein the biologic is platelet rich plasma (PRP).

6. The base composition of claim 1, further comprising ethylhexylglycerin.

7. The base composition of claim 1, further comprising phenoxyethanol.

8. The base composition of claim 1, further comprising EDTA.

9. The base composition of claim 1, further comprising polysorbate.

10. The base composition of claim 1, further comprising butylene glycol.

11. The base composition of claim 1, further comprising xanthan gum.

12. The base composition of claim 1, further comprising propanediol.

13. The base composition of claim 1, further comprising tocopheryl acetate.

14. The base composition of claim 1, further comprising glycerin.

15. The base composition of claim 1, further comprising shea butter.

16. The base composition of claim 1, further comprising water.

17. The base composition of claim 1, further comprising one or more saccharides.

18. The base composition of claim 1, further comprising grape extract.

19. A base composition for prolonging, preserving, or maintaining a biologic, the composition comprising:
   a cell culture nutrient;
   a biological buffer;
   a polymer;
   a thymol; and
   an antimicrobial.

20. The base composition of claim 19, wherein the polymer comprises a natural or synthetic polymer.

21. The base composition of claim 19, wherein the polymer comprises a starch, a xanthan gum, a guar gum, a carrageenan, an alginate, a polysaccharide, a pectin, a gelatin, an agar, a cellulose, a polyacrylate, a polyacrylamide, honey, hydrogel, chitosan, silicone, or a crosspolymer, copolymer, or derivative thereof.

22. The base composition of claim 19, further comprising a biologic, wherein the biologic comprises platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof.

23. The base composition of claim 22, wherein the biologic is a lyophilized powder.

24. The base composition of claim 19, wherein the base composition prolongs or enhances stability of the biologic and prolongs or enhances stability of components of the biologic.

25. The base composition of claim 19, wherein the base composition inhibits or prevents activation of the biologic, or wherein the base composition maintains, prolongs, preserves, or sustains activity of the biologic or of already active components of the biologic.

26. The base composition of claim 19, wherein the base composition is formulated for cosmetic usage, wherein the cosmetic usage comprises topical application to skin.

27. A topical formulation, comprising:
   a base composition comprising a cell culture nutrient, a biological buffer, a viscosity modifying agent, and a botanical extract; and
   a biologic,
   wherein the formulation is formulated as a cream, lotion, salve, paste, serum, gel, ointment, liquid, solution, spray, aerosol, or foam.

28. The topical formulation of claim 27, wherein the biologic comprises platelet rich plasma (PRP), fibroblast cells, adipose tissue, adipose derived stromal vascular function (SVF), nanofat, lipoaspirate components, bone marrow derived mesenchymal stem cells, adipose derived stem cells, platelet derived exosomes, adipose derived exosomes, alpha 2 macroglobulin (A2M), human platelet lysate, or isolated microparticles thereof.

29. The topical formulation of claim 27, wherein the topical formulation is formulated for cosmetic usage, wherein the cosmetic usage comprises topical application to skin.

30. A method of diminishing pore size, diminishing bacteria damage, diminishing red areas, reducing skin damage caused by sun, restoring or preventing hair loss, reducing nail disorder, or maintaining or improving skin tone in a subject in need thereof, the method comprising:
    obtaining whole blood from a subject having an area of skin damage, a skin disorder, a nail disorder, or hair loss;
    centrifuging the blood to separate platelet rich plasma from platelet poor plasma and red blood cells;
    collecting the platelet rich plasma (PRP);
    adding a base composition comprising a cell culture nutrient, a biological buffer, a viscosity modifying agent, and a botanical extract to the PRP to form PRP admixed solution thereby forming a first topical formulation, wherein the base composition maintains activity of the PRP for a period of time ranging from 30 to 120 days;
    providing the first topical formulation for application to the subject for treatment of the area of skin damage, nail damage, or hair loss; and
    activating the PRP.

31. The method of claim 30, wherein activating PRP comprises increasing the temperature or applying mechanical force, wherein increasing the temperature is achieved by applying mechanical force to the first topical formulation or by removing the first topical formulation from a temperature of less than about 10° C. to a temperature of at least room temperature.

32. The method of claim 31, wherein the mechanical force comprises rubbing, massaging, spreading, or using a mechanical device.

33. The method of claim 32, wherein the mechanical device comprises a microdermabrasion, an oscillating fiber, a suction, a microneedling, a roller, or a mechanical cleansing device.

34. The method of claim 30, further comprising providing a second topical formulation for application to the subject over the first topical formulation, wherein the second topical formulation activates the PRP, wherein the second topical formulation comprises a cell stimulation cocktail comprising calcium chloride, hydrochloric acid, thrombin, autologous thrombin, bovine thrombin, collagen, calcium, magnesium, sodium, components of snake venom, batroxobin, or combinations thereof.

35. The method of claim 30, wherein the subject suffers from skin damage and signs of aging caused by smoking, alcohol, diet, extreme temperatures, chemicals, stress, lack of sleep, poor diet, poor immune system or a combination thereof.

36. The method of claim 30, wherein the skin disorder is selected from a group consisting of stretch marks (striae), psoriasis, skin cancer, acne, alopecia, carbuncles, dermatitis, eczema, atopic dermatitis, contact dermatitis, seborrheic dermatitis, cradle cap, perioral dermatitis, shingles, ringworm, melisma, impetigo, acne aestivalis (Mallorca acne), acne conglobate, acne cosmetica (cosmetic acne), acne fulminans (acute febrile ulcerative acne), acne keloidalis nuchae (acne keloidalis, dermatitis papillaris capillitii, folliculitis keloidalis, folliculitis keloidis nuchae, nuchal keloid acne), adult forehead with scattered red pimples, acne vulgaris, acne mechanica, acne medicamentosa, acne miliaris necrotica (acne varioliformis), acne vulgaris, acne with facial edema (solid facial edema), blepharophyma, erythrotelangiectatic rosacea (erythematotelangiectatic rosacea, vascular rosacea), excoriated acne (acne excoriée des jeunes filles, Picker's acne), glandular rosacea, gnathophyma, gram-negative rosacea, granulomatous facial dermatitis, rhinophyma, granulomatous perioral dermatitis, halogen acne, hidradenitis suppurativa (acne inversa, pyoderma fistulans significa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum, neonatal cephalic pustulosis), occupational acne, oil acne, ocular rosacea (ophthalmic rosacea, ophthalmorosacea), otophyma, periorificial dermatitis, persistent edema of rosacea (chronic upper facial erythematous edema, Morbihan's disease, rosaceous lymphedema), phymatous rosacea, pomade acne, papulopustular rosacea (inflammatory rosacea), perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobate, synovitis-acne-pustulosis-hyperostosis-osteomyelitis syndrome (SAPHO syndrome), steroid rosacea, tar acne, skin cancer, tropical acne or a combination thereof.

* * * * *